United States Patent [19]

Meyer et al.

[11] Patent Number: 5,792,767

[45] Date of Patent: *Aug. 11, 1998

[54] BICYCLIC SUBSTITUTED HEXAHYDROBENZ [E] ISOINDOLE ALPHA-1 ADRENERGIC ANTAGONISTS

[75] Inventors: Michael D. Meyer, Lake Villa; Robert J. Altenbach, Chicago; Fatima Z. Basha, Lake Forest; William A. Carroll, Evanston; Irene Drizin, Wadsworth; James F. Kerwin, Jr., Grayslake; Suzanne A. Lebold, Chicago; Edmund L. Lee, Lake Zurich, all of Ill.; John K. Pratt, Kenosha, Wis.; Kevin B. Sippy, Lindenhurst, Ill.; Karin R. Tietje, Mundelein, Ill.; Diane M. Yamamoto, Gurnee, Ill.

[73] Assignee: Abbott Laboratories, Abbott Park, Ill.

[ * ] Notice: The term of this patent shall not extend beyond the expiration date of Pat. No. 5,521,181.

[21] Appl. No.: 465,476

[22] Filed: Jun. 5, 1995

Related U.S. Application Data

[63] Continuation-in-part of Ser. No. 379,823, Jan. 27, 1995, Pat. No. 5,521,181.

[51] Int. Cl.[6] ............... A61K 31/495; A61K 31/505; C07D 403/06; C07D 403/14
[52] U.S. Cl. ............... 514/249; 514/253; 514/258; 514/259; 544/236; 544/257; 544/262; 544/278; 544/279; 544/285
[58] Field of Search ............... 544/236, 257, 544/262, 278, 279, 285; 514/249, 253, 258, 259

[56] References Cited

U.S. PATENT DOCUMENTS

| | | | |
|---|---|---|---|
| 5,158,953 | 10/1992 | Chern et al. | 514/267 |
| 5,420,128 | 5/1995 | Kiyokawa et al. | 514/246 |
| 5,521,181 | 5/1996 | Meyer et al. | 514/249 |

FOREIGN PATENT DOCUMENTS

| | | | |
|---|---|---|---|
| 0095666 | 12/1983 | European Pat. Off. | C07D 209/62 |
| 03259630 | 8/1989 | European Pat. Off. | C07C 87/28 |
| 8906534 | 7/1989 | WIPO | C07D 311/04 |
| 8906645 | 7/1989 | WIPO | C07C 91/28 |
| 9312754 | 7/1993 | WIPO | . |
| 9410989 | 5/1994 | WIPO | A61K 31/135 |

OTHER PUBLICATIONS

"Alpha–1Adrenoceptors in Human Prostate: Characterization and Alteration in enign Prostatic Hypertrophy," The Journal of Pharmacoogy and Experimental Therapeutics vol. 242, No. 1, pp. 326–330 Yamada et al., (1987).

"A–75169 HCl: Pharmacological Profile and Ocular Pharmacology Studies of a New α–2 Antagonist" Drug Development Research 28–:56–64 (1993) Giardina et al.

"Preparation and In Vitro Biological Evaluation of the Enantiomers of the Dihydropyridine BMY 20014, A combination calcium and α1–Adrenoreceptor Antagonist" Lawson et al., Bioorganic and Medicinal Chemistry Leters, vol. 3, No. 4, pp. 562–564 (1993).

*Primary Examiner*—Matthew V. Grumbling
*Attorney, Agent, or Firm*—Jerry F. Janssen; Gregory W. Steele; Frank Z. Wang

[57] ABSTRACT

The present invention relates to a compound of the formula

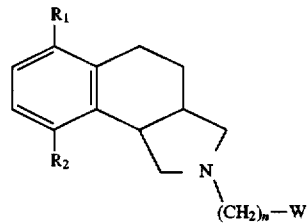

and the pharmaceutically acceptable salts thereof wherein W is a bicyclic heterocyclic ring system. The compounds are α-1 adrenergic antagonists and are useful in the treatment of BPH; also disclosed are α-1 antagonist compositions and a method for antagonizing α-1 receptors and treating BPH.

6 Claims, No Drawings

BICYCLIC SUBSTITUTED HEXAHYDROBENZ [E] ISOINDOLE ALPHA-1 ADRENERGIC ANTAGONISTS

CROSS-REFERENCE TO RELATED APPLICATIONS

This application is a continuation-in-part of application Ser. No. 08/379,823 filed Jan. 27, 1995 now U.S. Pat. No. 5,521,181.

TECHNICAL FIELD

The present invention relates to novel organic compounds and compositions which are alpha-1 ($\alpha$-1) adrenoreceptor antagonists, processes for making such compounds, synthetic intermediates employed in these processes, and a method for inhibiting alpha-1 adrenoceptors and treating benign prostatic hyperplasia (BPH), also called benign prostatic hypertrophy.

BACKGROUND OF THE INVENTION

Adrenergic neurons play a major role in the innervation of heart, blood vessel and smooth muscle tissue. Compounds capable of interacting with adrenoceptor sites within adrenergic nerves can initiate a variety of physiological responses, including vasoconstriction, vasodilation, and increased or decreased heart rate (chronotropic), contractility (inotropic) and metabolic activity. In the past, various adrenergic compounds have been employed to affect these and other physiological responses. However, many adrenergic compounds do not possess significant selectivity to enable desirable interactions with adrenergic receptor sites. That is, these adrenergic compounds do not demonstrate a high degree of specificity for differing receptor types within adrenergic neurons in order to obtain a desired physiological response separate from other possible, and perhaps less desirable, responses of the system.

Benign prostatic hyperplasia (BPH) is a condition which develops in middle-aged and elderly males and refers to the benign overgrowth of the stromal and epithelial elements of the prostate associated with aging. Symptoms of BPH include increased frequency of urination, nocturia, a weak urine stream and hesitancy or delay in starting the urine flow. Chronic consequences of BPH can include hypertrophy of bladder smooth muscle, a decompensated bladder and an increased incidence of urinary tract infection.

Typically, BPH begins at an age in the mid-fifties and is the most common cause of urinary tract problems of men of this age. BPH is apparently rare in men prior to age 40, but at age 60, approximately 50% of men have histological evidence of BPH. The prevalence of BPH continues to increase with age until, at age 80, approximately 80% of men have pathological evidence of BPH.

Although prostatic hyperplasia is a common finding in older men, the presence of urinary symptoms is the essential feature that distinguishes simple anatomic enlargement of the prostate from prostatism, which is the clinical syndrome whereby the patient experiences significant obstruction of urinary flow. It is not uncommon in older men to have a palpably enlarged prostate without showing the symptoms of prostatism. From the patient's perspective, however, the incidence and progression of urinary symptoms are more important than the mere presence of an enlarged prostate.

The discovery in the 1970's (M. Caine, et al., Brit. J. Urol., 47: 193–202 (1975)) of large numbers of alpha-adrenergic receptors in the smooth muscle of the prostatic capsule and bladder neck led to the conclusion that there is both a static and a dynamic component to bladder outlet obstruction associated with BPH. The static component derives from the progressive hyperplasia of the prostate with aging, leading to urethral narrowing which causes symptoms of urinary obstruction. Superimposed on this essentially mechanical problem is the variable degree of smooth muscle contraction controlled by the sympatheic nervous system and which is affected by by factors such as stress, cold and sympathomimetic drugs. It is this dynamic component which explains the often rapid fluctuations in symptoms observed in patients with prostatism.

The currently most effective treatment for BPH is the surgical procedure of transurethral resection of the prostate (TURP) Since it removes the obstructing tissue (C. Chapple, Br. Med. Journal 304: 1198–1199 (1992)) it is a treatment which is directed to the static and dynamic components of BPH. However, this surgical treatment is associated with rates of mortality (1%) and adverse event (incontinence 2–4%, infection 5–10%, and impotence 5–10%). A non-invasive alternative treatment would thus be highly desirable.

The incidental clinical observation that urinary incontinence developed in women during antihypertensive treatment with prazosin (T. Thien, K. P. Delacre, F. M. J. Debruyne, R. A. P. Koene, Br. Med. Journal, 622–623 (1978)) and the experimental work of Caine (op cit.) contributed to the recognition of the potential role of selective $\alpha$-1 adrenoceptor blockade in diseases of the lower urinary tract. Subsequent studies by several groups have documented the functional role of $\alpha$-1 adrenoceptors relative to $\alpha$-2 adrenoceptors in the stromal compartment of the prostate, thereby providing a putative molecular basis for the use of specific $\alpha$-1 adrenoceptor blockers in the non-surgical management of BPH (C. R. Chapple, M. L. Aubry, S. James, M. Greengrass, G. Burnstock, R. T. Turner-Warwick, Br. J. Urol. 63: 487–496 (1989)). Clinical efficacy of $\alpha$-1 antagonists in BPH has been demonstrated with several nonselective $\alpha$-1 blockers, including terazosin (Hytrin®), prazosin, and doxazosin. Treatment periods as short as two to four weeks with $\alpha$-1 adrenoceptor blockers have shown objective improvements in the mean and maximum urinary flow rates (14–96%) with subjective improvements in patients' symptom scores (R. A. Janknegt, C. R. Chapple, Eur. Urol. 24: 319–326 (1993)). Longer term studies with terazosin, indoramin, prazosin, and doxazosin have similarly demonstrated significant improvements in urinary flow rates and subjective symptom scores (R. A. Janknegt, op. cit., H. Lepor, G. Knapp-Maloney, J. Urol. 145: 263A (1991), W. Chow, D. Hahn, D. Sandhu, Br. J. Urol. 65: 36–38 (1990) and C. R. Chapple, T. J. Christmas, E. J. G. Milroy, Urol. Int. 45: 47–55 (1990)). However, these agents possess similar dose limiting side effects: hypotension, dizziness, and muscle fatigue. There thus exists a need for a "uroselective" $\alpha$-1 antagonist with reduced side effect liabilities.

SUMMARY OF THE INVENTION

In its principle embodiment, the present invention provides certain hexahydro-[1H]-benz[e]isoindole compounds of the formula I:

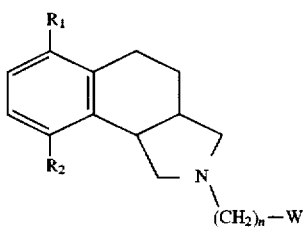

or a pharmaceutically acceptable salt thereof wherein n is an integer from 2 to 6.

$R_1$ and $R_2$ are independently selected from the group consisting of hydrogen, alkyl of one to six carbon atom, alkoxy of one to six carbon atoms, hydroxy, halo, carboxy, and alkoxycarbonyl of two to eight carbon atoms.

W is selected from the group consisting of

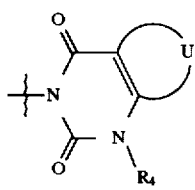

and

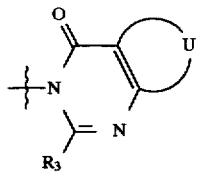

wherein $R_3$ is selected from the group consisting of hydrogen, alkyl of one to six carbon atoms, unsubstituted phenyl and phenyl substituted with alkyl of one to six carbon atoms, and $R_4$ is hydrogen or alkyl of one to six carbon atoms.

U, taken together with the carbon atoms to which it is attached forms a ring selected from the group consisting of (a) an unsubstituted or substituted five membered ring having four carbon atoms, two double bonds and one heteroatom selected from the group consisting of —N($R_5$) —, —O— and —S— wherein $R_5$ is hydrogen or alkyl of one to six carbon atoms and the ring substituent is selected from the group consisting of alkyl of one to six carbon atoms, phenyl, halo, cyano, nitro, carboxy, alkoxycarbonyl of two to eight carbon atoms and alkoxy of one to six carbon atoms; (b) an unsubstituted or substituted five membered ring having three carbon atoms, two double bonds and two heteroatoms selected from the group consisting of two nitrogen atoms, one oxygen atom and one nitrogen atom, and one sulfur atom and one nitrogen atom wherein the ring substituent is selected from the group consisting of alkyl of one to six carbon atoms, phenyl, halo, cyano, nitro, carboxy, alkoxycarbonyl of two to eight carbon atoms and alkoxy of one to six carbon atoms; (c) a benzene ring which is unsubstituted or substituted with a substitutent selected from the group consisting of alkyl of one to six carbon atoms, phenyl, halo, cyano, nitro, carboxy, alkoxycarbonyl of two to eight carbon atoms and alkoxy of one to six carbon atoms methylenedioxy and ethylenedioxy; and (d) an unsubstituted or substituted six membered ring having one to three double bonds and one or two nitrogen atoms, wherein the ring substituent is selected from the group consisting of alkyl of one to six carbon atoms, phenyl, halo, cyano, nitro, carboxy, alkoxycarbonyl of two to eight carbon atoms and alkoxy of one to six carbon atoms.

In one embodiment, the present invention provides a compound of the formula

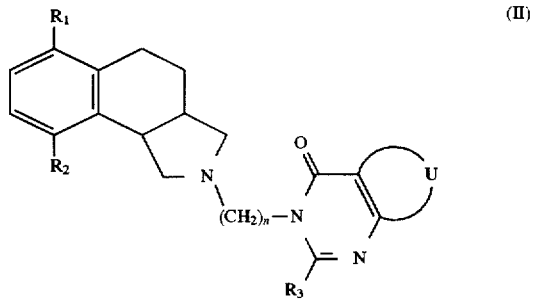

(II)

wherein $R_1$, $R_2$, n, $R_3$ and U are as previously defined.

In another embodiment, the present invention provides a compound of the formula

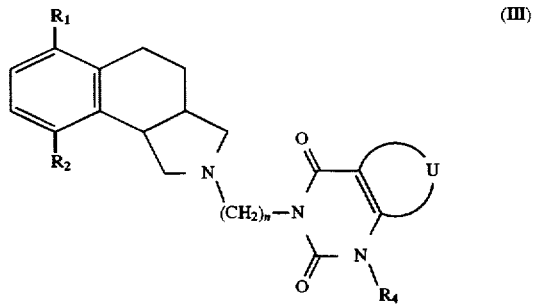

(III)

wherein $R_1$, $R_2$, n, $R_4$ and U are as previously defined.

Yet another embodiment of the present invention provides a compound of formula (I) wherein W is selected from the group consisting of

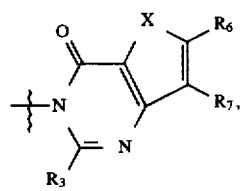

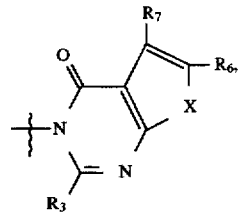

and

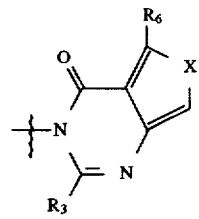

wherein X is selected from the group consisting of —N(R$_5$)—, —O— and —S— wherein R$_5$ is hydrogen or alkyl of one to six carbon atoms, R$_6$ and R$_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, and R$_3$ is as previously defined.

In yet another embodiment of the present invention provides a compound of formula (I) wherein W is selected from the group consisting of

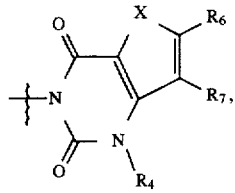

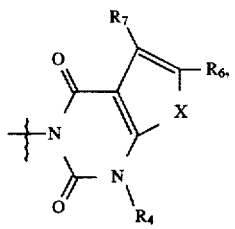

and

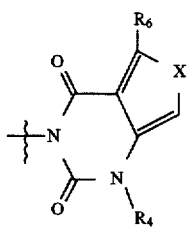

wherein X is selected from the group consisting of —N(R$_5$)—, —O— and —S— wherein R$_5$ is hydrogen or alkyl of one to six carbon atoms, R$_6$ and R$_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, and R$_4$ is as previously defined.

Another embodiment of the present invention provides a compound of formula (I) wherein W is selected from the group consisting of

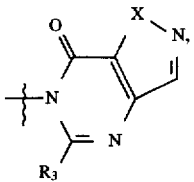

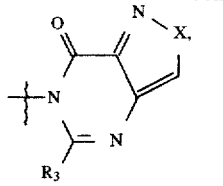

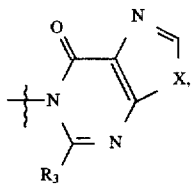

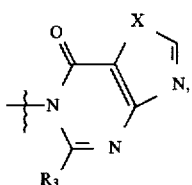

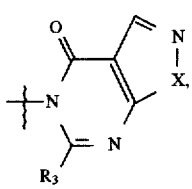

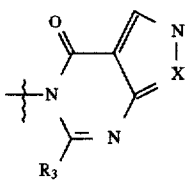

and

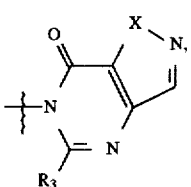

wherein X is selected from the group consisting of —N(R$_5$) —, —O— and —S— wherein R$_5$ is hydrogen or alkyl of one to six carbon atoms and R$_3$ is as previously defined.

Another embodiment of the present invention provides a compound of formula (I) wherein W is selected from the group consisting of

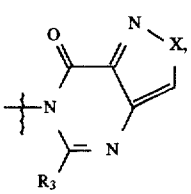

-continued

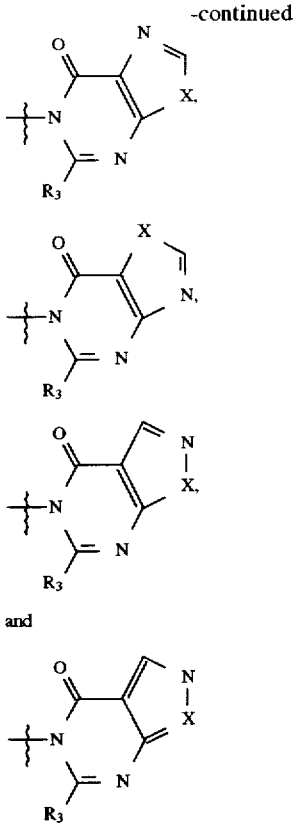

wherein X is selected from the group consisting of —N(R$_5$)—, —O— and —S— wherein R$_5$ is hydrogen or alkyl of one to six carbon atoms and R$_4$ is as previously defined.

Yet another embodiment of the present invention provides a compound of formula (I) wherein W is

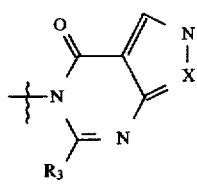

wherein m is selected from 1, 2 and 3 and, when m is 2 or 3, R$_8$ at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is 2, methylenedioxy and ethylenedioxy, and R$_3$ is as previously defined.

Another embodiment of the present invention provides a compound of formula (I) wherein W is

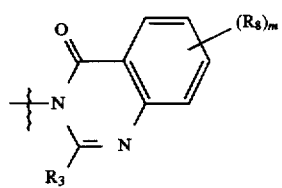

wherein m is selected from 1, 2 and 3 and, when m is 2 or 3, R$_8$ at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is 2, methylenedioxy and ethylenedioxy, and R$_4$ is as previously defined.

In yet another embodiment, the present invention provides a compound of formula (I) wherein W is selected from the group consisting of

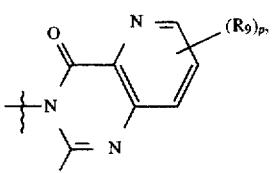

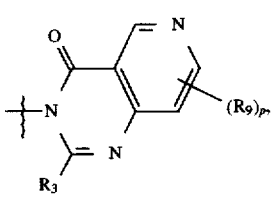

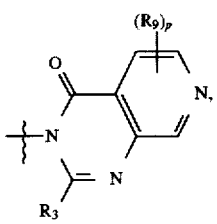

and

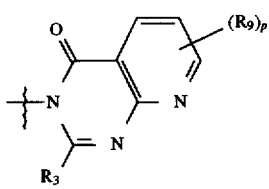

wherein p is selected from 1 and 2 and, when p is 2, R$_9$ at each occurence is independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, and R$_3$ is as previously defined.

Another embodiment of the present invention provides a compound of formula (I) wherein W is selected from the group consisting of

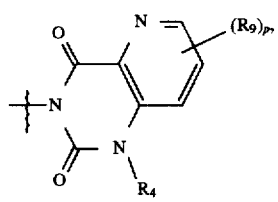

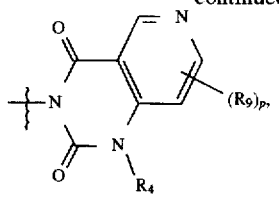

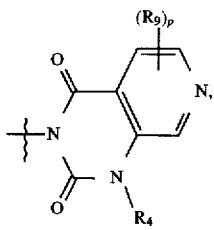

and

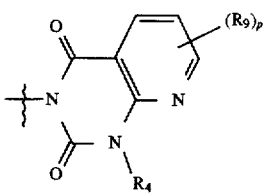

wherein p is selected from 1 and 2 and, when p is 2, $R_9$ at each occurence is independently selected from the group consisting of hydrogen, alkyl of one to six carbon atoms, phenyl, halo, cyano, nitro, carboxy, alkoxycarbonyl of two to eight carbon atoms, and alkoxy of one to six carbon atoms, and $R_4$ is as previously defined.

Another embodiment of the present invention provides a compound of formula (I) wherein W is selected from the group consisting of

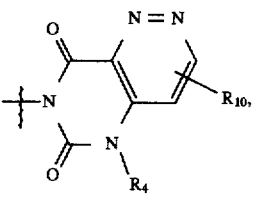

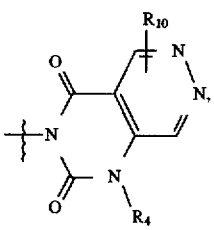

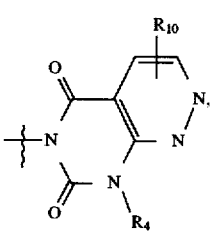

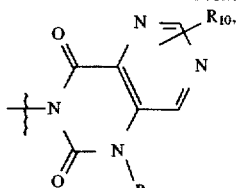

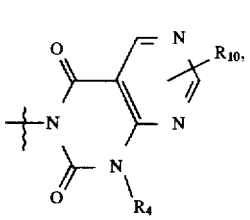

and

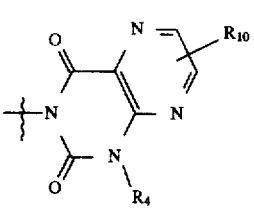

wherein $R_{10}$ is selected from the group consisting of hydrogen, alkyl of one to six carbon atoms, phenyl, halo, cyano, nitro, carboxy, alkoxycarbonyl of two to eight carbon atoms and alkoxy of one to six carbon atoms and $R_4$ is as previously defined.

Another embodiment of the present invention provides a compound of formula (I) wherein W is selected from the group consisting of

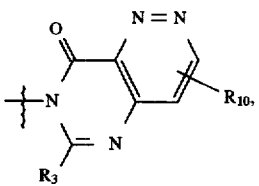

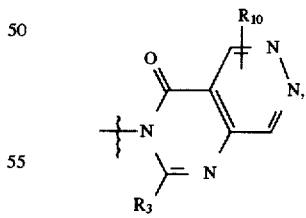

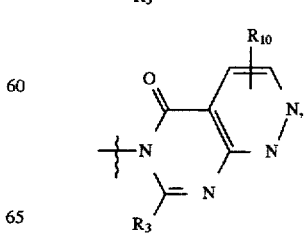

-continued

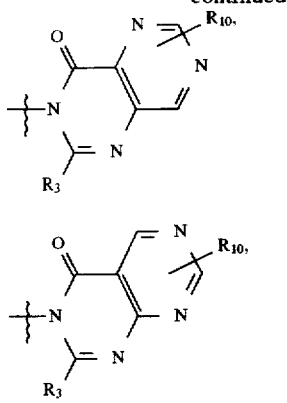

and

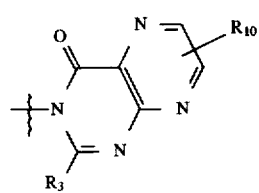

wherein $R_{10}$ is selected from the group consisting of hydrogen, alkyl of one to six carbon atoms, phenyl, halo, cyano, nitro, carboxy, alkoxycarbonyl of two to eight carbon atoms, and alkoxy of one to six carbon atoms and $R_3$ is as previously defined.

A preferred embodiment of the present invention provides a compound of formula (I) wherein W is selected from the group consisting of

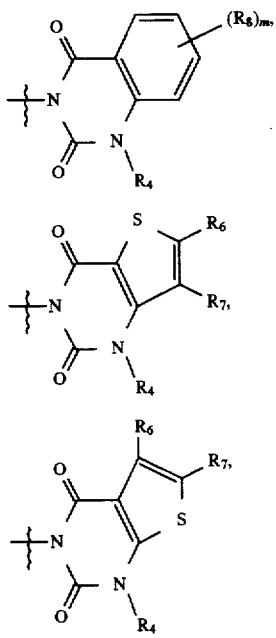

and

-continued

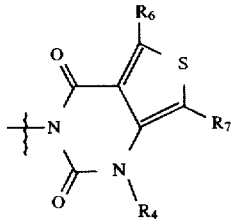

wherein $R_1$, $R_2$, n, m, $R_4$, $R_6$, $R_7$ and $R_8$ are as previously defined.

A more preferred embodiment of the present invention is a compound of formula (I) wherein one of $R_1$ and $R_2$ is alkoxy of one to six carbon atoms and the other one is hydrogen, n is selected from an integer from 2 to 4 and W is selected from the group consisting of

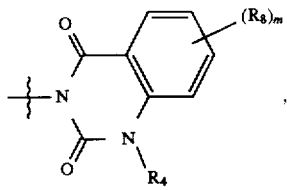

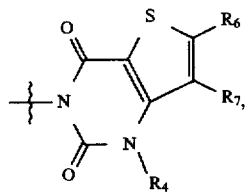

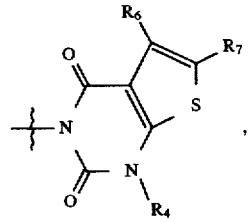

and 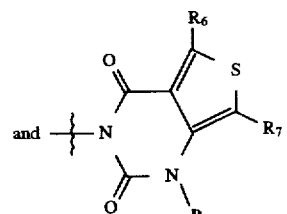

wherein $R_1$, $R_2$, n, m, $R_4$, $R_6$, $R_7$ and $R_8$ are as previously defined.

The present invention also relates to pharmaceutical compositions which comprise a therapeutically effective amount of a compound of claim 1 in combination with a pharmaceutically acceptable carrier.

The invention further relates to a method of antagonizing α-1 receptors in a host mammal in need of such treatment a therapeutically effective amount of a compound of claim 1.

The invention still further relates to a method of treating BPH in a host mammal in need of such treatment a therapeutically effective amount of a compound of claim 1.

DETAILED DESCRIPTION OF THE INVENTION

As used throughout this specification and the appended claims, the following terms have the meaning specified.

The term "alkyl" as used herein refer to straight or branched chain alkyl radicals including, but not limited to, methyl, ethyl, n-propyl, iso-propyl, n-butyl, iso-butyl, sec-butyl, t-butyl, n-pentyl, 1-methylbutyl, 2,2-dimethylbutyl, 2-methylpentyl, 2,2-dimethylpropyl, n-hexyl and the like.

The term "alkoxy" as used herein refers to an alkyl group, as previously defined, attached to the parent molecular moiety through an oxygen atom. Examples of alkoxy include, but are not limited to, methoxy, ethoxy, isopropoxy, tert-butoxy, and the like.

The term "alkoxycarbonyl" as used herein refers to an alkoxyl group as previously defined appended to the parent molecular moiety through a carbonyl group. Examples of alkoxycarbonyl include, but are not limited to, methoxycarbonyl, ethoxycarbonyl, isopropoxycarbonyl and the like.

The term "ethylenedioxy" as used herein refers to —O—CH$_2$—CH$_2$—O— which when attached to two adjacent positions on a benzene ring forms a six-membered ring.

The term "methylenedioxy" as used herein refers to —O—CH$_2$—O— which when attached to two adjacent positions on a benzene ring forms a 5-membered ring.

By "pharmaceutically acceptable salt" is meant those salts which are, within the scope of sound medical judgement, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharrnaceutically acceptable salts in detail in *J. Pharm. Sciences*, 66: 1–19 (1977). The compounds of the present invention can be used in the form of salts derived from inorganic or organic acids. The salts can be prepared in situ during the final isolation and purification of the compounds of the invention, or separately by reacting the free base function with a suitable organic acid. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulphuric acid and phosphoric acid and such organic acids as oxalic acid, maleic acid, succinic acid and citric acid. Basic addition salts can be prepared in situ during the final isolation and purification of the compounds of formula (I), or separately by reacting the carboxylic acid function with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

Asymmetric centers may exist in the compounds of the present invention. The present invention comtemplates the various stereoisomers and mixtures thereof. Starting compounds of particular stereochemistry are either commercially available or are made by the methods detailed below and resolved by techniques well known in the art of organic chemistry.

Representative examples of compounds falling within the scope of this invention include:

3-[2-(cis-9-methoxy-2,3,3a,4,5,9b-hexahydro-[1H]-benz[e]isoindol-1-yl)ethyl]-[1H,3H]-quinazoline-2,4(1H,3H)-dione;

3-[2-(cis-9-methoxy-2,3,3a,4,5,9b-hexahydro-[1H]-benz[e]isoindol-1-yl)ethyl]-7-methylthieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-5methylthieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-5-phenyl-thieno[2,3-d]pyrimidine-2,4(1H,3H)-dione hydrochloride;

3-[2-(cis-6-methoxy-2,3,3a,4,5,9b-hexahydro-[1H]-benz[e]isoindol-1-yl)ethyl]-6-phenyl-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-thieno[3,4d]pyrimidine-2,4(1H,3H)-dione;

3-[2-(cis-6-methoxy-2,3,3a,4,5,9b-hexahydro-[1H]-benz[e]isoindol-1-yl)ethyl]-8-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,7-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7-chloro-quinazoline-2,4(1H,3H)-dione;

3-[2-(cis-6-methoxy-2,3,3a,4,5,9b-hexahydro-[1H]-benz[e]isoindol-1-yl)ethyl]-5-methyl-quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-7-carbomethoxy-quinazoline-2,4(1H,3H)-dione;

3-[2-(cis-6-methoxy-2,3,3a,4,5,9b-hexahydro-[1H]-benz[e]isoindol-1-yl)ethyl]-6-fluoro-quinazoline-2,4(1H,3H)-dione;

3-[2-(cis-6-methoxy-2,3,3a,4,5,9b-hexahydro-[1H]-benz[e]isoindol-1-yl)ethyl]-6-nitro-quinazoline-2,4(1H,3H)-dione;

3-[2-(cis-6-methoxy-2,3,3a,4,5,9b-hexahydro-[1H]-benz[e]isoindol-1-yl)ethyl]-6-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,7,8-trimethoxy-quinazoline-2,4(1H,3H)-dione;

3-[2-(cis-6-methoxy-2,3,3a,4,5,9b-hexahydro-[1H]-benz[e]isoindol-1-yl)ethyl]-8-methyl-quinazoline-2,4(1H,3H)-dione;

3-[2-(cis-6-methoxy-2,3,3a,4,5,9b-hexahydro-[1H]-benz[e]isoindol-1-yl)ethyl]-6,8-dimethyl-quinazoline-2,4(1H,3H)-dione;

3-[2-(cis-6-methoxy-2,3,3a,4,5,9b-hexahydro-[1H]-benz[e]isoindol-1-yl)ethyl]-pyrido[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-pyrido[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-5chloro-quinazoline-2,4(1H,3H)-dione;

3-[2-(cis-6-methoxy-2,3,3a,4,5,9b-hexahydro-[1H]-benz[e]isoindol-1-yl)ethyl]-pyrido[3,4-d]pyrimidine-2,4(1H,3H)-dione;

3-[2-(cis-6-methoxy-2,3,3a,4,5,9b-hexahydro-[1H]-benz[e]isoindol-1-yl)ethyl]-7-fluoro-quinazoline-2,4(1H,3H)-dione;

3-[2-(cis-6-methoxy-2,3,3a,4,5,9b-hexahydro-[1H]-benz[e]isoindol-1-yl)ethyl]-1-methyl-quinazoline-2,4(1H,3H)-dione;

3-[2-(cis-6-methoxy-2,3,3a,4,5,9b-hexahydro-[1H]-benz[e]isoindol-1-yl)ethyl]-pyrido[4,3-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-1H-pyrazolo[3,4-d]pyrimidine-4,6(5H,7H)-dione;

3-[2-(cis-6-methoxy-2,3,3a,4,5,9b-hexahydro-[1H]-benz[e]isoindol-1-yl)ethyl]-&methylthieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-1H-pyrrolo[2,3-d]pyrimidine-2,4(3H,7H)-dione;

3-[2-(cis-6-methoxy-2,3,3a,4,5,9b-hexahydro-[1H]-benz[e]isoindol-1-yl)ethyl]-7-phenylthieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-6-phenylthieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-6,7-dimethoxy-quinazoline-4(3H)-one;

3-[2-(cis-6-methoxy-2,3,3a,4,5,9b-hexahydro-[1H]-benz[e]isoindol-1-yl)ethyl]-quinazoline-4(3H)-one;

3-[2-(cis-6-hydroxy-2,3,3a,4,5,9b-hexahydro-[1H]-benz[e]isoindol-1-yl)ethyl]-thieno[2,3-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-quinazoline-2(1H)-one;

3-[2-((3aR,9bR)-cis-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-ethylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-dimethoxyquinazoline-2,4(1H,3H)-dione;

3-[2-((3aR,9bR)-cis-6-methoxy-2,3,3a,4,5,9bhexahydro-[1H]-benz[e]isoindol-1-yl)ethyl]-1-methyl-6,7-dimethoxyquinazoline-2,4(1H,3H)-dione;

3-[2-(cis-6-methoxy-2,3,3a,4,5,9b-hexahydro-[1H]-benz[e]isoindol-1-yl)ethyl]-6-methoxy-thieno[3,2-d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-dimethoxyquinazoline4(3H)-one;

3-[2-((3aR,9bR)-cis-6-methoxy-2,3,3a,4,5,9b-hexahydro-[1H]-benz[e]isoindol-1-yl)ethyl]-thieno[2,3-d]pyrimidine-4(3H)-one;

3-[2-((3aR,9bR)-cis-6-methoxy-2,3,3a,4,5,9b-hexahydro-[1H]-benz[e]isoindol-1-yl)ethyl]-quinazoline-2(1H)-one;

3-[2-(cis-6-methoxy-2,3,3a,4,5,9b-hexahydro-[1H]-benz[e]isoindol-1-yl)ethyl]-quinazoline-4(3H)-one;

2-[2-(cis-6-methoxy-2,3,3a,4,5,9b-hexahydro-[1H]-benz[e]isoindol-1-yl)ethyl]-1,2,3,4tetrahydroisoquinolin-1,3-dione;

2-[2-(cis-6-methoxy-2,3,3a,4,5,9b-hexahydro-[1H]-benz[e]isoindol-1-yl)ethyl]-6,7-dimethoxy-1,2,3,4-tetrahydroisoquinoline;

3-[2-(cis-6-methoxy-2,3,3a,4,5,9b-hexahydro-[1H]-benz[e]isoindol-1-yl)ethyl]-2,4pteridinedione;

3-[2-(cis-6-methoxy-2,3,3a,4,5,9b-hexahydro-[1H]-benz[e]isoindol-1-yl)ethyl]-7-(3,4dimethoxyphenyl)-thieno[3,2-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-6-chlorothieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-1-methyl-6-dimethylaminocarbonyl-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]oxazolo[5,4d]pyrimidine-5,7(4H,6H)-dione;

3-[2-(cis-6-methoxy-2,3,3a,4,5,9b-hexahydro-[1H]-benz[e]isoindol-1-yl)ethyl]-7-amino-oxazolo[5,4d]pyrimidin-5(6H)-one;

1-[2-(cis-6-methoxy-2,3,3a,4,5,9b-hexahydro-[1H]-benz[e]isoindol 1-yl)ethyl]-3,9-dimethyl-[1H]-purine-2,6-dione;

1-[2-(cis-6-methoxy-2,3,3a,4,5,9b-hexahydro-[1H]-benz[e]isoindol-1-yl)ethyl]-3,7-dimethyl-[7H]-imidazo[4,5-d]pyrimidin-2,6-dione;

3-[4-(cis-9-methoxy-2,3,3a,4,5,9b-hexahydro-[1H]-benz[e]isoindol-1-yl)butyl]-6,7-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7,8-dimethoxy-quinazoline-2,4(1H,3H)-dione;

3-|2-(cis-6-methoxy-2,3,3a,4,5,9b-hexahydro-|1H|-benz|e|isoindol-1-yl)ethyl||-7-methoxy-quinazoline-2,4(1H,3H)-dione;

3-|2-(cis-6-methoxy-2,3,3a,4,5,9b-hexahydro-|1H|-benz|e|isoindol-1-yl)ethyl||-7,8-dimethyl-quinazoline-2,4(1H,3H)-dione;

3-|2-(cis-6-methoxy-2,3,3a,4,5,9b-hexahydro-|1H|-benz|e|isoindol-1-yl)ethyl||-7-methylsulfonylamino-quinazoline-2,4(1H,3H)-dione;

3-|2-(cis-6-methoxy-2,3,3a,4,5,9b-hexahydro-|1H|-benz|e|isoindol-1-yl)ethyl||-7,8-ethylenedioxy-quinazoline-2,4(1H,3H)-dione;

3-|2-(cis-6-hydroxy-2,3,3a,4,5,9b-hexahydro-|1H|-benz|e|isoindol-1-yl)ethyl||-6,7-dimethoxy-quinazoline-2,4(1H,3H)-dione;

2-|2-(cis-6-methoxy-2,3,3a,4,5,9b-hexahydro-|1H|-benz[e]isoindol-1-yl)ethyl||-4amino-6,7-dimethoxy-quinazoline;

3-|2-(cis-6-methoxy-2,3,3a,4,5,9b-hexahydro-|1H|-benz|e|isoindol-1-yl)ethyl||-6-chloro-7-methoxy-quinazoline-2,4(1H,3H)-dione;

3-|2-(cis-6-methoxy-2,3,3a,4,5,9b-hexahydro-|1H|-benz[e]isoindol-1-yl)ethyl||-6-methoxy-7-chloro-quinazoline-2,4(1H,3H)-dione;

3-[2-(cis-6-methoxy-2,3,3a,4,5,9b-hexahydro-|1H|-benz|e|isoindol-1-yl)ethyl]-7-dimethylaminocarbonyl-quinazoline-2,4(1H,3H)-dione;

3-[2-(cis-6-methoxy-2,3,3a,4,5,9b-hexahydro-[1H]-benz[e]isoindol-1-yl)ethyl]]-7-cyano-quinazoline-2,4(1H,3H)-dione;

3-[2-(trans-9-methoxy-2,3,3a,4,5,9b-hexahydro-[1H]-benz[e]isoindol-1-yl)ethyl]-[1H,3H]-quinazoline-2,4(1H,3H)-dione;

3-[2-(trans-6-methoxy-2,3,3a,4,5,9b-hexahydro-[1H]-benz[e]isoindol-1-yl)ethyl]-thieno[3,2-d]pyrimidine-2,4(1H,3H)-dione;

3-[2-(trans-6-methoxy-2,3,3a,4,5,9b-hexahydro-[1H]-benz[e]isoindol-1-yl)ethyl]-8-methoxy-quinazoline-2,4(1H,3H)-dione;

3-[2-(trans-6-methoxy-2,3,3a,4,5,9b-hexahydro-[1H]-benz[e]isoindol-1-yl)ethyl]-6,7-dimethoxy-quinazoline-2,4(1H,3H)-dione;

3-[2-(trans-6-methoxy-2,3,3a,4,5,9b-hexahydro-[1H]-benz[e]isoindol-1-yl)ethyl]-7-chloro-quinazoline-2,4(1H,3H)-dione;

3-[2-(trans-6-methoxy-2,3,3a,4,5,9b-hexahydro-[1H]-benz[e]isoindol-1-yl)ethyl]-7-carbomethoxy-quinazoline-2,4(1H,3H)-dione;

3-[2-(trans-6-methoxy-2,3,3a,4,5,9b-hexahydro-[1H]-benz[e]isoindol-1-yl)ethyl]-6,7,8-trimethoxy-quinazoline-2,4(1H,3H)-dione;

3-[2-(trans-6-methoxy-2,3,3a,4,5,9b-hexahydro-[1H]-benz[e]isoindol-1-yl)ethyl]-1-methylquinazoline-2,4(1H,314)-dione;

3-[2-(trans-6-methoxy-2,3,3a,4,5,9b-hexahydro-[1H]-benz[e]isoindol-1-yl)ethyl]-6,7-dimethoxy-quinazoline-4(3H)-one;

3-[2-(trans-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-(trans-6-methoxy-2,3,3a,4,5,9b-hexahydro-[1H]-benz[e]isoindol-1-yl)ethyl]-6,7-ethylenedioxyquinazoline-2,4(1H,3H)-dione;

3-[2-(trans-6-methoxy-2,3,3a,4,5,9b-hexahydro-[1H]-benz[e]isoindol-1-yl)ethyl]-1-methyl-6,7-dimethoxyquinazoline-2,4(1H,3H)-dione;

3-[2-(trans-6-methoxy-2,3,3a,4,5,9b-hexahydro-[1H]-benz[e]isoindol-1-yl)ethyl]-6-methoxy-thieno[3,2-d]pyrimidine-2,4(1H,3H)-dione;

3-|2-((3aR,9bR)-cis-6-methoxy-2,3,3a,4,5,9b-hexahydro-|1H|-benz|e|isoindol-1-yl)ethyl|-7-carbamylquinazoline-2,4(1H,3H)-dione;

3-|2-((3aR,9bR)-cis-6-methoxy-2,3,3a,4,5,9b-hexahydro-|1H|-benz|e|isoindol-1-yl)ethyl|-7-(N,N'-dimethyl)carbamylquinazoline-2,4(1H,3H)-dione;

3-[2-((3aR,9bR)-cis-6methoxy-2,3,3a,4,5,9b-hexahydro-|1H|-benz|e|isoindol-1-yl)ethyl|-6,8-dichloro-7-methoxyquinazoline-2,4(1H,3H)-dione;

3-|2-((3aR,9bR)-cis-6-methoxy-2,3,3a,4,5,9b-hexahydro-|1H|-benz|e|isoindol-1-yl)ethyl|-7-chloro-6-methoxyquinazoline-2,4(1H,3H)-dione;

3-|2-((3aR,9bR)-cis-6-methoxy-2,3,3a,4,5,9b-hexahydro-|1H|-benz[e]isoindol-1-yl)ethyl|-1-methyl-6-chloro-7-methoxyquinazoline-2,4(1H,3H)-dione;

3-|2-((3aR,9bR)-cis-6-methoxy-2,3,3a,4,5,9b-hexahydro-|1H|-benz[e]isoindol-1-yl)ethyl|-5,6methylenedioxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7,8-dimethylquinazoline4(3H)-one;

3-|2-((3aR,9bR)-cis-6-methoxy-2,3,3a,4,5,9b-hexahydro-[1H]-benz[e]isoindol-1-yl)ethyl]-6-carbomethoxythieno[2,3-d]pyrimidine-2,4(1H,3H)-dione;

3-[2-((3aR,9bR)-cis-6-methoxy-2,3,3a,4,5,9b-hexahydro[1H]-benz[e]isoindol-1-yl)ethyl]-6-carbomethoxythieno[3,2-d]pyrimidine-2,4(1H,3H)-dione;

3-[2-((3aR,9bR)-cis-6-methoxy-2,3,3a,4,5,9b-hexahydro[1H]-benz[e]isoindol-1-yl)ethyl]-5carboethoxy-1H-pyrrolo[2,3-d]pyrimidine-2,4(1H,3H)-dione;

3-[2-((3aR,9bR)-cis-6-methoxy-2,3,3a,4,5,9bhexahydro-[1H]-benz[e]isoindol-1-yl)ethyl]-6methoxy-7-phenylthieno[3,2-d]pyrimidine-2,4(1H,3H)-dione;

3-|2-((3aR,9bR)-cis-6-methoxy-2,3,3a,4,5,9b-hexahydro-[1H]-benz[e]isoindol-1-yl)ethyl]-6-methoxy-7-ethylthieno[3,2-d]pyrimidine-2,4(1H,3H)-dione;

3-|2-((3aR,9bR)-cis-6-methoxy-2,3,3a,4,5,9b-hexahydro-[1H]-benz[e]isoindol-1-yl)ethyl]-6-methoxy-7-methylthieno[3,2-d]pyrimidine-2,4(1H,3H)-dione;

3-|2-((3aR,9bR)-cis-6-methoxy-2,3,3a,4,5,9b-hexahydro-[1H]-benz[e]isoindol-1-yl)ethyl]-6-methoxy-7-isopropylthieno[3,2-d]pyrimidine-2,4(1H,3H)-dione;

3-|2-((3aR,9bR)-cis-6-methoxy-2,3,3a,4,5,9b-hexahydro-[1H]-benz[e]isoindol-1-yl)ethyl]-6,7-dimethylquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carboxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carboisopropoxyquinazoline-2,4(1H,3H)-dione;

3-[2-((3aR,9bR)cis-6-methoxy-2,3,3a,4,5,9b-hexahydro-|1H|-benz[e]isoindol-1-yl)ethyl]-7-acetamidoquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-methanesulfamylquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-(2-methylphenyl)thieno[3,2-d]pyrimidine-2,4(1H,3H)-dione;

3-[2-((3aR,9bR)cis-6-methoxy-2,3,3a,4,5,9b-hexahydro-[1H]-benz[e]isoindol-1-yl)ethyl]-7-(2-methoxyphenyl)thieno[3,2-d]pyrimidine-2,4(1H,3H)-dione;

3-[2-((3aR,9bR)cis-6-methoxy-2,3,3a,4,5,9b-hexahydro-[1H]-benz[e]isoindol-1-yl)ethyl]-7,8-dimethyl-pyrido[4,3-d]pyrimidine-2,4(1H,3H)-dione;

3-[2-((3aR,9bR)cis-6-methoxy-2,3,3a,4,5,9b-hexahydro-[1H]-benz[e]isoindol-1-yl)ethyl]-2,4pteridinedione;

3-[2-((3aR,9bR)cis-6-methoxy-2,3,3a,4,5,9b-hexahydro-[1H]-benz[e]isoindol-1-yl)ethyl]-pyrimidino[4,5d]pyrimidine-2,4(1H,3H)-dione;

3-[2-((3aR,9bR)-cis-6-methoxy-2,3,3a,4,5,9b-hexahydro-[1H]-benz[e]isoindol-1-yl)ethyl]-1-methyl-7-methoxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-1-(2-methoxyethyl)-6,7-dimethoxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-7,8methylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-6,7-dimethoxyquinazoline-4(3H)-one dihydrochloride;

3-[2-((3aR,9bR)cis-6-methoxy-2,3,3a,4,5,9b-hexahydro-[1H]-benz[e]isoindol-1-yl)ethyl]-7,8-dimethoxyquinazoline-4(3H)-one;

3-[2-((3aR,9bR)-cis-6-methoxy-2,3,3a,4,5,9b-hexahydro-[1H]-benz[e]isoindol-1-yl)ethyl]-7,8-dimethylpyrido[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-6,7-dimethoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carbomethoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carboisopropoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carbopropoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-nitroquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-methoxy-8-methylquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-ethoxy-8-methylquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7,8-dimethylquinazoline-2,4(1H,3H)-dione;

3-[2-((3aR,9bR)cis-6-methoxy-2,3,3a,4,5,9b-hexahydro-[1H]H-benz[e]isoindol-1-yl)ethyl]-7,8dimethoxyquinazoline-2,4(1H,3H)-dione;

3-[2-((3aR,9bR)cis-6-ethoxy-2,3,3a,4,5,9b-hexahydro-[1H]-benz[e]isoindol-1-yl)ethyl]-6,7-dimethoxyquinazoline-2,4(1H,3H)-dione; and 3-[2-((3aR,9bR)cis-6-ethyl-2,3,3a,4,5,9b-hexahydro-[1H]-benz[e]isoindol-1-yl)ethyl]-6,7-dimethoxyquinazoline-2,4(1H,3H)-dione; or a pharmaceutically acceptable salt thereof.

Preferred compounds are selected from those having formula (I) wherein one of $R_1$ and $R_2$ is alkoxy of one to six carbon atoms and the other one is hydrogen, n is selected from an integer from 2 to 4, and W is selected from the group consisting of

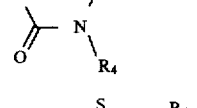

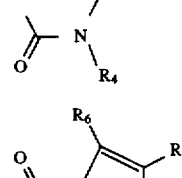

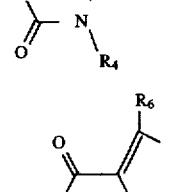

and 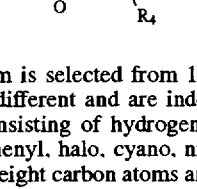

wherein m is selected from 1, 2 and 3, $R_6$ and $R_7$ are the same or different and are independently selected from the group consisting of hydrogen, alkyl of one to six carbon atoms, phenyl, halo, cyano, nitro, carboxy, alkoxycarbonyl of two to eight carbon atoms and alkoxy of one to six carbon atoms, an at each occurence is independently selected from the group consisting of hydrogen, alkyl of one to six carbon atoms, halo, cyano, nitro, carboxy, alkoxycarbonyl of two to eight carbon atoms, alkoxy of one to six carbon atoms and, when m is two, methylenedioxy and ethylenedioxy, and $R_4$ is as previously defined is selected from the group consisting of:

3-[2-(cis-6-methoxy-2,3,3a,4,5,9b-hexahydro-[1H]-benz[e]isoindol-1-yl)ethyl]-8-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,7-dimethoxy-quinazoline-2,4(1H,3H)-dione;

3-[2-(cis-6-methoxy-2,3,3a,4,5,9b-hexahydro-[1H]-benz[e]isoindol-1-yl)ethyl]-7-chloro-quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-thieno[2,3-d]pyrimidine-2,4(1H,3H)-dione;

3-[2-(cis-6-methoxy-2,3,3a,4,5,9b-hexahydro-[1H]-benz[e]isoindol-1-yl)ethyl]-7-carbomethoxy-quinazoline-2,4(1H,3H)-dione;

3-[2-(cis-6-methoxy-2,3,3a,4,5,9b-hexahydro-[1H]-benz[e]isoindol-1-yl)ethyl]-6-methoxy-quinazoline-2,4(1H,3H)-dione;

3-[2-(cis-6-methoxy-2,3,3a,4,5,9b-hexahydro-[1H]-benz[e]isoindol-1-yl)ethyl]-6,8-dimethyl-quinazoline-2,4(H,3H)-dione;

3-[2-(cis-6-methoxy-2,3,3a,4,5,9b-hexahydro-[1H]-benz[e]isoindol-1-yl)ethyl]-1-methyl-quinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-ethylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-dimethoxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-dimethoxy-quinazoline-4(H)-one;

3-[2-((3aR,9bR)-cis-6-Methoxy-2,3,3a,4,5,9b-hexahydro-[1H]-benz[e]isoindol-1-yl)ethyl]-1-methyl-7-methoxyquinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-1-(2-methoxyethyl)-6,7-dimethoxyquinazoline-2,4(1H,3H)-dione;

3-[2-((3aR,9bR)-cis-6Methoxy-2,3,3a,4,5,9b-hexahydro-[1H]-benz[e]isoindol-1-yl)ethyl]-7,8-methylenedioxyquinazoline-2,4(1H,3H)-dione;

3-[2-((3aR,9bR)-cis-6-Methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-6,7-dimethoxyquinazoline-4(3H)-one, 3-[2-((3aR,9bR)cis-6-Methoxy-2,3,3a,4,5,9b-hexahydro-[1H]-benz[e]isoindol-1-yl)ethyl]-7,8-dimethoxyquinazoline-4(3H)-one;

3-[2-((3aR,9bR)-cis-6-Methoxy-2,3,3a,4,5,9b-hexahydro-[1H]-benz[e]isoindol-1-yl)ethyl]-7,9dimethylpyrido[3,2-d]pyrimidine-2,4(1H,3H)-dione;

3-[2-((3aR,9bR)-cis-9-Methoxy-2,3,3a,4,5,9b-hexahydro-[1H]-benz[e]isoindol-1-yl)butyl]6,7-dimethoxyquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7-carbomethoxyquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7-carboisopropoxyquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7-carbopropoxyquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7-nitroquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7-methoxy-8-methyl-quinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7-ethoxy-8-methyl-quinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7,8-dimethylquinazoline-2,4(1H,3H)-dione;

3-[2-((3aR,9bR)cis-6-Methoxy-2,3,3a,4,5,9b-hexahydro-[1H]-benz[e]isoindol-1-yl)ethyl]-7,8-dimethoxyquinazoline-2,4(1H,3H)-dione;

3-[2-((3aR,9bR)cis-6-Ethoxy-2,3,3a,4,5,9b-hexahydro-[1H]-benz[e]isoindol-1-yl)ethyl]-6,7-dimethoxyquinazoline-2,4(1H,3H)-dione; and 3-[2-((3aR,9bR)cis-6-Ethyl-2,3,3a,4,5,9b-hexahydro-[1H]-benz[e]isoindol-1-yl)ethyl]-6,7-dimethoxyquinazoline-2,4(1H,3H)-dione; or a pharmaceutically acceptable salt thereof.

Representative compounds of the present invention were evaluated for their ability to displace prazosin from its receptor.

In Vitro Binding Assays

In the following, for purposes of discussing alpha-1 receptor subtypes, the IUPAC convention of using lower case letters to define molecular clones and upper case letters to indicate pharmacologically defined receptors has been followed. Moreover, the newly recommended nomenclature for alpha-1($\alpha_{1a}$, $\alpha_{1b}$, $\alpha_{1d}$) has been used.

Representative compounds of the invention were evaluated for α-adrenoceptor binding affinity in vitro using [$^3$H]-prazosin as the radioligand and three cloned α-1 adrenoceptors expressed in LTK cells: α-1: α-1a (bovine), α-1b (hamster) and α-1d (rat). Additionally, binding affinity against the pharmacologically defined α-1A adrenoceptor (rat submaxillary gland) was measured.

The cDNA clones encoding the α-1 receptors (α-1a, α-1b, and α-1d) were obtained from TULCO (Triangle Universities Licensing Consortium, Research Triangle Park, N.C.) and inserted into the eukaryotic expression vector SnaB30. In this vector, expression of the receptor gene is under the transcriptional control of an SV40 early promoter. Positive drug selection is provided by a neomycin-resistance gene. Mouse fibroblast cells (LTK) were transfected with the al expression plasmids and grown in Dulbecco's modified Eagle's medium (DMEM) containing 10% fetal calf serum and 30 μM G418. Stable G418-resistant parental lines were generated, with successful expression of receptor protein monitored using radioligand binding techniques. Stable single cell clones derived from the parental lines were screened in receptor binding assays to identify clones having high receptor density. Roller bottle cultures of the cloned lines were used to provide cell membranes for subsequent receptor binding characterization studies. A cell line containing the SnaB30 vector expressing the human erythropoietin gene served as a negative control.

For receptor binding assays, large scale membrane preparations were utilized in which 6 million cells were seeded into small (450 cm$^2$) Corning tissue culture roller bottles. 200 mL of DMEM containing 10% fetal calf serum and 300

µM G418 were added to each roller bottle. A 95% air/5% CO₂ gas mixture (sterile) was injected into each roller bottle prior to sealing. The bottles were then incubated at 37° C. on a roller rack for 5 days. Cells were re-fed with fresh medium after 3 days in culture.

On the fifth day of culture, growth medium was removed from cells grown in roller bottles, and the cells were washed twice with PBS (Sigma, 120 mM NaCl, 2.7 mM KCl, 10 mM Na$_2$HPO$_4$-NaH$_2$PO$_4$, pH=7.4). Cells were detached from the roller bottles by incubating for 15 minutes at 37° C. in a Tris-EDTA solution (10 mM Tris, 100 mM NaCl, 1 mM EDTA, pH=7.4). The cell suspension from each roller bottle was decanted into tared centrifuge tubes and kept on ice. An aliquot of each cell suspension was generally taken for cell counting. Cells were centrifuged at 3000×G for 5 min at 2°–4° C., washed with PBS and recentrifuged. The supernatant was decanted and the pellet weighed to determine the wet weight of cells. Cells were washed a final time in 40 vol 5 mM Tris-HCl, 5 mM EDTA, pH=7.7, and centrifuged at 40,000×G for 10 minutes. Cells were homogenized in 10 mL of 50 mM Tris-HCl, 5 mM EDTA (pH=7.4) and diluted to 40 mL/tube. Homogenates were centrifuged at 40,000×G for 10 minutes. The supernatant was decanted and the pellets rehomogenized in 50 mM Tris-HCl (pH=7.4) and centrifuged as before. The supernatant was decanted and the homogenate resuspended in 6.25 volumes (per gram wet weight) of 50 mM Tris-HCl and aliquots of the pooled homogenates frozen in liquid N$_2$ and stored at −70° C. until the time of assay. Rat submaxillary glands were used for α-1A receptors and were prepared essentially as described (Michel, A. D., Loury, D. N. and Whiting, R. L., Brit. J. Pharmacol. 98: 83–889 (1989).

Receptor binding assays for α-1 receptors were performed essentially as described by Greengrass and Bremner (Eur. J. Pharmacol. 55: 323–326 (1979)). Briefly, plastic Bioblocks™ (DBM Scientific, Valencia, Calif.) were incubated at 25° C. for 50 minutes with 500 µL of membrane homogenate (diluted with an additional 96 volumes [for cloned receptors, 12 volumes for submaxillary gland] in 50 mM Tris-HCl buffer (pH=7.7 at the time of assay), 450 µL of [³H]prazosin (0.2 mM final concentration, 75–85 Ci/mmole, DuPont-NEN Corp., Boston, Mass.) and 50 µL of either water (for total binding) or 10 µM phentolamine (final concentration, for non-specific binding). Following equilibration, bound radioligand was separated from free on GF/B filters (presoaked in 0.5% polyethyleneimine) using either a Brandel or Packard cell harvester. Radioactivity was determined by standard liquid scintillation techniques. Data were analyzed as previously described (Hancock, A. A., Kyncl, J. J., Martin, Y. C. and DeBernardis, J. F., J. Receptor Res. 8: 23–46 (1988)).

Canine prostate strips were used in vitro as previously described (Hieble, J. P., Boyce, A. J. and Caine, M., Fed. Proc., 45: 2609–2614 (1986)), to determine antagonist potencies against phenylephrine-induced contractions.

The results are shown in Table 1. The results show that the compounds of the invention bind to the α-1 adrenoceptor and show varying degrees of specificity for the α-1a receptor.

TABLE 1

In Vitro Data for Binding to α-1 Adrenoceptors

| Ex. No. | α-1A (Rat) (nM) | α-1b (Hamster) (nM) | α-1a (Bovine) (nM) | α-1d (Rat) (nM) |
|---|---|---|---|---|
| 1 | 1.012 | 1.84 | 0.212 | 0.893 |
| 2 | 0.847 | 1.28 | 0.182 | 0.707 |
| 3 | 2.468 | 3.65 | 0.443 | 2.381 |
| 4 | 3.704 | 3.803 | 1.489 | 2.681 |
| 5 | 1.392 | 1.631 | 0.268 | 0.919 |
| 6 | 16.588 | 11.806 | 2.149 | 15.92 |
| 7 | 14.912 | 14.186 | 2.812 | 55.718 |
| 8 | 0.481 | 1.015 | 0.203 | 0.517 |
| 9 | 0.845 | 2.273 | 0.19 | 1.155 |
| 10 | 0.666 | 10.601 | 0.149 | 3.384 |
| 11 | 0.57 | 2.708 | 0.042 | 0.584 |
| 12 | 1.891 | 1.038 | 0.501 | 1.132 |
| 13 | 0.971 | 1.982 | 0.254 | 0.97 |
| 14 | 0.318 | 1.936 | 0.086 | 2.051 |
| 15 | 1.341 | 2.48 | 0.239 | 1.96 |
| 16 | 8.027 | 15.407 | 1.225 | 2.715 |
| 17 | 1.377 | 4.952 | 0.318 | 1.12 |
| 18 | 1.704 | 17.385 | 0.579 | 5.66 |
| 19 | 0.371 | 1.4 | 0.048 | 0.814 |
| 20 | 2.731 | 16.279 | 0.425 | 2.863 |
| 21 | 1.19 | 3.31 | 0.472 | 1.995 |
| 22 | 2.732 | 6.471 | 0.939 | 2.153 |
| 23 | 0.604 | 1.017 | 0.052 | 0.711 |
| 24 | 1.414 | 3.103 | 0.311 | 1.783 |
| 25 | 0.931 | 1.622 | 0.199 | 0.952 |
| 26 | 0.407 | 1.326 | 0.089 | 1.333 |
| 27 | 4.435 | 10.576 | | 2.872 |
| 28 | 43.665 | 66.695 | 10.098 | 42.764 |
| 29 | 3.437 | 9.292 | 0.978 | 2.88 |
| 30 | 1.205 | 2.587 | 0.483 | 1.671 |
| 31 | 0.302 | 0.426 | 0.124 | 0.599 |
| 32 | 7.773 | 11.349 | 0.139 | 4.403 |
| 33 | 1.349 | 24.279 | | 16.595 |
| 34 | 1.275 | 4.285 | | 2.839 |
| 35 | 47.195 | 97.372 | | 36.631 |
| 36 | 7.576 | 11.165 | | 3.378 |
| 37 | 0.021 | 0.567 | | 0.159 |
| 38 | 0.097 | 0.341 | | 0.105 |
| 39 | 0.28 | 6.33 | | 1.401 |
| 42 | 0.277 | 16.007 | | 7.048 |
| 44 | 7.576 | 11.165 | | 3.378 |
| 46 | .115 | .699 | .058 | .362 |
| 47 | 1.345 | 2.349 | .273 | .722 |
| 48 | 6.243 | 19.411 | 1.265 | 22.539 |
| 49 | 1.097 | 3.349 | .493 | 1.387 |
| 50 | .123 | 1.082 | .079 | .771 |
| 51 | 2.426 | 8.51 | .239 | 4.688 |
| 52 | 1.878 | 20.477 | .542 | 12.057 |
| 53 | .908 | 2.386 | .259 | .43 |
| 54 | .28 | 1.371 | .073 | .865 |
| 55 | 2.808 | 11.908 | .482 | 12.604 |
| 56 | 2.078 | 54.925 | .542 | 46.465 |
| 57 | 2.217 | 7.564 | .477 | 4.125 |
| 58 | .634 | 3.592 | .224 | 3.137 |
| 59 | 11.07 | 28.623 | 2.364 | 12.139 |
| 60 | 1.477 | 3.372 | .23 | 1.377 |
| 61 | 6.962 | 10.808 | 2.003 | 2.678 |
| 62 | .967 | 2.136 | .14 | 2.457 |
| 63 | .807 | 4.73 | .337 | 2.242 |
| 64 | 1.095 | 7.147 | .242 | 1.451 |
| 65 | .413 | 2.312 | .12 | 1.502 |
| 66 | 1.071 | 9.504 | .242 | 2.231 |
| 67 | .161 | 1.198 | .064 | .982 |
| 68 | 1.384 | 4.073 | .138 | .73 |
| 69 | .275 | 1.645 | .056 | .774 |
| 70 | 12.991 | 26.977 | 3.792 | 11.079 |
| 71 | .48 | 3.881 | .102 | 1.028 |
| 72 | 2.11 | 10.263 | .328 | 3.33 |
| 73 | 2.788 | 8.384 | .343 | 2.754 |
| 74 | .912 | 3.331 | .262 | 1.204 |
| 75 | .198 | .84 | .161 | .415 |
| 76 | .836 | 1.315 | .509 | 1.278 |
| 77 | .448 | 1.987 | .106 | .976 |
| 78 | .612 | 5.756 | .333 | 4.565 |
| 79 | .666 | 1.164 | .204 | .619 |

TABLE 1-continued

In Vitro Data for Binding to α-1 Adrenoceptors

| Ex. No. | α-1A (Rat) (nM) | α-1b (Hamster) (nM) | α-1a (Bovine) (nM) | α-1d (Rat) (nM) |
|---|---|---|---|---|
| 80 | .091 | 1.316 | .021 | .892 |
| 81 | .037 | .662 | .017 | .676 |
| 83 | 1.44 | 17.896 | .236 | 6.388 |
| 84 | .491 | .337 | .101 | .396 |
| 85 | .051 | .09 | .087 | .218 |
| 86 | 32.507 | 127.341 | 6.305 | 26.998 |
| 87 | 9.217 | 12.588 | 3.111 | 5.496 |
| 88 | 26.013 | 30.814 | 5.132 | 17.437 |

Functional Antagonism at α-1 Adrenoceptors

Functional assays indicative of pharmacologically defined α-1 adrenoceptors were used to further characterize compounds. Inhibition of phenylephrine (PE)-induced contraction of canine prostate smooth muscle can be correlated with α-1A adrenoceptor activation. Inhibition of PE-induced contraction of rat spleen is representative of α-1B adrenoceptor antagonism and inhibition of PE-induced contraction of rat vas deferens correlates with α-1A adrenoceptor antagonism (R. P. Burt, C. R. Chapple and I. Marshall, Br. *J. Pharmacol.* 107: P324 (1992)). For each of these models, agonist dose response curves were repeated against increasing concentrations of test agent to derive a Schild plot [log ($EC_{50}$-1) against log (molarity of test agent)] to determine the $pA_2$. Data for prazosin, terazosin and doxazosin actually demonstrate a more potent effect on spleen smooth muscle by approximately an order of magnitude.

Canine prostate strips were used in vitro as previously described (Hieble, J. P., Boyce, A. J. and Caine, M., *Fed. Proc.*, 45: 2609–2614 (1986)), to determine antagonist potencies against phenylephrine-induced contractions.

The results are shown in Tables 2a and 2b. The results show that the compounds of the invention exhibit functional antagonism of α-1 adrenoceptors.

TABLE 2a

In Vitro Data for Functional Antagonism at α-1 Adrenoceptors

| Ex. No. | $pA_2$ Rat Vas Deferens [α-1A] | $pA_2$ Rat Spleen [α-1B] | $pA_2$ Dog Prostate [α-1A] |
|---|---|---|---|
| 1 | 8.49 | 8 | 9.29 |
| 2 | 8.4 | 8.16 | 9.16 |
| 3 | 8.33 | 7.91 | 8.68 |
| 5 | 8.19 | 8.36 | 9.16 |
| 8 | 8.52 | 8.26 | 9.34 |
| 9 | 8.62 | 8.05 | 9.39 |
| 10 | 8.04 | 6.89 | 8.97 |
| 11 | 8.69 | | 8.92 |
| 12 | 8.07 | 8.17 | 7.67 |
| 13 | 8.12 | 8.37 | 9.07 |
| 33 | 8.95 | 7.69 | 8.87 |
| 39 | 8.53 | 7.52 | |
| 42 | 8.24 | 7.4 | 9.58 |
| 77 | 9.32 | 8.53 | 9.4 |
| 80 | 9.05 | 7.93 | 9.2 |
| 81 | 8.9 | 8.15 | 9.45 |
| 83 | 8.07 | 6.92 | 7.95 |
| prazosin | 8.78 | 9.51 | 7.59 |
| terazosin | 8.04 | 8.6 | 7.44 |
| doxazosin | 8.69 | 9.51 | 7.59 |

TABLE 2b

In Vitro Data for Functional Antagonism at α-1 Adrenoceptors

| Ex. No. | $pA_2$ Dog Prostate [α-1A] | Ex. No. | $pA_2$ Dog Prostate [α-1A] |
|---|---|---|---|
| 4 | 7.91 | 53 | 8.71 |
| 6 | 7.32 | 54 | 9.05 |
| 7 | 7.62 | 55 | 8.31 |
| 14 | 9.01 | 56 | 8.78 |
| 15 | 8.27 | 57 | 8.14 |
| 16 | 7.91 | 58 | 8.9 |
| 17 | 8.94 | 59 | 8.48 |
| 18 | 8.38 | 60 | 9.15 |
| 19 | 8.3 | 61 | 8.64 |
| 20 | 8.83 | 62 | 8.59 |
| 21 | 7.88 | 63 | 8.87 |
| 22 | 8.82 | 64 | 8.81 |
| 23 | 8.32 | 65 | 8.63 |
| 24 | 8.89 | 66 | 8.94 |
| 25 | 9.17 | 67 | 8.33 |
| 26 | 9.23 | 68 | 8.28 |
| 27 | 8.63 | 69 | 9.24 |
| 28 | 8.32 | 70 | 8.95 |
| 29 | 8.91 | 71 | 8.45 |
| 30 | 8.94 | 72 | 8.57 |
| 31 | 8.63 | 73 | 8.91 |
| 32 | 7.47 | 74 | 8.77 |
| 34 | 8.98 | 75 | 9.18 |
| 35 | 7.06 | 76 | 8.73 |
| 36 | 8.27 | 77 | 9.4 |
| 37 | 9.62 | 78 | 8.03 |
| 38 | 9.64 | 79 | 9.01 |
| 44 | 8.27 | 80 | 9.2 |
| 46 | 9.24 | 81 | 9.45 |
| 47 | 8.79 | 83 | 7.95 |
| 48 | 8.19 | 84 | 8.09 |
| 49 | 7.92 | 85 | 8.55 |
| 50 | 9.2 | 87 | 8.89 |
| 51 | 7.85 | 88 | 8.73 |

In Vivo Determination of Intraurethral Pressure (IUP) in Canines

The intraurethral pressure (IUP) model in aged canines is an accepted model of measuring the effect of prostate smooth muscle contraction on urethral tone. Canines also have an enclosed prostate covering the urethral shaft thus providing an anatomical correlate with humans.

Beagle dogs (Marshall Farms) greater that 2 years of age and weighing between 12 and 15 kg were pre-anesthetized with thiopental sodium 15 mg/kg i.v. (Pentothal™, Abbott) and then placed under general anesthesia (isoflurane). A 7F Swan-Ganz balloon catheter (Multiflex-list no. 41224-01, Abbott) was lubricated with a water soluble jelly, inserted into the urethral orifice and advanced approximately 40 cm in male dogs (considerably less in females) until the balloon tip was placed well inside the bladder. The balloon was then inflated with 1 mL of room air and the catheter slowly withdrawn just past the first resistance that is felt at the bladder neck. Preliminary experiments in which dogs were sacrificed after such placement confirmed that this technique results in consistent positioning of the balloon within the prostatic urethra in males or the corresponding location in females. The balloon port of the catheter was connected to a Gould Statham P23Dd pressure transducer interfaced to a computerized data acquisition system (Modular Instruments, Inc., Malvern, Pa.) for the measurement of intraurethral pressure (IUP).

Dogs were then treated with propranolol to block the β-adrenoceptor agonist effects of test agonists. Dose-response curves of the intraurethral pressor effect of epinephrine (EPI) were obtained before and after each of up to 3 increasing doses of a test antagonist (i.v.). Fifteen minutes was allowed after each antagonist dose for equilibration before the next agonist dose-response was initiated. The increase in IUP caused by a given agonist dose was allowed to return to baseline before the next dose was given. The estimated antagonist dissociation constant (in vivo pseudo $pA_2$) was determined by Schild analysis (Brune, et al., Drug Development Research (1995) in press).

The results are shown in Table 3. The results indicate that the compounds of the invention inhibit EPI induced increases in IUP.

TABLE 3

Inhibition of EPI Induced Increase in Canine IUP

| Example | Canine IUP pseudo $pA_2$ |
|---|---|
| 1 | 8.37 |
| 3 | 8.22 |
| 8 | 8.3 |
| 9 | 8.12 |
| 10 | 8.0 |
| 11 | 8.06 |
| 12 | 7.36 |
| 13 | 8.82 |
| prazosin | 7.88 |
| terazosin | 6.91 |
| doxazosin | 6.90 |

Spontaneously Hypertensive Rat (SHR) Model

The SHR model historically has been used as a predictor for the hypotensive effects of α-1 adrenoceptor antagonists. Male spontaneously hypertensive rats were anesthetized and the left femoral artery and vein catheterized for the measurement of mean arterial pressure (MAP) and drug administration respectively. The arterial catheter was connected to a Gould Statham p23ID transducer and the pressure waveform was recorded. MAP (mm Hg) and heart rate (HR, beats/min.) were determined on-line using a BUXCO Cardiovascular Analyzer. After a 30 minute pre-dose control period, each rat was given one dose of a test antagonist i.v. and the MAP and HR were monitored for an additional 2.5 hours. The area under the hypotensive response curve up to 60 minutes post dosing ($T_{60}$ AUC) was determined using a trapezoidal rule integration of the percent change from control arterial pressure dataset.

The results are shown in Table 4. The results show that the compounds of the invention are weakly hypotensive.

TABLE 4

Spontaneously Hypertensive Rat (SHR) Assay

| Example | SHR pseudo $pA_2$ |
|---|---|
| 1 | 6.34 |
| 2 | 6.08 |
| 3 | 5.29 |
| 5 | 5.9 |
| 8 | 6.34 |
| 9 | 6 |
| 10 | 4.8 |
| 12 | 5.22 |
| 13 | 5.44 |
| prazosin | 7.4 |
| terazosin | 6.59 |
| doxazosin | 6.74 |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intraperitoneally, topically (as by powders, ointments, or drops), bucally, or as an oral or nasal spray. The term "parental" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a)

fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 0.01 to about 50, more preferably of about 0.05 to about 5 mg of active compound per kilogram of body weight per day are administered orally to a mammalian patient. If desired, the effective daily dose may be divided into multiple doses for purposes of administration, e.g. two to four separate doses per day.

While the compounds of the invention can be administered as the sole active pharmaceutical agent, they can also be used in combination with a 5-α reductase inhibitor. A particularly preferred 5-α reductase inhibitor for use in coadministration with compounds of the present invention is the compound having the generic name finasteride.

Methods for preparing the compounds of the invention are shown in Schemes I–VI. In the following Schemes, $R_1$ and $R_2$ are independently hydrogen, alkoxy, hydroxy, alkyl, halo, carboxy, or alkoxycarbonyl.

Scheme I illustrates the general procedure for the preparation of the compounds of the invention. Compound 1, prepared by the procedures described in U.S. Pat. No. 4,618,683, which is incorporated herein by reference, is reacted with chloroacetonitrile under mildly basic conditions (for example, diisopropylethylamine, triethylamine and the like) to afford the cyanomethyl compound 2. The nitrile is dissolved in an inert solvent (for example, THF, ether and the like) and treated with a reducing agent (for example, lithium aluminum hydride, diborane or catalytic hydrogenation and the like) to give the ethylene diamine compound 3. The diamine is reacted with the isocyanate 4 of the aromatic compound U, prepared from the aromatic amine by treatment with phosgene or triphosgene, to give the pyrimidine dione 5.

Alternatively as shown in Scheme II, the diamine can by prepared by taking diester 6, prepared by the procedures described in U.S. Pat. No. 5,049,564, which is incorporated herein by reference, in an inert solvent (for example, THF or ether and the like) and reducing the diester with a reducing agent (for example, lithium aluminum hydride or diborane and the like) to give the diol 7. The diol is reacted with an appropriate reagent to form leaving groups (for example, a mesylate or tosylate and the like) giving compound 8. Treatment of compound 8 with the appropriate diamine $(H_2N-(CH_2)_n-NH_2$ or synthon) with heating gives the pyrrolidine amine 9. Compound 9 can be further elaborated by the procedures described in Scheme I to give the final compound 10.

The compounds of the invention can also be prepared by the procedures illustrated in Scheme III. Compound 4a is reacted with a haloalkyl isocyanate (for example, 2-chloroethyl isocyanate) by the procedures described in Eur. J. Med. Chem. 28: 499 (1993), which is incorporated herein by reference, to give haloalkyl urea 11. Compound 1, as previously described in Scheme I, is reacted with compound 11 to give the final product 5.

The preparation of chiral cis intermediates is shown in Scheme IV. Dihydronaphthylene-1-carboxylic acid 12 is esterified (for example, using diazomethane or alcohol with a trace of sulfuric acid) to give compound 13. Treatment of the α,β-unsaturated ester with lithium cyanide in DMF and acetic acid affords the cyano compound 14. The nitrile ester is hydrolyzed (for example, using KOH in ethanol/water) to give the dicarboxylic acid 15. Treatment of the diacid with acetic anhydride under reflux affords the cyclic anhydrides 16a and 16b. The anhydrides are reacted with optically active (S)-(-)-α-methylbenzylamine to give both the (3aR, 9bR)-compound 18 and the (3aS,9bS)-compound 17 as a mixture of imides separable by crystallization. Compounds 17 and 18 are reduced (for example, with diborane) to give the corresponding N-substituted pyrrolidine compounds 19 and 20. Catalytic hydrogenation affords chiral intermediates 21 and 22. These pyrrolidines can be further elaborated by the procedures described in Schemes I and III to give the final products.

A preferred embodiment is shown in Scheme V. Compound 23 wherein R is a carboxy protecting group is reacted with 2-chloroethyl isocyanate to give urea 24. Compound 24 is reacted with compound 25 in a solvent such as DMSO in the presence of a non-nucleophilic base such as diisopropylethylamine to give the ring closed coupled product 27.

Another preferred embodiment in shown in Scheme VI. The aromatic carboxy-protected amine 28 is reacted with triphosgene to give isocyanate 29. The isocyanate is reacted with amine 30, prepared by the procedure described in Scheme I or II, to cyclize and couple in one step to give compound 31.

Scheme I

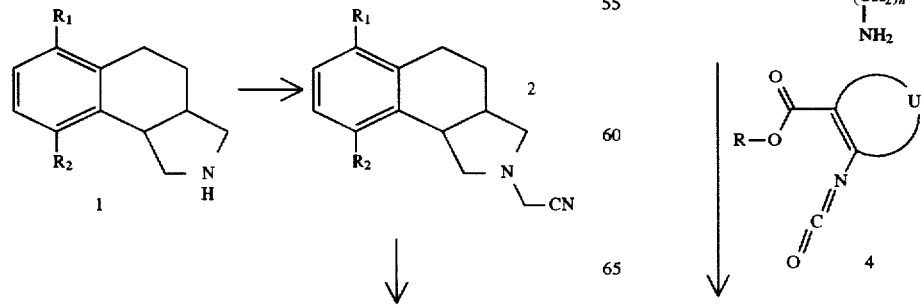

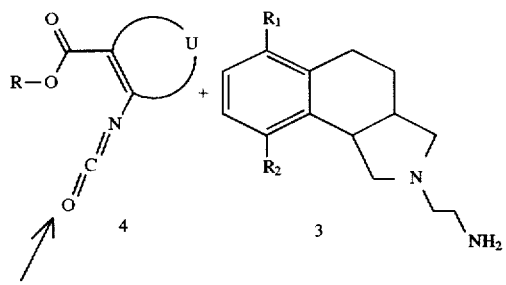

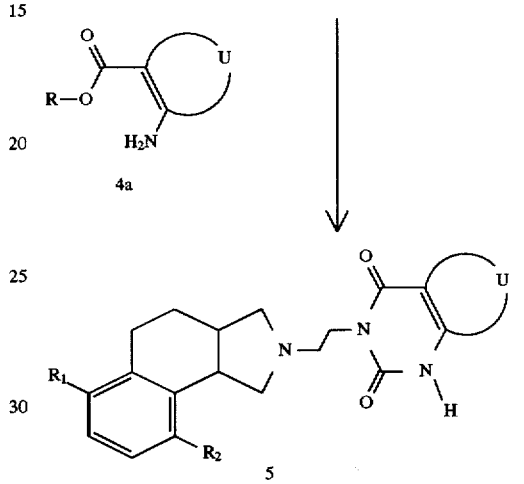

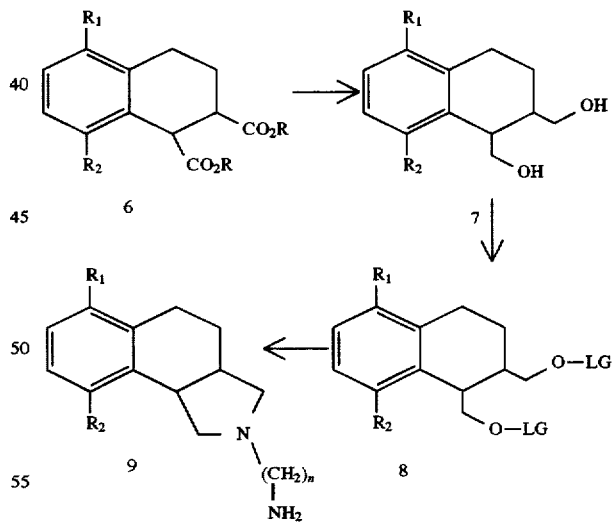

33
-continued
Scheme II
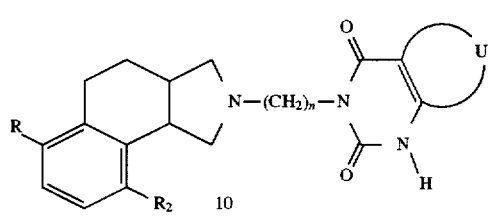
10
34
-continued
Scheme III
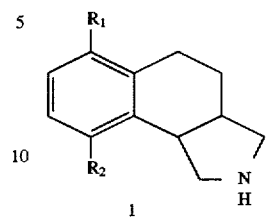 + 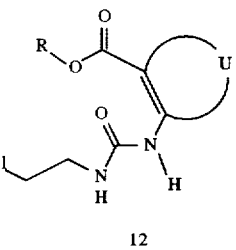
1
12
Scheme III
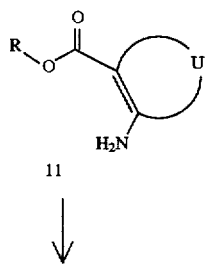
11
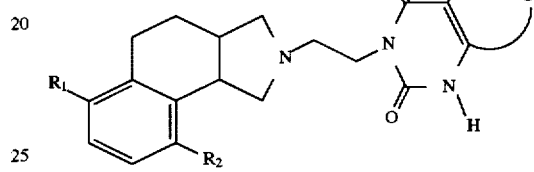
5
Scheme IV
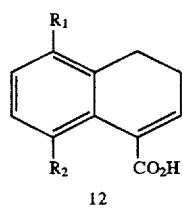  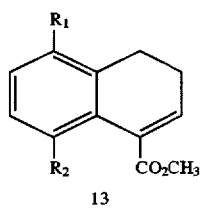  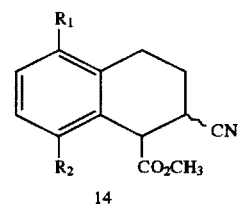
12
13
14
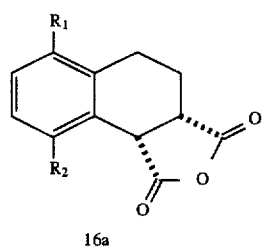 + 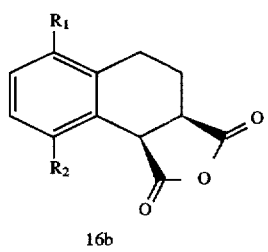  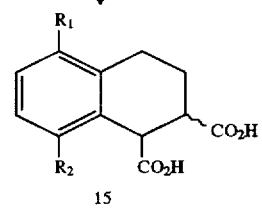
16a
16b
15
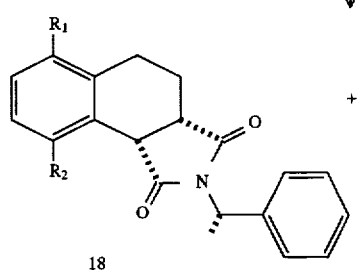 + 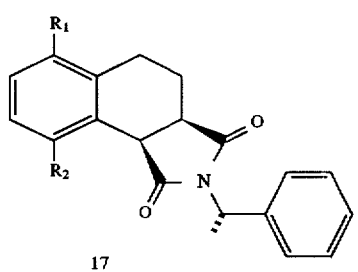
18
17

-continued
Scheme IV
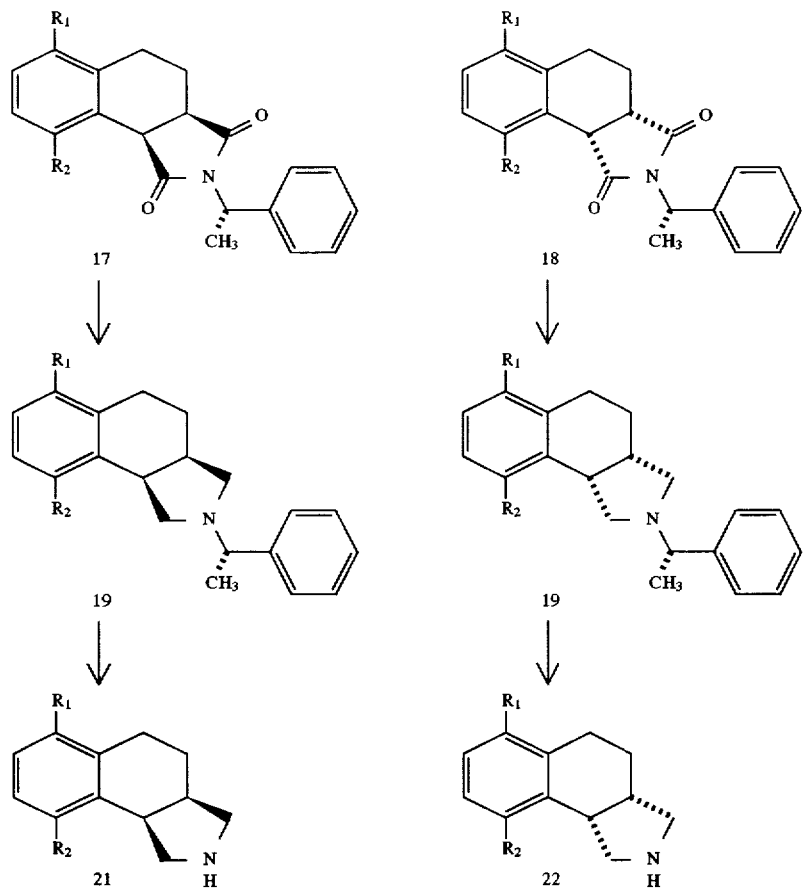
Scheme V
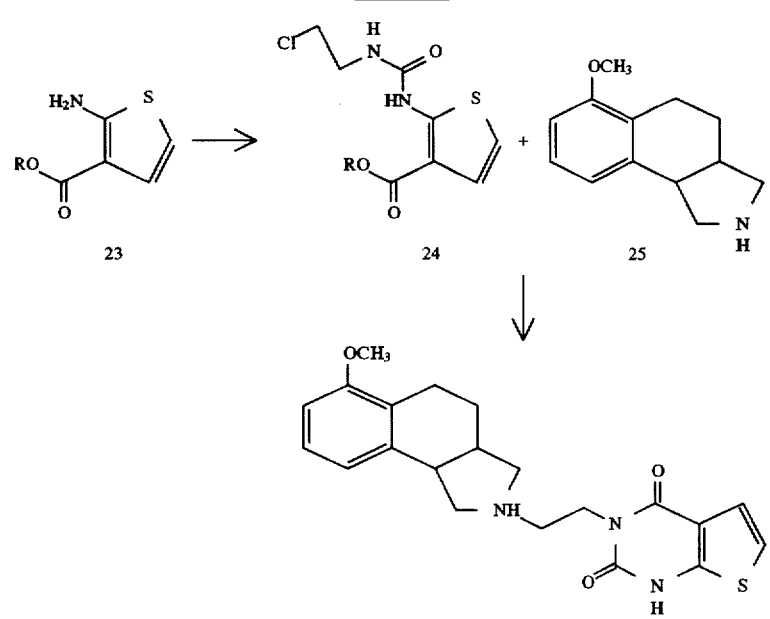

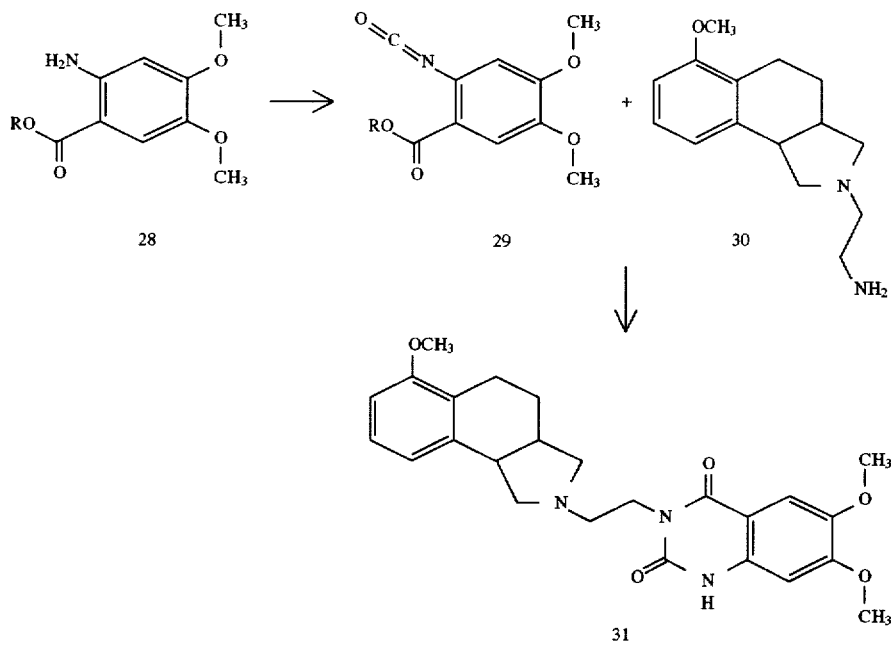

Scheme VI

The forgoing may be better understood by reference to the following examples which are provided for illustration and not intended to limit the scope of the inventive concept.

The following abbreviations were used: BH$_3$·DMS for borane dimethylsulfide complex, DMF for dimethylformamide, DMSO for dimethylsulfoxide, Et$_3$N for triethylamine, Et$_2$O for diethyl ether, EtOAc for ethyl acetate, EtOH for ethanol, KOtBu for potassium tert-butoxide, LDA for lithium diisopropylamide, MeOH for methanol, NaOEt for sodium ethoxide, iPrOH for isopropyl alcohol and THF for tetrahydrofuran.

EXAMPLE 1

3-[2-(cis-9-Methoxy-2,3,3a,4,5,9b-hexahydro-[1H]-benz[e]isoindol-1-yl)ethyl]-[1H,3H]-quinazoline-2,4(1H,3H)-dione hydrochloride

EXAMPLE 1A cis-6-Methoxy-(2-cyanomethyl)-2,3,3a,4,5,9b-hexahydro-[1H]benz[e]isoindole Cis-6-methoxy—2,3,3a,4,5,9b-hexahydro-[1H]benz[e]isoindole (2.39 g, 10 mmol), prepared by the porcedures described in U.S. Pat. No. 4,618,683, which is incorporated herein by reference, and chioroacetonitrile (0.67 mL, 10.6 mmol) were combined in 10 mL acetonitrile and 5 mL ethyeiisopropylamine and heated at 70° C. for 1 h. The reaction was quenched in 5% NaHCO$_3$, and extracted with ethyl acetate (2×). The organic extracts were washed with water (2×) and brine (1×), dried (Na$_2$SO$_4$) and evaporated toyield 2.20 g of the title compound as an off white solid (90%). $^1$H NMR (300 MHz, CDCl$_3$) δ 1.60 (m, 2H), 1.80 (m, 1H), 2.58 (m, 3H), 2.77 (m, 1H), 3.23 (m, 2H), 3.48 (1, 1H), 3.64 (s, 2H), 3.81 (s, 3H), 6.70 (d, 1H), 6.74 (d, 1h), 7.12 (t, 1H).

EXAMPLE 1B cis-6-Methoxy-(2-(2-aminoethyl))-2,3,3a,4,5,9b-hexahydro-[1H]benz[e]isoindole LiAlH$_4$ (2.40 g, 62 mmol) was suspended in THF (100 mL) and coiled to 0° C. The compound resulting from Example 1A (2.20 g, 9.0 mmol) was dissolved in THF (10 mL) and added dropwsie to the above LiAlH$_4$ suspension. The reaction was then stirred at room temperature for 1.5 hours, quenched by addition of H$_2$O (2.2 mL), 15% NaOH (2.2 mL), and H$_2$O (6.6 mL), filtered through celite, washing with several potions of hot THF, and the solvent evaporated toyield the title compound (2.15 g, 93%) as a colorless oil. $^1$H NMR (300 MHz, CDCl$_3$) δ 1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H), 3.40 (m, 1H), 3.80 (s, 3H), 6.67 (d, 1h), 6.75 (d, 1H), 7.11 (t, 1H).

EXAMPLE 1C

3-[2-(cis-6-Methoxy-2,3,3a,4,5,9b-hexahydro-[1H]-benz[e]isoindol-1-yl)ethyl]-[1H,3H]-quinazoline-2,4(1H,3H)-dione hydrochloride 2-Carboethoxy-phenylisocyanate (0.20 g, 1.0 mmol) was prepared by the reaction of 2-carboethoxyaniline and triphosgene in toluene at reflux, followed by removing the solvent in vacuo. The isocyanate and the compound resulting from Example 1B (0.24 g, 1.0 mmol) were combined in 40 mL of toluene and heated at reflux for 3 hours. The product was then partitioned between 5% NaHCO$_3$ and hot ethyl acetate, and the organic phase was dried (K$_2$CO$_3$) and evaporated. The resulting product was converted to its hydrochloride salt and recrystallized from ethanol-ether to yield 0.12 g of the title compound as a white solid. $^1$H NMR (300 MHz, DMSO-d$_6$) δ 7.92 (d, 1H), 7.65 (t, 1H), 7.12-7.27 (m, 2H), 7.08 (t, 1H), 6.72 (dd, 2H), 4.02 (t, 2H), 3.73 (s, 3H), 3.12-3.3 (m, 3H), 2.52-2.65 (m, 3H), 2.38-2.48 (m, 2H), 2.1-2.3 (m, 2H), 1.57-1.68 (m, 1H), 1.37-1.5 (m, 1H). Anal calcd for C$_{23}$H$_{25}$N$_3$O$_3$·HCl·H$_2$O: C, 61.95; H, 6.33; N, 9.42. Found: C, 61.94; H, 6.10; N, 9.18.

EXAMPLE 2

3-[2-(cis-6-Methoxy-2,3,3a,4,5,9b-hexahydro-[1H]-benz[e]isoindol-1-yl)ethyl]-7-methylthieno[3,2-d]pyrimidine-2,4 (1H,3H)-dione hydrochloride 2-Carbomethoxy-4methyl-thiophene-3-isocyanate (0.22 g, 1.1 mmol), prepared from the amine and triphosgene by the procedure described in Example 1C, and the compound resulting from Example 1B (0.24 g, 1.0 mmol) were treated by the procedures described in Example 1C to yield 0.12 g of the title compound as a white solid. m.p. 255°–257° C. $^1$H NMR (300 MHz, CDCl$_3$) of the free base δ 1.46–1.58 (m, 1H), 1.69–1.81 (m, 1H), 2.20–2.35 (m, 2H), 2.28 (d, 3H), 2.48–2.60 (m, 2H), 2.64–2.90 (m, 3H), 3.36–3.50 (m, 3H), 3.81 (s, 3H), 4.21 (t, 2H), 6.67 (d, 1H), 6.74 (d, 1H), 7.10 (t, 1H), 7.31 (d, 1H). MS (DCI/NH$_3$) m/e 412 (M+H)$^+$. Anal calcd for C$_{22}$H$_{25}$N$_3$O$_3$S·HCl·0.5 H$_2$O: C, 57.82; H, 5.96; N, 9.19. Found: C, 58.01; H, 5.95; N, 9.08.

EXAMPLE 3

3-[2-(cis-6-Methoxy-2,3,3a,4,5,9b-hexahydro-[1H]-benz[e] isoindol-1-yl)ethyl]-thieno[2,3-d]pyrimidine-2,4(1H,3H)-dione hydrochloride 2-Amino-3-carboethoxythiophene, prepared by the method of Gewald, *Chem. Ber.* 98: 3571 (1965), was treated with 2-chloroethyl-isocyanate by the procedures described by Romeo, et al in *Eur. J. Med. Chem.*, 28: 499–504 (1993). The resulting urea (0.67 g, 2.4 mmol) and cis-6-methoxy-2,3,3a,4,5,9b-hexahydro-[1H]-benz[e]isoindole (0.45 g, 2.2 mmol), prepared by the procedures described in U.S. Pat. No. 4,618,683, which is incorporated herein by reference, and 0.4 mL diisopropylethylamine in DMSO (1 mL) were heated at 100° C. for 1.5 hours. The reaction was quenched in H$_2$O and extracted with ethyl acetate. The combined organic extracts were dried and concentrated in vacuo resulting in a urea ester intermediate which was treated with 0.25 mL 1.0M KOtBu in ethanol (2 mL) at reflux for 0.5 hours. After purification by column chromatography eluting with 95:5 ethyl acetate-ethanol and conversion to its HCl salt the title compound (0.30 g, 54%) was obtained as a white solid. m.p. 192°–194° C. $^1$H NMR (500MHz, DMSO-d$_6$) δ 1.53–1.63 (m, 1H), 1.75–1.82 (m, 1H), 238–2.55 (m, 1H), 2.60–2.68 (m, 1H), 2.68–2.78 (m, 1H), 2.91–3.05 (m, 1H), 3.33–3.54 (m, 3H), 3.71–3.86 (m, 1H), 3.78 (s, 3H), 3.93–4.24 (m, 4H), 6.75 (d, 1H), 6.83 (d, 1H), 7.11–7.20 (m, 3H). MS (DCI/NH$_3$) m/e 398 (M+H)$^+$. Anal calcd for C$_{21}$H$_{23}$N$_3$O$_3$S·HCl·0.25H$_2$O: C, 57.53; H, 5.63; N, 9.58. Found: C, 57.48; H, 5.68; N, 9.43.

EXAMPLE 4

3-[2-(cis-6-Methoxy-2,3,3a,4,5,9b-hexahydro-[1H]-benz[e] isoindol-1-yl)ethyl]-5-methylthieno[2,3-d]pyrimidine-2,4 (1H,3H)-dione hydrochloride 2-Amino-3-carboethoxy-4methylthiophene was treated with 2-chloroethyl-isocyanate by the procedures described in Example 3. The resulting urea (0.35 g, 1.2 mmol) and cis-6-methoxy-2,3,3a,4,5,9b-hexahydro[1H]-benz[e] isoindole (0.23 g, 1.1 mmol) were treated by the procedures described in Example 3 to afford the title compound (0.11 g, 41%) was obtained as a white solid. m.p. 179°–181° C. $^1$H NMR (500 MHz, DMSO-d$_6$) δ 1.40–1.48 (m, 1H), 1.60–1.67 (m, 1H), 2.12–2.19 (m, 1H), 2.24 (dd, 1H), 2.34 (s, 3H), 2.41–2.49 (m, 2H), 2.52–2.63 (m, 3H), 3.13 (t, 1H), 3.23–3.30 (m, 2H), 3.75 (s, 3H), 3.94 (t, 2H), 6.64 (s, 1H), 6.72 (d, 1H), 6.74 (d, 1H), 7.08 (t, 1H). MS (DCI/NH$_3$) m/e 412 (M+H)$^+$. Anal calcd for C$_{22}$H$_{25}$N$_3$O$_3$S·HCl·2 H$_2$O: C, 54.59; H, 6.25; N, 8.68. Found: C, 54.30; H, 5.64; N, 8.47.

EXAMPLE 5

3-[2-(cis-6-Methoxy-2,3,3a,4,5,9b-hexahydro-[1H]-benz[e] isoindol-1-yl)ethyl]-thieno[3,2-d]pyrimidine-2,4(1H,3H)-dione hydrochloride 3-Amino-2-carboethoxythiophene was treated with 0.33 equivalent triphosgene by the procedures described in Example 1C. The resulting isocyanate (0.21 g, 1.15 mmol) and the compound resulting from Example 1B (0.24 g, 1.0 mmol) were treated by the procedures described in Example 1C to yield the title compound (0.12 g, 28%) as a white solid. m.p. 190°–192° C. $^1$H NMR (300MHz, CDCl$_3$) δ 1.55–1.68 (m, 1H), 1.85–1.98 (m, 1H), 2.53–2.65 (m, 1H), 2.70–2.83 (m, 2H), 2.83–2.96 (m, 2H), 3.39–3.50 (m, 2H), 3.67 (q, 1H), 3.82 (s, 3H), 4.08–4.30 (m, 2H), 4.37 (t, 2H), 6.74 (t, 2H), 6.84 (d, 1H), 7.15 (t, 1H), 7.62 (d, 1H), 8.17 (bs, 1H). MS (DCI/NH$_3$) m/e 398 (M+H)$^+$. Anal calcd for C$_{21}$H$_{23}$N$_3$O$_3$S·HCl·0.75 H$_2$O: C, 56.37; H, 5.74; N, 9.39. Found: C, 56.32; H, 5.86; N, 8.90.

EXAMPLE 6

3-[2-(cis-6-Methoxy-2,3,3a,4,5,9b-hexahydro-[1H]-benz[e] isoindol-1-yl)ethyl]-5-phenyl-thieno[2,3-d]pyrimidine-2,4 (1H,3H)-dione hydrochloride 2-Amino-3-Carboethoxy-4-phenylthiophene, prepared by the procedure of Gewald, et al., *Chem. Ber.* 94: 99 (1966), was treated with 2-chloroethylisocyanate by the procedures described by Romeo, et al in *Eur. J. Med. Chem.*, 28: 499–504 (1993). The resulting urea (0.59 g, 1.65 mmol) and cis-6-methoxy-2,3,3a,4,5,9b-[1H]-benz[e]isoindole (0.31 g, 1.5 mmol) were treated by the procedures described in Example 3 to yield the title compound (0.15 g, 42%) as a white solid. m.p. 176°–178° C. $^1$H NMR (400 MHz, DMSO-d$_6$) δ 1.49–1.58 (m, 1H), 1.79–1.86 (m, 1H), 2.39–2.47 (m, 1H), 2.54–2.62 (m, 1H), 2.65–2.73 (m, 1H), 2.76–2.93 (m, 1H), 3.12–3.52 (m, 4H), 3.55–3.65 (m, 1H), 3.71–3.83 (m, 1H), 3.75 (s, 3H), 4.05–4.14 (m, 2H), 6.72 (d, 1H), 6.79 (d, 1H), 7.12 (t, 1H), 7.32–7.39 (m, 3H), 7.41 (dd, 2H). MS (DCI/NH$_3$) m/e 474 (M+H)$^+$. Anal calcd for C$_{27}$H$_{27}$N$_3$O$_3$S·HCl·H$_2$O: C, 61.41; H, 5.73; N, 7.96. Found: C, 61.80; H, 5.83; N, 7.81.

EXAMPLE 7

3-[2-(cis-6-Methoxy-2,3,3a,4,5,9b-hexahydro-[1H]-benz[e] isoindol-1-yl)ethyl]-6-phenyl-thieno[2,3-d]pyrimidine-2,4 (1H,3H)-dione hydrochloride 2-Amino-3-Carboethoxy-5-phenylthiophene, prepared by the procedure of Gewald, et al., *Chem. Ber.*, 94: 99 (1966), was treated with 2-chloroethylisocyanate by the procedures described in *Eur. J. Med. Chem.*, 28: 499–504 (1993). The resulting urea (0.42 g, 1.45 mmol) and cis-6-methoxy-2,3, 3a,4,5,9b-[1H]-benz[e]isoindole (0.22 g, 1.1 mmol) were treated by the procedures described in Example 3 to yield the title compound (0.11 g, 42%) as a white solid. m.p. 248°–250° C. (dec.). $^1$H NMR (500 MHz, DMSO-d$_6$) δ 1.53–1.64 (m, 1H), 1.74–1.83 (m, 1H), 2.38–2.52 (m, 1H), 2.62–2.78 (m, 2H), 2.94–3.06 (m, 1H), 3.28–3.34 (m, 1H), 3.40–3.54 (m, 3H), 3.77 (s, 3H), 3.79–4.03 (m, 1H), 4.08–4.26 (m, 3H), 6.75 (bs, 1H), 6.83 (d, 1H), 7.16 (t, 1H), 7.32 (t, 1H), 7.42 (t, 2H), 7.61 (s, 1H), 7.67 (d, 2H). MS (DCI/NH$_3$) m/e 474 (M+H)$^+$. Anal calcd for C$_{27}$H$_{27}$N$_3$O$_3$S·HCl·0.5 H$_2$O: C, 62.48; H, 5.63; N, 8.10. Found: C, 62.39; H, 5.58; N, 8.04.

EXAMPLE 8

3-[2-(cis-6-Methoxy-2,3,3a,4,5,9b-hexahydro-[1H]-benz[e] isoindol-1-yl)ethyl]-thieno[3,4d]pyrimidine-2,4(1H,3H)-dione hydrochloride 3-Amino-4-carboethoxythiophene, prepared by the method of Baker, et al., *J. Org. Chem.*, 18: 138 (1953), was treated with 0.33 equivalent triphosgene. The resulting isocyanate (0.29 g, 1.6 mmol) and the compound resulting from Example 1B (0.30 g, 1.2 mmol) were treated by the procedure described in Example 1C to yield the title compound (0.15 g,45%) as a white solid. m.p. 205°–210° C. $^1$H NMR (300 MHz, CDCl$_3$) δ 1.54–1.88 (m, 1H), 1.82–1.94 (m, 1H), 2.52–2.65 (m, 1H), 2.71–2.86 (m, 4H), 3.25–3.38 (m, 2H), 3.66–3.79 (m, 1H), 3.83 (s, 3H), 3.98–4.18 (m, 2H), 4.29 (t, 2H), 6.55 (d, 1H), 6.71 (d, 1H), 6.77 (d, 1H), 7.13 (t, 1H), 8.10 (d, 1H). MS (DCI/NH$_3$) m/e 398 (M+H)$^+$. Anal calcd for C$_{21}$H$_{23}$N$_3$O$_3$S·HCl·1.5 H$_2$O: C, 54.72; H, 5.90; N, 9.12. Found: C, 54.89; H, 5;N, 8.73.

EXAMPLE 9

3-|2-(cis-6-Methoxy-2,3,3a,4,5,9b-hexahydro-|1H|-benz|e| isoindol-1-yl)ethyl|-8-methoxy-quinazoline-2,4(1H,3H)-dione hydrochloride 2-Methoxy-6-carboethoxyaniline was treated with 0.33 equivalent triphosgene. The resulting isocyanate (0.30 g, 1.1 mmol) and the compound resulting from Example 1B (0.25 g, 1.0 mmol) were treated by the procedures described in Example 1C to yield the title compound (0.15 g, 33%) as a white solid. m.p. 233°–235° C. $^1$H NMR (300 MHz, CDCl$_3$ of the free base δ 7.68 (dd, 1H), 7.08–7.2 (m, 3H), 6.75 (t, 2H), 4.42 (m, 2H), 4.1–4.28 (m, 2H), 3.98 (s, 3H), 3.82 (s, 3H), 3.68 (q, 1H), 3.41 (m, 2H), 2.7–2.98 (m, 4H), 2.51–2.63 (m, 1H), 1.88–1.98 (m, 1H), 1.52–1.68 (m, 1H). MS (DCI/NH$_3$) m/e 422 (M+H)$^+$. Anal calcd for C$_{24}$H$_{27}$N$_3$O$_4$·HCl·1.25 H$_2$O: C, 59.94; H, 5.83; N, 8.74. Found: C, 60.06; H, 5.74; N, 8.73.

EXAMPLE 10

3-[2-(cis-6-Methoxy-2,3,3a,4,5,9b-hexahydro-|1H|-benz|e| isoindol-1-yl)ethyl]-6,7-dimethoxy-quinazoline-2,4(1H, 3H)-dione hydrochloride 2-Carboethoxy-4,5-dimethoxyaniline was treated with 0.33 equivalent triphosgene. The resulting isocyanate (0.55 g, 2.2 mmol) and the compound resulting from Example 1B (0.49 g, 2.0 mmol) were treated by the procedures described in Example 1C to yield the title compound (0.60 g, 66%) as a white solid. $^1$H NMR (300 MHz, DMSO-d$_6$) δ 7.3 (d, 1H), 7.18 (t, 1H), 6.7–6.9 (m, 3H), 4.1–4.3 (m, 3H), 3.94.1 (m, 1H), 3.85 (s, 3H), 3.8 (s, 3H,), 3.7 (s, 3H), 3.4–3.58 (m, 4H), 2.92–3.6 (m, 2H), 2.6–2.85 (m, 2H), 1.73–1.88 (m, 1H), 1.52–1.68 (m, 1H). MS (DCI/NH$_3$) m/e 452 (M+H)$^+$. Anal calcd for C$_{25}$H$_{29}$N$_3$O$_5$·HCl: C, 61.53; H, 6.20; N, 8.61. Found: C, 61.29; H, 6.28; N, 8.45.

EXAMPLE 11

3-[2-(cis-6-Methoxy-2,3,3a,4,5,9b-hexahydro-[1H]-benz|e] isoindol-1-yl)ethyl]-7-chloro-quinazoline-2,4(1H,3H)-dione hydrochloride 2-Carboethoxy-5-chloroaniline was treated with 0.33 equivalent triphosgene by the procedures described in Example 1C. The resulting isocyanate (0.26 g, 1.25 mmol) and the compound resulting from Example 1B (0.25 g, 1.0 mmol) were treated by the procedures described in Example 1C to yield the title compound (0.12 g, 25%) as a white solid. m.p. >250° C. (dec.). $^1$H NMR (300 MHz, DMSO-d$_6$) δ 7.95 (t, 1H), 7.28 (m, 2H), 7.18 (t, 1H), 6.84 (m, 1H), 6.75 (t, 1H), 3.95–4.3 (m, 4H), 3.78 (s, 3H), 3.42–3.58 (m, 4H), 2.92–3.1 (m, 2H), 2.6–2.85 (m, 2H), 1.7–1.86 (m, 1H), 1.52–1.68 (m, 1H). MS (DCI/NH$_3$) m/e 426 (M+H)$^+$. Anal calcd for C$_{23}$H$_{24}$N$_3$O$_3$Cl·HCl·0.25 H$_2$O: C, 59.17; H, 5.51; N, 9.00. Found: C, 59.10; H, 5.52; N, 8.95.

EXAMPLE 12

3-|2-(cis-6-Methoxy-2,3,3a,4,5,9b-hexahydro-|1H|-benz|e| isoindol-1-yl)ethyl|-5-methyl-quinazoline-2,4(1H,3H)-dione hydrochloride 2-Carbomethoxy-3-methylaniline was treated with 0.33 equivalent triphosgene by the procedures described in Example 1C. The resulting isocyanate (0.28 g, 1.4 mmol) and the compound resulting from Example 1B (0.28 g, 1.1 mmol) were treated as described by the procedures described in Example 1C to yield the title compound (0.16 g, 28%) as a white solid. m.p. 178°–180° C. $^1$H NMR (300 MHz, CDCl$_3$) of the free base δ 7.38 (t, 1H), 7.17 (t, 1H), 6.92 (dd, 2H), 6.72 (dd, 2H), 4.12–4.42 (m, 4H), 3.82 (s, J=3, 3.68, q Hz, 1H), 3.4–3.58 (m, 2H), 2.93–3.06 (m, 2H), 2.7–2.85 (m, 2H), 2.73 (s, 3H), 2.51–2.65 (m, 1H), 1.87–2.0 (m, 1H), 1.53–1.7 (m, 1H). MS (DCI/NH$_3$) m/e 406 (M+H)$^+$. Anal caled for C$_{24}$H$_{27}$N$_3$O$_3$·HCl·H$_2$O: C, 62.67; H, 6.57; N, 9.14. Found: C, 62.72; H, 6.17; N, 9.08.

EXAMPLE 13

3-|2-((3aR,9bR)-cis-6-Methoxy-2,3,3a,4,5,9b-hexahydro-|1H|-benz|e]isoindol-1-yl)ethyl|-thieno|2,3-d]pyrimidine-2,4(1H,3H)-dione hydrochloride

EXAMPLE 13A

5-Methoxy-3,4dihydronaphthalene-1-carboxylic acid methyl ester

5-Methoxy-3,4-dihydronaphthalene-1-carboxylic acid (100 g, 490 mmol) was dissolved in 800 mL of methanol and 20 mL of 96% H$_2$SO$_4$, and heated at reflux for 18 hours. The reaction was then cooled and evaporated under reduced pressure to a volume of 100 mL, and quenched on ice. The aqueous mixture was extracted with diethyl ether (3×100 mL), and the organic phase was washed with water, 5% aqueous NaHCO$_3$, brine, and then dried (MgSO$_4$) and evaporated to yield 101 g (94%) of the title compound as a colorless oil. $^1$H NMR (300 MHz, CDCl$_3$) δ 2.36 (m, 2H), 2.78 (t, 3H), 3.83 (s, 6H), 6.82 (d, 1H), 7.14 (t, 1H), 7.19 (t, 1H), 7.40 (t, 1H).

EXAMPLE 13B

5-Methoxy-2-cyano-1,2,3,4tetrahydrohaphthalene-1-carboxylic acid methyl ester

A solution of 1100 mL 0.5M LiCN (550 mmol) in DMF and acetic acid (27.7 mL, 483 mmol) was prepared. The product resulting from Example 13A (101 g, 0.460 mmol) was dissolved in 100 mL DMF, and added over 15 minutes to the above solution. The reaction was stirred at 25° C. for 3.5 hours, and then poured onto ice/H$_2$O (5000 mL). The aqueous mixture was extracted with ether (3×500 mL), and the organic extracts were washed with H$_2$O and brine, dried (MgSO$_4$) and evaporated to dryness to yield 103.4 g (92%) of a light yellow oil as a mixture of cis and trans isomers of the desired product. $^1$H NMR (300 MHz, CDCl$_3$) δ 2.00–2.38 (m, 2H), 2.50–3.10 (m, 2H), 3.30–3.52 (m, 1H), 3.77 (s, 3H), 3.83 (s, 3H), 4.07 (m, 1H), 6.77 (d, 1H), 6.89 (d, 1H), 7.27 (m, 1H).

EXAMPLE 13C

5-Methoxy-1,2,3,4tetrahydronaphthalene-1,2-dicarboxylic acid

The nitrile ester resulting from Example 13B (103 g, 422 mmol) was dissolved in 700 mL ethanol and 700 mL 45% aqueous KOH, and the reaction was heated at reflux for 10 hours. The cooled solution was diluted with 1.5 kg of ice and acidified to pH 1 with concentrated aqueous HCl. The resulting product was collected by filtration, washed with H$_2$O (3×200 mL) and dried under vacuum to yield 65.3 g (62%) of the title compound as a white solid. m.p. 200°–201° C. $^1$H NMR (300 MHz, CD$_3$OD) δ 1.85 (m, 1H), 2.27 (m, 1H), 2.65 (m, 1H), 2.85 (m, 1H), 3.10 (m, 1H), 3.80 (s, 3H), 4.05 (d, 1H), 6.79 (d, 1H), 6.92 (d, 1H), 7.11 (t, 11H).

EXAMPLE 13D

5-Methoxy-1,2,3,4tetrahydronaphthalene-1,2-dicarboxylic anhydride

The compound resulting from Example 13C (65.3 g, 260 mmol) was dissolved in acetic anhydride (400 mL) and heated at reflux for 4 hours. The solvent was evaporated, and the resulting solid was triturated with 1:1 hexane:diethyl ether, and then collected and dried to yield 48.9 g (81%) of the title compound as a white solid. m.p. 138°–140° C. $^1$H NMR (300 MHz, CDCl$_3$) δ 1.97 (m, 1H), 2.28 (m, 1H), 2.47 (m, 1H), 2.95 (m, 1H), 3.55 (m, 1H), 3.83 (s, 3H), 4.32 (d, 1H), 6.83 (d, 1H), 7.17 (d, 1H), 7.27 (t, 1H).

EXAMPLE 13E (3aR,9bR)-6-Methoxy-((S)-α-methylbenzyl)-2,3,3a,4,5,9b-[1H]-hexahydrobenz[e]isoindole-1,3-dione and (3aS,9bS)-6-Methoxy-((S)-α-methylbenzyl)-2,3,3a,4,5,9b-[1H]-hexahydrobenz[e]isoindole-1,3-dione The compound resulting from Example 13D (48.8 g, 210 mmol) was combined with (S)-(-)-α-methylbenzyl amine (28.1 g, 0.230 mmol) in xylene (200 mL), and the reaction was heated to reflux with water removal (Dean Stark trap) until the theoretical amount of water was removed. The reaction was then cooled and diluted with ethyl acetate (300 mL). The resulting solution was washed with 5% aqueous HCl, 5% aqueous NaHCO$_3$ and brine, dried (MgSO$_4$) and evaporated to dryness. The resulting oily solid was triturated with diethyl ether, and the resulting crystalline title compound was collected (28.14 g, 81%) of the (3aR,9bR) product. m.p. 148°–150° C. $^1$H NMR (300 MHz, CDCl$_3$) δ 1.75 (d, 3H), 1.80 (m, 1H), 2.20 (m, 2H), 2.89 (m, 1H), 3.20 (m, 1H), 3.80 (s, 3H), 3.95 (d, 1H), 5.49 (q, 1H), 6.79 (d, 1H), 7.17–7.45 (m, 7H). From the mother liquor, on cooling, a second crop was collected (16.8 g, 48%) and shown to be the (3aS,9bS) product. m.p. 101°–103° C. $^1$H NMR (300 MHz, CDCl$_3$) δ 1.78 (d, 3H), 1.85 (m, 1H), 2.20 (m, 2H), 2.88 (m, 1H), 3.17 (m, 1H), 3.81 (s, 3H), 3.98 (d, 1H), 5.48 (q, 1H), 6.78 (d, 1H), 7.17–7.42 (m, 7H).

EXAMPLE 13F (3aR,9bR)-6-Methoxy-((S)-α-methylbenzyl)-2,3,3a,4,5,9b-[1H]-hexahydrobenz[e]isoindole hydrochloride The (3aR,9bR) compound resulting from Example 13E (28.0 g, 83.5 mmol) was dissolved in THF (100 mL) and added over 5 minutes to a 1.0M solution of BH$_3$ in THF. The reaction mixture was heated at reflux for 2 hours, and then cooled to 25° C. Methanol (100 mL) was added cautiously, and after evolution of H$_2$ ceased, solvent was evaporated at reduced pressure. The resulting oil was dissolved in 2:1 methanol:isopropyl alcohol saturated with HCl (g), and the resulting solution was heated at reflux for 3 hours. The solvent was removed in vacuo, the resulting solid was triturated with 1:1 ethanol:diethyl ether, and the title compound (25.8 g, 90%) was collected by filtration. m.p. 229°–231° C. $^1$H NMR (300 MHz, CDCl$_3$) of the free base δ 1.38 (d, 3H), 1.49 (m, 1H), 1.57 (m, 1H), 2.07 (dd, 1H), 2.15 (m, 1H), 2.40–2.72 (m, 3H), 2.97 (dd, 1H), 3.21 (q, 1H), 3.49 (m, 2H), 3.81 (s, 3H), 6.68 (d, 1H), 6.77 (d, 1H), 7.11 (t, 1H), 7.19–7.38 (m, 5H).

EXAMPLE 13G (3aR,9bR)-6-Methoxy-2,3,3a,4,5,9b-[1H]-hexahydrobenz[e]isoindole hydrochloride δ The compound resulting from Example 13F (25.7 g, 74.7 mmol) was dissolved in methanol (700 mL) and 10% Pd/C (5.9 g) was added. The reaction was hydrogenated at 4 atmospheres of hydrogen at room temperature for 24 hours. The catalyst was removed by filtration, and the solvent was evaporated to yield 15.9 g (89%) of the title compound as a white solid. m.p. 223°–225° C. $^1$H NMR (300 MHz, CD$_3$OD) δ 1.60 (m, 1H), 1.93 (m, 1H), 2.54 (m, 1H), 2.67 (m, 1H), 2.93 (m, 1H), 3.09 (dd, 1H), 3.13 (dd, 1H), 3.53 (m, 1H), 3.58 (dd, 1H), 3.67 (dd, 1H), 3.80 (s, 3H), 6.78 (d, 1H), 6.81 (d, 1H), 7.16 (t, 1H). $|α|_D^{20}$=-22.0° (c=1.39, MeOH, free base).

EXAMPLE 13H

3-[2-((3aR,9bR)-cis-6-Methoxy-2,3,3a,4,5,9b-hexahdro-[1H]-benz[e]isoindol-1-yl)ethyl]-thieno[2,3-d]pyrimidine-2,4(1H,3H)-dione hydrochloride 2-Amino-3-carboethoxythiophene, prepared by the method of Gewald, *Chemische Berichte*, 98: 3571 (1965), was treated with 2-chloroethyl-isocyanate by the procedures described in *Eur. J. Med. Chem.* 28: 499 (1993). The resulting urea (1.65 g, 6.0 mmol) and the product from Example 13G (1.10 g, 5.4 mmol) were treated by the procedures described in Example 3 to yield 0.91 g (39%) of the title compound as a white solid. m.p. 179°–182° C. (dec.). $^1$H NMR (300 MHz, CDCl$_3$) δ 1.52–1.66 (m, 1H), 1.80–1.92 (m, 1H), 2.49–2.65 (m, 3H), 2.69–2.83 (m, 2H), 3.18–3.38 (m, 2H), 3.59–3.70 (m, 1H), 3.82 (s, 3H), 3.96–4.10 (m, 2H), 4.30 (bt, 2H), 6.49 (d, 1H), 6.70 (d, 1H), 6.79 (d, 1H), 6.93 (d, 1H), 7.13 (t, 1H). MS (DCI/NH$_3$) m/e 398 (M+H)$^+$. Anal calcd for C$_{21}$H$_{23}$N$_3$O$_3$S·HCl·1.5H$_2$O: C, 54.72; H, 5.90; N, 9.12. Found: C, 55.03; H, 6.03; N, 8.83.

EXAMPLE 13I (3aR,9bR)-2-Cyanomethyl-6-methoxy-2,3,3a,4,5,9b-[1H]-hexahydrobenz[e]isoindole The compound resulting from Example 13G (2.39 g, 10.0 mmol) was dissolved in H$_2$O, basified to pH 12 with aqueous NaOH solution and extracted 3×CH$_2$Cl$_2$. The organic extracts were dried (K$_2$CO$_3$), and evaporated to yield 1.96 g (9.64 mmol) of the free base. To the free base dissolved in CH$_3$CN (10 mL) and diisopropylethylamine (5 mL) was added 0.67 mL (10.6 mmol) of chloroacetonitrile. The reaction was heated at 70° C. for 1 hour, quenched in 5% NaHCO$_3$, and extracted with ethyl acetate (2×). The organic extracts were washed with water (2×) and brine (1×), dried (Na$_2$SO$_4$) and evaporated to yield 2.20 g of the title compound as an off white solid (90.5%). $^1$H NMR (300 MHz, CDCl$_3$) δ 1.60 (m, 2H), 1.80 (m, 1H), 2.58 (m, 3H), 2.77 (m, 1H), 3.23 (m, 2H), 3.48 (q, 1H), 3.64 (s, 2H), 3.81 (s, 3H), 6.70 (d, 1H), 6.74 (d, 1H), 7.12 (t, 1H).

EXAMPLE 13J (3aR,9bR)-2-Aminoethyl-6-methoxy-2,3,3a,4,5,9b-[1H]-hexahydrobenz[e]isoindole LiAlH$_4$ (0.82 g, 21.5 mmol) was suspended in THF (30 mL) and cooled to 0° C. The compound resulting from Example 13I (0.80 g, 3.30 mmol) was dissolved in THF (5 mL) and added dropwise to the above LiAlH$_4$, suspension. The reaction was then stirred at room temperature for 1.5 hours, quenched by addition of H$_2$O (0.8 mL), 15% NaOH (0.8 mL) and H$_2$O (2.4 mL), filtered through celite, washing with several hot portions of THF, and the solvent evaporated to yield the title compound (0.75 g, 93%) as a colorless oil. $^1$H NMR (300 MHz, CDCl$_3$) δ 1.50 (m, 3H), 1.72 (m, 1H), 2.19 (m, 2H), 2.52 (m, 3H), 2.70 (m, 1H), 2.80 (t, 1H), 3.21 (dd, 1H), 3.28 (t, 1H, 3.40 (m, 1H), 3.80 (s, 3H), 6.67 (d, 1H), 6.75 (d, 1H), 7.11 (t, 1H).

EXAMPLE 14

3-[2-(cis-6-Methoxy-2,3,3a,4,5,9b-hexahydro-[1H]-benz[e]isoindol-1-yl)ethyl]-7-carbomethoxy-quinazoline-2,4(1H,3H)-dione hydrochloride 2,5-Bis-carbomethoxyaniline was treated with 0.33 equivalent triphosgene by the procedures described in Example 1C. The resulting isocyanate (0.60 g, 2.4 mmol) and the compound resulting from Example 1B (0.48 g, 1.9 mmol) were treated by the procedures described in Example 1C to yield the title compound (0.38 g, 37%) as a white solid. m.p. 230°–233° C. (dec.). $^1$H NMR (300 MHz, DMSO-$d_6$) δ 8.08 (d, 1H), 7.81 (s, 1H), 7.72 (d, 1H), 7.18 (t, 1H), 6.82 (d, 1H), 6.75 (d, 1H), 4.18–4.3 (m, 2H), 3.92 (s, 3H), 3.78 (s, 3H), 3.4–3.6 (m, 4H), 2.85–3.1 (m, 2H), 2.55–2.85 (m, 4H), 1.7–1.83 (m, 1H), 1.52–1.65 (m, 1H). MS (DCI/NH$_3$) m/e 450 (M+H)$^+$. Anal calcd for $C_{25}H_{27}N_3O_5 \cdot HCl \cdot 0.5\ H_2O$: C, 60.66; H, 5.91; N, 8.49. Found: C, 60.91; H, 5.79; N, 8.39.

EXAMPLE 15

3-[2-(cis-6-Methoxy-2,3,3a,4,5,9b-hexahydro-|1H|-benz|e| isoindol-1-yl)ethyl]-6-fluoro-quinazoline-2,4(1H,3H)-dione hydrochloride 2-Carboethoxy-4-fluoroaniline was treated with 0.33 equivalent triphosgene by the procedures described in Example 1C. The resulting isocyanate (0.46 g, 2.2 mmol) and the compound resulting from Example 1B (0.46 g, 1.9 mmol) were treated by the procedures described in Example 1C to yield the title compound (0.44 g, 55%) as a white solid. m.p. 208°–210° C. (dec). $^1$H NMR (300 MHz, DMSO-$d_6$) δ 7.55–7.7 (m, 2H), 7.28 (m, 1H), 7.17 (t, 1H), 6.71–6.88 (m, 2H), 3.95–4.33 (m, 3H), 3.87 (s, 3H), 3.68–3.75 (m, 1H), 3.4–3.58 (m, 4H), 2.92–3.08 (m, 1H), 2.58–2.85 (m, 2H), 2.32–2.48 (m, 1H), 1.7–1.87 (m, 1H), 1.5–1.7 (m, 1H). MS (DCI/NH$_3$) m/e 410 (M+H)$^+$. Anal calcd for $C_{23}H_{24}N_3O_3F \cdot HCl \cdot 0.5\ H_2O$: C, 60.72; H, 5.76; N, 9.24. Found: C, 60.35; H, 5.75; N, 9.04.

EXAMPLE 16

3-[2-(cis-6-Methoxy-2,3,3a,4,5,9b-hexahydro-[1H]-benz[e] isoindol-1-yl)ethyl]-6-nitro-quinazoline-2,4(1H,3H)-dione hydrochloride 2-Carboethoxy-4-nitroaniline was treated with 0.33 equivalent triphosgene by the procedures described in Example 1C. The resulting isocyanate (0.48 g, 2.1 mmol) and the compound resulting from Example 1B (0.46 g, 1.9 mmol) were treated by the procedures described in Example 1C to yield the title compound (0.18 g, 25%) as a white solid. m.p. >250° C. (dec.). $^1$H NMR (300 MHz, DMSO-$d_6$) δ 8.62 (d, 1H), 8.48 (dd, 1H), 7.32 (d, 1H), 7.08 (t, 1H), 6.72 (d, 2H), 4.03 (t, 2H), 3.73 (s, 3H), 3.18–3.25 (m, 4H), 2.4–2.7 (m, 4H), 2.22–2.32 (m, 2H), 1.37–1.53 (m, 1H), 1.6–1.7 (m, 1H). MS (DCI/NH$_3$) m/e 436 (M+H)$^+$. Anal calcd for $C_{23}H_{24}N_4O_5 \cdot HCl \cdot 0.25\ H_2O$: C, 57.86; H, 5.38; N, 11.73. Found: C, 57.87; H, 5.35; N, 11.50.

EXAMPLE 17

3-[2-(cis-6-Methoxy-2,3,3a,4,5,9b-hexahydro-[1H]-benz[e] isoindol-1-yl)ethyl]-6-methoxy-quinazoline-2,4(1H,3H)-dione hydrochloride 2-Carboethoxy-4methoxyaniine was treated with 0.33 equivalent triphosgene by the procedures described in Example 1C. The resulting isocyanate (0.33g, 1.5 mmol) and the product from Example 1B (0.32 g, 1.3 mmol) were treated by the procedures described in Example 1C to yield the title compound (0.129 g, 25%) as a white solid. m.p. 159°–161°; $^1$H NMR (300 MHz, DMSO-$d_6$) δ 7.35 (m, 2H), 7.18 (m, 2H), 6.7–6.88 (m, 2H), 3.98–4.18 (m, 3H), 3.8 (s, 3H), 3.78 (s, 3H), 3.6–3.8 (m, 1H), 3.4–3.6 (m, 4H), 2.95–3.1 (m, 2H), 2.6–2.85 (m, 2H), 1.7–1.9 (m, 1H), 1.55–1.68 (m, 1H). MS (DCI/NH$_3$) m/e 422 (M+H)$^+$. Anal calcd for $C_{24}H_{27}N_3O_4 \cdot HCl \cdot H_2O$: C, 60.56; H, 6.35; N, 8.83. Found: C, 60.54; H, 6.33; N, 8.55.

EXAMPLE 18

3-|2-(cis-6-Methoxy-2,3,3a,4,5,9b-hexahydro-|1H|-benz|e| isoindol-1-yl)ethyl|-6,7,8-trimethoxy-quinazoline-2,4(1H,3H)-dione hydrochloride 2,3,4-Trimethoxy-6-carbomethoxyaniline was treated with 0.33 equivalent triphosgene by the procedures described in Example 1C. The resulting isocyanate (0.50 g, 2.0 mmol) and the compound resulting from Example 1B (0.46 g, 1.9 mmol) were treated by the procedures described in Example 1C to yield the title compound (0.22 g, 25%) as a white solid. m.p. 205°–207° C. $^1$H NMR (300 MHz, DMSO-$d_6$) δ 7.12–7.25 (m, 2H), 6.71–6.88 (m, 2H), 3.95–4.3 (m, 4H), 3.88 (s, 3H), 3.85 (s, 3H), 3.82 (s, 3H), 3.78 (s, 3H), 3.42–3.57 (m, 4H), 2.93–3.08 (m, 1H), 2.62–2.83 (m, 2H), 2.34–2.48 (m, 1H), 1.72–1.87 (m, 1H), 1.52–1.68 (m, 1H). MS (DCI/NH$_3$) m/e 482 (M+H)$^+$. Anal calcd for $C_{26}H_{31}N_3O_6 \cdot HCl \cdot 0.25 H_2O$: C, 59.77; H, 6.27; N, 8.04. Found: C, 59.69; H, 6.30; N, 7.96.

EXAMPLE 19

3-[2-(cis-6-Methoxy-2,3,3a,4,5,9b-hexahydro-[1H]-benz[e] isoindol-1-yl)ethyl -8-methyl-quinazoline-2,4(1H,3H)-dione hydrochloride 2-Carboethoxy-6-methylaniline was treated with 0.33 equivalent triphosgene by the procedures described in Example 1C. The resulting isocyanate (0.40 g, 2.0 mmol) and the compound resulting from Example 1B (0.46 g, 1.6 mmol) were treated by the procedures described in Example 1C to yield the title compound (0.12 g, 18%) as a white solid. m.p. 250°–252° C. (dec). $^1$H NMR (300 MHz, DMSO-$d_6$) of the free base δ 7.8 (d, 1H), 7.5 (d, 1H), 7.05–7.13 (m, 2H), 6.72 (dd, 2H), 4.02 (t, 2H,), 3.72 (t, 3H), 3.12–3.3 (m, 3H), 2.52–2.7 (m, 4H), 2.38–2.49 (m, 1H), 2.35 (s, 3H), 2.1–2.25 (m, 2H), 1.58–1.7 (m, 1H), 1.37–1.5 (m, 1H). MS (DCI/NH$_3$) m/e 406 (M+H)$^+$. Anal calcd for $C_{24}H_{27}N_3O_3 \cdot HCl \cdot 0.25\ H_2O$: C, 64.57; H, 6.43; N, 9.41. Found: C, 64.63; H, 6.36; N, 9.42.

EXAMPLE 20

3-[2-(cis-6-Methoxy-2,3,3a,4,5,9b-hexahydro-[1H]-benz[e] isoindol-1-yl)ethyl]-6,8-dimethyl-quinazoline-2,4(1H,3H)-dione hydrochloride 2-Carboethoxy-4,6-dimethylaniline was treated with 0.33 equivalent triphosgene by the procedures described in Example 1C. The resulting isocyanate (0.45 g, 2.1 mmol) and the compound resulting from Example 1B (0.46 g, 1.6 mmol) were treated by the procedures described in Example 1C to yield the title compound (0.22 g, 30%) as a white solid. m.p. 273°–4° C. (dec). $^1$H NMR (300 MHz, DMSO-$d_6$) δ 7.62 (s, 1H), 7.39 (s, 1H), 7.18 (t, 1H), 6.7–6.9 (m, 2H), 4.2–4.3 (m, 2H), 4.08–4.2 (m, 1H), 3.8–4.1 (m, 1H), 3.8 (s, 1H), 3.4–3.58 (m, 4H), 2.88–3.1 (m, 2H), 2.6–2.83 (m, 2H), 2.33 (s, 3H), 2.3 (s, 3H), 1.72–1.85 (m, 1H), 1.48–168 (m, 1H). MS (DCI/NH$_3$) m/e 420 (M+H)$^+$. Anal calcd for $C_{25}H_{29}N_3O_3 \cdot HCl$: C, 65.85; H, 6.63; N, 9.22. Found: C, 65.60; H, 6.59; N, 9.03.

EXAMPLE 21

3-[2-(cis-6-Methoxy-2,3 3a,4,5,9b-hexahydro-|1H|-benz|e| isoindol-1-yl)ethyl]-pyrido[2,3-d]pyrimidine-2,4(1H,3H)-dione hydrochloride 2-Amino-3-ethoxycarbonylpyridine (0.46 g, 2.8 mmol), prepared from 2-aminonicotinic acid by the procedure described in *J. Chem. Soc.*, 1045 (1956) for 3-aminopicolinic acid, and Et$_3$N (0.74 mL, 5.3 mmol) were taken up in anhydrous CH$_2$Cl$_2$ under N$_2$ and cooled to −78° C. Phosgene (1.5 mL of 1.93M solution in toluene, 2.8 mmol) was added, and the reaction was stirred at −78° C. for 45 minutes and at 25° C. for 1.5 hours. The compound resulting from Example 1B in 4 mL of $CH_2Cl_2$ was added, and the reaction was stirred for 2 hours. The reaction mixture was partitined between 1M NaOH and $CH_2Cl_2$. The $CH_2Cl_2$ layer was dried ($MgSO_4$), filtered, concentrated in vacuo and taken up in THF (30 mL). To this solution was added 6 mL of 1M potassium ten-butoxide in THF. The reaction was stirred for 1 hour at 25° C. and then was concentrated and chromatographed eluting with 5% EtOH in $CH_2Cl_2$ saturated with $NH_3$ increasing the EtOH concentration to 10%. The product (0.45 g, 40%) was converted to its HCl salt which was recrystallized from $EtOH/Et_2O$. m.p. 234°–236° C. $^1H$ NMR (300 MHz, $CDCl_3$) of the free base δ 1.47–1.61 (m, 1H), 1.72–1.86 (m, 1H), 2.27 (q, 2H), 2.49–2.61 (m, 1H), 2.64–2.77 (m, 2H), 2.84–2.95 (m, 1H), 3.05–3.16 (m, 1H), 3.53 (q, 1H), 3.76 (t, 2H), 3.80 (s, 3H), 4.17–4.35 (m, 2H), 6.67 (d, 1H), 6.77 (d, 6.90–6.96 (m, 1H), 7.09 (t, 1H), 8.05 (dt, 1H), 8.48 (dd, 1H). MS ($DCI/NH_3$) m/e 393 $(M+H)^+$. Anal calcd for $C_{22}H_{24}N_4O_3 \cdot HCl \cdot 0.75 H_2O$: C, 59.73; H, 6.04; N, 12.66. Found: C, 59.57; H, 5.96; N, 12.39.

EXAMPLE 22

3-[2-(cis-6-Methoxy-2,3,3a,4,5,9b-hexahydro-[1H]-benz[e]isoindol-1-yl)ethyl]-pyrido[3,2-d]pyrimidine-2,4(1H,3H)-dione hydrochloride Following the procedure described for Example 21, 3-amino-2-ethoxycarbonylpyridine (0.30 g, 1.8 mmol), prepared by the method described in *J. Chem. Soc.*, 1045 (1956), $Et_3N$ (0.48 mL, 3.4 mmol), phosgene (0.93 mL, 1.93M in toluene, 1.8 mmol), and the compound resulting from Example 1B (0.40 g, 1.6 mmol) provided 0.51g (80%) of the desired product which was converted to its HCl salt. m.p. 195°–198° C. $^1H$ NMR (300 MHz, $CDCl_3$) of the free base δ 1.47–1.62 (m, 1H), 1.74–1.87 (m, 1H), 2.47 (t, 2H), 2.50–2.76 (m, 3H), 2.97–3.07 (m, 1H), 3.13–3.25 (m, 1H), 3.46 (q, 1H), 3.70–3.83 (m, 2H), 3.78 (s, 3H), 4.24–4.43 (m, 2H), 6.65 (d, 1H), 6.77 (d, 1H), 7.07 (d, 1H), 7.12 (d, 1H), 7.31 (dd, 1H), 8.25 (d, 1H). MS ($DCI/NH_3$) m/e 393 $(M+H)^+$. Anal calcd for $C_{22}H_{24}N_4O_3 \cdot HCl \cdot 1.25 H_2O$: C, 58.53; H, 6.14; N, 12.41. Found: C, 58.50; H, 5.83; N, 12.32.

EXAMPLE 23

3-[2-(cis-6-Methoxy-2,3,3a,4,5,9b-hexahydro-[1H]-benz[e]isoindol-1-yl)ethyl]-5-chloro-quinazoline-2,4(1H,3H)-dione hydrochloride 2-Carboethoxy-3-chloroaniline was treated with 0.33 equivalent triphosgene by the procedures described in Example 1C. The resulting isocyanate (0.44 g, 2.1 mmol) and the compound resulting from Example 1B (0.40 g, 1.6 mmol) were treated by the procedures described in Example 1C to yield the title compound (0.12 g, 18%) as a white solid. m.p. >250° C. (dec). $^1H$ NMR (300 MHz, $CDCl_3$) of the free base δ 7.35 (m, 2H), 7.18 (m, 2H), 7.0 (d, 2H), 6.73 (dd, 2H), 4.1–4.42 (m, 4H), 3.82 (s, 3H), 3.68 (q, 1H), 3.4–3.57 (m, 2H), 2.87–3.0 (m, 2H), 2.7–284 (m, 2H), 2.52–2.65 (m, 1H), 1.87–1.98 (m, 1H), 1.55–1.7 (m, 1H). MS ($DCI/NH_3$) m/e 426 $(M+H)^+$. Anal calcd for $C_{23}H_{24}N_3O_3Cl \cdot HCl \cdot 2 H_2O$: C, 55.43; H, 5.86; N, 8.43. Found: C, 55.73; H, 5.60; N, 8.31.

EXAMPLE 24

3-[2-(cis-6-Methoxy-2,3,3a,4,5,9b-hexahydro-[1H]-benz[e]isoindol-1-yl)ethyl]-pyrido[3,4d]pyrimidine-2,4(1H,3H)-dione dihydrochloride Following the procedure described for Example 21, 3-amino-4-ethoxycarbonylpyridine (0.58 g, 3.5 mmol), prepared by substituting 3,4-pyridinedicarboximide for quinolinimide and the procedure described in *J. Chem. Soc.*, 1045 (1956), $Et_3N$ (1.5 mL, 10.5 mmol), phosgene (1.8 mL of a 1.93M solution in toluene, 3.5 mmol), and the compound resulting from Example 1B (0.60 g, 2.4 mmol) provided 0.68 g (71%) of the desired product which was converted to its HCl salt. m.p. 228°–230° C. $^1H$ NMR (300 MHz, $CD_3OD$) of the free base δ 1.45–1.49 (m, 1H), 1.66–1.78 (m, 1H), 2.22 (t, 1H), 2.33 (dt, 1H), 2.50–2.68 (m, 3H), 2.77–2.86 (m, 2H), 3.24–3.51 (m, 3H), 3.77 (s, 3H), 4.20 (t, 2H), 6.71 (d 2H), 7.07 (t, 1H), 7.91 (d, 1H), 8.39 (d, 1H), 8.55 (s, 1H). MS ($DCI/NH_3$) m/e 393 $(M+H)^+$. Anal calcd for $C_{22}H_{24}N_4O_3 \cdot 2 HCl$: C, 56.78; H, 5.63; N, 12.04. Found: C, 56.31; H, 5.63; N, 11.82.

EXAMPLE 25

3-[2-(cis-6-Methoxy-2,3,3a,4,5,9b-hexahydro-[1H]-benz[e]isoindol-1-yl)ethyl]-7-fluoro-quinazoline-2,4(1H,3H)-dione hydrochloride 2-Carboethoxy-5fluoroaniline was treated with 0.33 equivalent triphosgene by the procedure described in Example 1C. The resulting isocyanate (0.46 g, 2.1 mmol) and the compound resulting from Example 1B (0.46 g, 1.9 mmol) were treated by the procedures described in Example 1C to yield the title compound (0.49 g, 60%) as a white solid. m.p. 236°–238° C. $^1H$ NMR (300 MHz, $CDCl_3$) of the free base δ 7.95 (q, 1H), 7.1 (t, 1H), 6.72–6.8 (m, 2H), 6.67 (d, 1H), 6.55 (dd, 1H), 4.15–4.35 (m, 2H), 3.81 (s, 3H), 3.43–3.75 (m, 2H), 2.78–3.15 (m, 2H), 2.5–2.8 (m, 3H), 2.3–2.47 (m, 2H), 1.48–1.87 (m, 3H). MS ($DCI/NH_3$) m/e 410 $(M+H)^+$. Anal calcd for $C_{23}H_{24}N_3O_3F \cdot HCl \cdot 0.25 H_2O$: C, 61.00; H, 5.62; N, 9.29. Found: C, 61.33; H, 5.71; N, 9.33.

EXAMPLE 26

3-[2-(cis-6-Methoxy-2,3,3a,4,5,9b-hexahydro-[1H]-benz[e]isoindol-1-yl)ethyl]-1-methyl-quinazoline-2,4(1H,3H)-dione hydrochloride N-Methyl-2-carboethoxyaniline (5.0 g, 28 mmol) was treated with 2-chloroethylisocyanate (2.86 mL, 28 mmol) at reflux in toluene for 18 hours. The reaction was cooled to 25° C., and the crystalline product was collected by filtration to yield the intermediate 1-methyl-3-(2-chloroethyl)quinazoline-2-4dione. The intermediate quinazolinedione (0.53 g, 2.2 mmol) and cis-6-methoxy-2,3,3a,4,5,9b-[1H]-benz[e]isoindole (0.38 g, 1.87 mmol) were combined in acetonitrile (3 mL) and diisopropylethylamine (0.8 mL) was added. The reaction mixture was heated at reflux for 18 hours. The resulting product was converted to its HCl salt and recrystallized from acetone:ether to yield the title compound (0.30 g, 40%) as a white solid. m.p. 215°–217° C. (dec). $^1H$ NMR (300 MHz, $CDCl_3$) of the free base δ 8.2 (dd, 1H), 7.7 (dt, 1H), 7.1–7.32 (m, 3H), 6.75 (t, 2H), 4.48 (m, 2H), 4.1–4.3 (m, 2H), 3.81 (s, 3H), 3.68 (m, 1H), 3.6 (s, 3H), 3.35–3.5 (m, 2H), 2.87–3 (m, 2H), 2.72–2.87 (m, 2H), 2.52–2.65 (m, 1H), 1.88–2.0 (m, 1H), 1.55–1.7 (m, 1H). MS ($DCI/NH_3$) m/e 406 $(M+H)^+$. Anal calcd for $C_{24}H_{27}N_3O_3 \cdot HCl \cdot H_2O$: C, 62.67; H, 6.57; N, 9.14. Found: C, 62.52; H, 6.51; N, 9.03.

EXAMPLE 27

3-[2-(cis-6-Methoxy-2,3,3a,4,5,9b-hexahydro-[1H]-benz[e]isoindol-1-yl)ethyl]-pyrido[4,3-d]pyrimidine-2,4(1H,3H)-dione dihydrochloride Following the procedures described in Example 21, 4amino-3-ethoxycarbonylpyridine (0.57 g, 3.4 mmol), prepared by the procedures described in *J. Org. Chem.*, 14: 97 (1949), $Et_3N$ (0.85 mL, 6.1 mmol), phosgene (1.5 mL of a 1.93M solution in toluene, 2.9 mmol), and the compound resulting from Example 1B (0.60 g, 2.4 mmol) provided 0.69 g (72%) of the desired product which was converted to its HCl salt. m.p. 229°–233° C. $^1$H NMR (300 MHz, CDCl$_3$) of the free base δ 1.49–1.62 (m, 1H), 1.75–1.87 (m, 1H), 2.38 (t, 2H), 2.50–2.77 (m, 3H), 2.88–2.98 (m, 1H), 3.09–3.20 (m, 1H), 3.47 (q, 1H), 3.69 (bt, 2H), 3.80 (s, 3H), 4.15–4.37 (m, 2H), 6.63 (d, 1H), 6.67 (d, 1H), 6.78 (d, 1H), 7.10 (t, 1H), 8.47 (d, 1H), 8.98 (s, 1H). MS (DCI/NH$_3$) m/e 393 (M+H)$^+$. Anal calcd for C$_{22}$H$_{24}$N$_4$O$_3$·2 HCl·1.5 H$_2$O: C, 53.66; H, 5.94; N, 11.38. Found: C, 53.83; H, 6.07; N, 11.31.

EXAMPLE 28

3-[2-(cis-6-Methoxy-2,3,3a,4,5,9b-hexahydro-[1H]-benz[e]isoindol-1-yl)ethyl]-1-methyl-1H-pyrazolo[3,4-d]pyrimidine-4,6(5H,7H)-dione hydrochloride Ethyl-5-amino-1-methylpyrazole-4-carboxylate (0.40 g, 2.4 mmol) was dissolved in CH$_2$Cl$_2$ (10 mL) and triethylamine (0.68 mL, 4.89 mmol) and cooled to −78° C. To the solution was added 1.93M phosgene in toluene (1.23 mL, 2.4 mmol). After stirring at −78° C. for 1 hour, and then 25° C. for 30 minutes, the compound resulting from Example 1B (0.53 g, 2.2 mmol) was added. After 2 hours, the intermedate unsymmetrical urea was isolated. The intermediate product (0.70 g) in ethanol (10 mL) was treated with 1.0M KOtBu in THF (2.0 mL) and the reaction was heated at 75° C. for 45 minutes. The reaction was quenched with 1.0N HCl to yield the title compound as its HCl salt. Recrystallization form methanol:ether yielded 0.420 g (45%) of a white solid. m.p. >250° C. (dec). $^1$H NMR (300 MHz, CD$_3$OD) δ 1.67 (m, 1H), 1.92 (m, 1H), 2.60 (m, 1H), 2.83 (m, 3H), 3.30 (m, 3H), 3.52 (t, 2H), 3.68 (br s, 1H), 3.81 (s, 3H), 3.82 (s, 3H), 4.32 (t, 2H), 6.79 (d, 1H), 6.82 (d, 1H), 7.18 (t, 1H), 7.85 (s, 1H). MS (DCI/NH$_3$) m/e 396 (M+H)$^+$. Anal calcd for C$_{21}$H$_{26}$ClN$_5$O$_3$·0.75 H$_2$O: C, 56.63; H, 6.22; N, 15.72. Found: C, 56.77; H, 5.86; N, 15.84.

EXAMPLE 29

3-[2-(cis-6-Methoxy-2,3,3a,4,5,9b-hexahydro-[1H]-benz[e]isoindol-1-yl)ethyl]-6-methylthieno[2,3-d]pyrimidine-2,4(1H,3H)-dione hydrochloride 2-Amino-3-carboethoxy-5-methylthiophene, prepared by the method of Gewald, et al., *Chem. Ber.*, 98: 94 (1966), was treated with 2-chloroethylisocyanate by the procedures described in *Eur. J. Med. Chem.*, 28: 499 (1993). The resulting urea (0.78 g, 2.7 mmol) and cis-6-methoxy-2,3,3a,4,5,9b-hexahydro-[1H]-benz[e]isoindole (0.49 g, 2.42 mmol) were treated by the procedures described in Example 3 to yield 0.140 g (15%) of the title compound as a white solid. m.p. >250° C. (dec). $^1$H NMR (300 MHz, DMSO-d$_6$) δ 1.60 (m, 1H), 1.80 (m, 1H), 2.40 (s, 3H), 2.50 (m, 1H), 2.70 (m, 2H), 3.00 (m, 2H), 3.42 (m, 3H), 3.79 (s, 3H), 4.11 (m, 1H), 4.18 (m, 3H), 6.76 (br d, 1H), 6.84 (d, 1H), 6.90 (s, 1H), 7.18 (t, 1H), 12.25 (br s, 1H). MS (DCI/NH$_3$) m/e 412 (M+H)$^+$. Anal calcd for C$_{22}$H$_{26}$ClN$_3$O$_3$S: C, 58.98; H, 5.85; N, 9.38. Found: C, 58.58; H, 5.84; N, 9.08.

EXAMPLE 30

3-[2-(cis-6-Methoxy-2,3,3a,4,5,9b-hexahydro-[1H]-benz[e]isoindol-1-yl)ethyl]-1H-pyrrolo[2,3-d]pyrimidine-2,4(3H,7H)-dione fumarate 2-Amino-3,4bis(ethoxycarbonyl)pyrrole, prepared by the method described in *J. Prakt. Chem.*, 314: 303 (1972), was reacted with 2-chloroethylisocyanate by the procedures described in *Eur. J. Med. Chem.* 28: 499 (1993). The resulting urea was reacted with cis-6-methoxy-2,3,3a,4,5,9b-hexahydro-[1H]-benz[e]isoindole by the procedures described in Example 3. The urea ester intermediate (400 mg, 0.80 mmol) was treated with 5% KOH (50 mL) and heated at 110° C. for 1 hour. After cooling to room temperature the majority of the KOH was neutralized with concentrated HCl, followed by consumption of the remainder with solid NaHCO$_3$ resulting in the precipitation of the product at pH 12. The product was extracted into CH$_2$Cl$_{12}$, the organics dried (Na$_2$SO$_4$), filtered through celite and the solvent evaporated to give 196 mg of free base. The solid was dissolved in methanol and treated with a methanolic solution of fumaric acid (60 mg) to give 160 mg (39%) of the title compound as its fumarate salt. $^1$H NMR (300 MHz, CD$_3$OD) δ 1.62 (m, 1H), 1.90 (m, 1H), 2.58 (ddd, 1H), 2.78 (m, 1H), 2.82 (dt, 1H), 3.18 (m, 2H), 3.40 (t, 2H), 3.62 (dd, 1H), 3.81 (s, 3H), 3.86 (dd, 1H), 4.01 (dd, 1H), 4.33 (t, 2H), 6.42 (d, 1H), 6.64 (d, 1H), 6.65 (s, 2H), 6.77 (d, 1H), 6.81 (d, 1H), 7.15 (t, 1H). MS (DCI/NH$_3$) m/e 381 (M+H)$^+$. Anal calcd for C$_{25}$H$_{28}$N$_4$O$_7$·0.75 H$_2$O: C, 58.87; H, 5.83; N, 10.85. Found: C, 58.93; H, 5.73; N, 11.07.

EXAMPLE 31

3-[2-(cis-6-Methoxy-2,3,3a,4,5,9b-hexahydro-[1H]-benz[e]isoindol-1-yl)ethyl]-7-phenylthieno[3,2-d]pyrimidine-2,4(1H,3H)-dione methanesulfonate 2-Carboethoxy-3-amino-4phenylthiophene, prepared by the method of Kirsch, et al., *J. Heterocyclic Chem.*, 19: 443 (1982), was treated with 0.33 equivalent triphosgene by the procedures described in Example 1C. The resulting isocyanate (0.90 g, 3.3 mmol) and the compound resulting from Example 1B (0.55 g, 2.2 mmol) were treated by the procedures described in Example 1C substituting methanesulfonic acid in the salt forming step, to yield the title compound (0.39 g, 38%) as a white solid. m.p. 268°–271° C. $^1$H NMR (300 MHz, DMSO-d$_6$) δ 1.6 (m, 2H), 1.8 (m, 2H), 2.65 (m, 3H), 3.0 (m, 2H), 3.35–3.55 (m, 3H), 3.75 (s, 3H), 4.0–4.25 (m, 2H), 6.75 (m, 1H), 6.85 (m, 1H), 7.18 (t, 1H), 7.45 (m, 3H), 8.15 (m, 2H), 10.35 (s, 1H). MS (DCI/NH$_3$) m/e 474 (M+H)$^+$. Anal calcd for C$_{27}$H$_{31}$N$_3$O$_6$S$_2$·0.25 H$_2$O: C, 58.57; H, 5.53; N, 7.32. Found: C, 58.62; H, 5.53; N, 6.99.

EXAMPLE 32

3-[2-(cis-6-Methoxy-2,3,3a,4,5,9b-hexahydro-[1H]-benz[e]isoindol-1-yl)ethyl]-6-phenylthieno[3,2-d]pyrimidine-2,4(1H,3H)-dione hydrochloride 2-Carboethoxy-3-amino-5-phenylthiophene, prepared by the method described in *Synthesis*, 275 (1984), was treated with 0.33 equivalent triphosgene by the procedures described in Example 1C. The resulting isocyanate (0.54 g, 2.1 mmol) and the compound resulting from Example 1B (0.40 g, 1.6 mmol) were treated by the procedures described in Example 1C to yield the title compound (0.39 g, 38%) as a white solid. m.p. 229.5°–231° C. $^1$H NMR (300 MHz, DMSO-d$_6$) δ 1.6 (m, 2H), 1.8 (m, 2H), 2.65 (m, 3H), 3.0 (m, 2H), 3.35–3.55 (m, 3H), 3.75 (s, 3H), 4.0–4.25 (m, 2H), 6.8 (m, 2H), 7.18 (t, 1H), 7.3 (d, 1H), 7.5 (m, 3H), 7.8 (m, 2H), 10.35 (s, 1H). MS (DCI/NH$_3$) m/e 474 (M+H)$^+$. Anal calcd for C$_{27}$H$_{28}$ClN$_3$O$_3$S·0.5 H$_2$O: C, 62.48; H, 5.63; N, 8.10. Found: C, 62.29; H, 5.43; N, 8.10.

EXAMPLE 33

3-[2-(cis-6-Methoxy-2,3,3a,4,5,9b-hexahydro-[1H]-benz[e]isoindol-1-yl)ethyl]-6,7-dimethoxy-quinazoline-4(3H)-one dihydrochloride Ethyl 2-(N,N-dimethyl-N'-formamidinyl)-3,4dimethoxybenzoate (1.68 g, 6.0 mmol), prepared from ethyl 6-amino-3,4dimethoxybenzoate and using the procedures described by Gupton J. T., Miller J. F., Bryant R. D. Maloney P. R. and Foster B. S., *Tetrahedron*, 43(8): 1747–1752 (1987), and the compound resulting from Example 1C (0.59 g, 2.4 mmol) in 1,4dioxane (20 mL) and p-toluenesulfonic acid monohydrate (0.05 g, 0.2 mmol)

were refluxed for 4 hours and then concentrated to a crude oil. Trituration with MeOH afforded the product as a free base (0.66 g, 63%). A portion (0.32 g) was dissolved in methylene chloride followed and treated with HCl(g) in Et$_2$O to yield the tide compound (0.37 g) as a white solid. mp 180°–185° C. (of a sample recrystallized from EtOH/Et$_2$O). $^1$H NMR (300 MHz, D$_2$O) δ 8.25 (s, 1H), 7.38 (br s, 1H), 7.25 (t, J=7.9 Hz, 1H), 7.05 (s, 1H), 6.94–6.89 (d, 1H), 6.91–6.86 (s, 1H), 4.72 (s, 3H), 4.44 (t, J=6.5 Hz, 2H), 3.97 (s, 3H), 3.92 (s, 3H), 3.83 (s, 3H), 3.70 (br s, 3H), 3.24–3.10 (br s, 1H), 2.85–2.74 (m, 2H), 2.61–2.53 (m, 1H), 1.97–1.90 (m, 1H), 1.66–1.62 (m, 1H). MS (DCI/NH$_3$) m/e 436 (M+H)$^+$. Anal calcd for C$_{25}$H$_{29}$N$_3$O$_4$·0.7 HCl·0.4 EtOH: C, 56.09H, 6.22; N, 7.60. Found: C, 56.04; H, 6.35; N, 7.72.

EXAMPLE 34

3-|2-(cis-6-Methoxy-2,3,3a,4,5,9b-hexahydro-|1H|-benz|e|isoindol-1-yl)ethyl|-quinazoline-4(3H)-one dihydrochloride Methyl 2-(N,N-dimethyl-N'-formamidinyl) benzoate was prepared according to the method of Gupton J. T., Miller J. F., Bryant R. D. Maloney P. R., and Foster B. S., *Tetrahedron*, 43(8): 1747–1752 (1987). Methyl 2-(N,N-dimethyl-N'-formamidinyl) benzoate (1.7 g, 8.1 mmol) and the compound resulting from Example 1C (0.5 g, 2.0 mmol) were refluxed in a solution of 1,4-dioxane (25 mL) and p-toluenesulfonic acid monohydrate (0.04 g, 0.2 mmol) for 3 hours. The reaction mixture was concentrated to a crude oil which was triturated with hexane to give a crude solid. The solid was collected by filtration and washed with EtOAc to give a white solid. The free base was dissolved in methylene chloride and treated with an ethereal solution of HCl to yield the title compound (0.40 g, 45%) as a white solid. m.p. >200° C. (on a sample recrystallized from EtOH/Et$_2$O). $^1$H NMR (300 MHz, D$_2$O) δ 8.38 (s, 1H), 8.23 (br d, 1H), 7.94 (t, J=7.6Hz, 1H), 7.76–7.73 (d, 1H), 7.67 (t, J=7.3 Hz, 1H), 7.26 (t, J=7.9 Hz, 1H), 6.95–6.90 (d, 1H), 6.93–6.88 (d, 1H), 4.66–4.56 (m, 3H), 4.48 (t, J=7.5 Hz, 2H), 3.84 (s, 3H), 3.72–3.60 (m, 3H), 3.18 (br s, 1H), 2.82 (br s, 2H), 2.62–2.53 (m, 1H), 1.97–1.90 (m, 1H), 1.65 (br s, 1H). MS (DCI/NH$_3$) m/e 876 (M+H)$^+$. Anal calcd for C$_{23}$H$_{27}$Cl$_2$N$_3$O$_2$·0.3 HCl·0.2 EtOH: C, 59.98H, 6.13; N, 8.96. Found: C, 59.88; H, 6.17; N, 8.95.

EXAMPLE 35

3-|2-(cis-6-Hydroxy-2,3,3a,4,5,9b-hexahydro-[1H]-benz|e| isoindol-1-yl)ethyl|-thieno[2,3-d]pyrimidine-2,4(1H,3H)-dione hydrobromide To a suspension of the compound resulting from Example 3 (100 mg, 0.23 mmol, 1.0 equiv) in 3 mL of methylene chloride cooled to −78° C. was added 0.46 mL of 1M BBr$_3$ in methylene chloride (0.46 mmol, 2.0 equiv). The reaction was then warmed to room temperature and stirred for 5 hours. The oily suspention was then cooled to −78° C. and quenched with 20 mL of dry methanol. The reaction solution was then evaporated to a tan solid which was crystallized from methanol-methylene chloride to furnish the title compound as a white powder (95 mg, 93%). m.p. >200° C. $^1$H NMR (CD$_3$OD, 300 MHz) δ 1.60 (1H, m), 1.90 (1H, m), 2.57 (1H, m), 2.80 (2H, m), 3.30 (1H, m), 3.35 (1H, m), 3.55 (2H, t, J=6.0 Hz), 3.62 (1H, m), 3.90 (2H, m), 4.35 (2H, t, J=6.0 Hz), 4.95 (1H, m), 6.65 (2H, m), 7.0 (1H, t, J=7.5 Hz), 7.06 (1H, d, J=7.5 Hz), 7.25 (1H, d, J=7.5 Hz). MS (DCI/NH$_3$) m/e 384 (M+H)$^+$. IR (KBr): 3400, 2720, 2650, 1720, 1640 cm$^{-1}$. Anal calcd for C$_{20}$H$_{22}$N$_3$O$_3$SBr: C, 51.73; H, 4.78; N, 9.05. Found: C, 51.39; H, 4.76: N 8.78.

EXAMPLE 36

3-|2-((3aR,9bR)-cis-6-Methoxy-2,33a,4,5,9b-hexahydro-|1H|-benz|e|isoindol-1-yl)ethyl|-quinazoline-2(1H)-one hydrochloride

EXAMPLE 36A

2-|2-((3aR,9bR)-cis-6-Methoxy-2,3,3a,4,5,9b-hexahydro-|1H|-benz|e|isoindol-1-yl)ethyl|aminomethyl-aniline Using the procedure described by Langley D. R., Thurston, D. E. *J. Org. Chem.* 52 (1): 91–97 (1987), 2-nitrobenzyl bromide and the compound resulting from Example 13J were reacted with stannous chloride dihydrate in methanol to afford the title compound.

EXAMPLE 36B

3-|2-((3aR,9bR)-cis-6-Methoxy-2,3,3a,4,5,9b-hexahydro-|1H|-benz|isoindol-1-yl)ethyl|-quinazoline-2(1H)-one hydrochloride A solution of the compound resulting from Example 36A (136 mg, 0.387 mmol) in 4 mL of dry tetrahydrofuran was cooled and a solution of 75.3 mg (0.464 mmol) of N,N'-carbonyldiimidazole in 2 mL of dry tetrahydrofuran was added rapidly with stirring. The cooling bath was removed and stirring was continued for 3 hours. The solvent was evaporated to give the crude product. Chromatography on silica gel eluting with 3% MeOH in CHCl$_3$ afforded the product as a free base. The free base was dissolved in methylene chloride and treated with HCl(g) in Et$_2$O to yield the title compound (45 mg) as a white solid. m.p. 145°–147° C. (on a sample recrystallized from EtOH/Et$_2$O). $^1$H NMR (300 MHz, CD$_3$OD) δ 1.30 (m, 1H), 1.55–1.70 (m, 3H), 2.20 (m, 2H), 2.52–2.65 (m, 4H), 2.72 (m, 2H), 3.25 (m, 1H), 3.35 (s, 2H), 3.42 (m, 1H), 3.82 (s, 3H), 6.70 (m, 4H), 7.20 (m, 3H). MS (DCI/NH$_3$) m/e 378 (M+H)$^+$. Anal. calcd for C$_{23}$H$_{28}$N$_3$O$_2$Cl·0.9 HCl: C, 61.83; H, 6.52; N, 9.41. Found: C, 61.91; H, 6.46; N, 9.29.

EXAMPLE 37

3-|2-((3aR,9bR)-cis-6-Methoxy-2,3,3a,4,5,9b-hexahydro-[1H]-benz[e]isoindol-1-yl)ethyl]-6,7-methylenedioxyquinazoline-2,4(1H,3H)-dione hydrochloride Following the procedure described for Example 21, 6-amino-1,3-benzodioxole-5-carboxylic acid ethyl ester (0.51 g, 2.4 mmol), prepared in analogy to the procedure described in J. Indian Chem. Soc., 64(6), 373–5 (1987), Et$_3$N (0.74 mL, 5.3 mmol), phosgene (1.3 mL 1.93M solution in toluene, 2.4 mmol), and the compound resulting from Example 13J (0.50 g, 2.0 mmol) were reacted to give 0.82 g (93%) of the desired product as its HCl salt. m.p. 257°–258° C. $^1$H NMR (300 MHz, CDCl$_3$) of the free base δ 1.46–1.61 (m, 1H), 1.71–1.86 (m, 1H), 2.22–2.36 (m, 2H), 2.50–2.75 (m, 3H), 2.80–2.92 (m, 1H), 3.03–3.13 (m, 1H), 3.40–3.52 (m, 1H), 3.63–3.76 (m, 2H), 3.81 (s, 3H), 4.15–4.35 (m, 2H), 6.00 (s, 2H), 6.23 (s, 1H), 6.65 (d, 1H), 6.76 (d, 1H), 7.08 (t, 1H), 7.23 (s, 1H). MS (DCI/NH$_3$) m/e 436 (M+H)$^+$. Anal calcd for C$_{24}$H$_{25}$N$_3$O$_5$·HCl): C, 61.08; H, 5.55; N, 8.90. Found: C, 60.81; H, 5.51; N, 8.78.

EXAMPLE 38

3-|2-((3aR,9bR)-cis-6-Methoxy-2,3,3a,4,5,9b-hexahydro-[1H]-benz[e]isoindol-1-yl)ethyl]-6,7-ethylenedioxyquinazoline-2,4(1H,3H)-dione hydrochloride Following the procedure described for Example 21, 7-amino-2,3-dihydro-1,4-benzodioxane-6-carboxylic acid ethyl ester (0.55 g, 2.4 mmol), prepared in analogy to the procedure described in U.S. Pat. No. 4,011,323 which is incorporated herein by reference, Et$_3$N (0.74 mL, 5.3 mmol), phosgene (1.3 mL 1.93M solution in toluene, 2.4 mmol), and the compound resulting from Example 13J (0.50 g, 2.0 mmol) were reacted to give 0.91 g (99%) of the desired product as its HCl salt. m.p. 212°–214° C. $^1$H NMR (300 MHz, CDCl$_3$) of the free base δ 1.48–1.65 (m, 1H), 1.72–1.87 (m, 1H), 2.20–2.33 (m, 2H), 2.52–2.71 (m, 3H), 2.86–3.00 (m, 1H), 3.08–3.21 (m, 1H), 3.42–3.57 (m, 1H), 3.73–3.90 (m, 2H), 3.81 (s, 3H), 4.16–4.42 (m, 6H), 6.18 (s, 1H), 6.66 (d, 1H), 6.79 (d, 1H), 7.09 (t, 1H), 7.28 (s, 114). MS (DCI/NH$_3$) m/e 450 (M+H)$^+$. Anal calcd for C$_{25}$H$_{27}$N$_3$O$_5$·HCl·0.5 H$_2$O: C, 60.66; H, 5.91; N, 8.49. Found: C, 60.69; H, 5.73; N, 8.37.

EXAMPLE 39

3-[2-((3aR,9bR)-cis-6-Methoxy-2,3,3a,4,5,9b-hexahydro-[1H]-benz[e]isoindol-1-yl)ethyl]-6,7-dimethoxyquinazoline-2,4(1H,3H)-dione hydrochloride The compound resulting from Example 13J (2.44, 0.6 g) was reacted with 0.7 g of the isocyanate derived from methyl 2-amino-4,5-dimethoxy-benzoate as in Example 10 to yield 0.6 g (54%) of the title compound. $^1$H NMR (300 MHz, DMSO-d$_6$) δ 7.36 (s, 1H), 7.18 (t, 1H), 6.81 (s, 1H), 6.85 (d, 1H), 6.75 (d, 1H), 4.2–4.32 (m, 3H), 3.9–4.1 (m, 1H), 3.88 (s, 3H), 3.84 (s, 3H), 3.8 (s, 3H), 3.65 (m, 1H), 3.42 (m, 3H), 2.92–3.6 (m, 2H), 2.6–2.85 (m, 2H), 1.73–1.88 (m, 1H), 1.52–1.68 (m, 1H). Anal calcd for C$_{25}$H$_{29}$N$_3$O$_5$·HCl·H$_2$O: C, 59.34; H, 6.37; N, 8.30. Found: C, 59.73; H, 6.20; N, 8.23.

EXAMPLE 40

3-[2-((3aR,9bR)-cis-6-Methoxy-2,3,3a,4,5,9b-hexahydro-[1H]-benz[e]isoindol-1-yl)ethyl]-1-methyl-6,7-dimethoxyquinazoline-2,4(1H,3H)-dione hydrochloride The compound resulting from Example 13J (203 mg, 1 mmol) and 0.3 g (1.05 mmol) 6,7-dimethohy-1-methyl-quinazoline-2,4-dione were reacted as described in Example 26 to yield 0.235 g (64%) of the title compound as a white solid. m.p. 188°–190° C. $^1$H NMR (300 MHz, CDCl$_3$) of the free base δ 7.61 (s, 1H), 7.1 (t, 1H), 6.78 (d, 1H), 6.66 (d, 1H), 6.58 (s, 1H), 4.25 (t, 2H), 4.02 (s, 3H), 3.95 (s, 3H), 3.81 (s, 3H), 3.6 (s, 3H), 3.42 (m, 3H), 2.48–2.87 (m, 5H), 2.28 (m, 2H), 1.75 (m, 1H), 1.52 (m, 1H). Anal calcd for C$_{25}$H$_{29}$N$_3$O$_5$·HCl·H$_2$O: C, 60.05; H, 6.59; N, 8.08. Found: C, 59.51; H, 6.36; N, 7.93.

EXAMPLE 41

3-[2-(cis-6-Methoxy-2,3,3a,4,5,9b-hexahydro-[1H]-benz[e]isoindol-1-yl)ethyl]-6-methoxy-thieno[2,3-d]pyrimidine-2,4(1H,3H)-dione hydrochloride

EXAMPLE 41A

5Amino-carboethoxy-2-methoxythiophene

To methanol (404 µL, 10 mmol) in THF (10 mL) at 0° C. under nitrogen was added 2.5M n-BuLi (4.0 mL, 10 mmol). After stirring 20 minutes, CS$_2$ (600 µL, 10 mmol) was added and stirring was continued for 4 hours. The reaction was then cooled to 0° C. followed by the addition of MeI (620 µL, 10 mmol) whereupon the reaction was stirred for 4 hours at 0° C. then at ambient temperature overnight. In a separate flask the anion of acetonitrile was prepared by the dropwise addition of acetonitrile (520 µL, 10 mmol) to a solution of LDA (10 mmol) in THF at −78° C. followed by stirring for 30 minutes at that temperature. To the acetonitrile anion was added the solution of the xanthate prepared above. The reaction was stirred for 1 hour at −78° C. then 1 hour at 0° C. The reaction was then cooled to −78° C., treated with ethyl bromoacetate (1.1 mL, 10 mmol), warmed to reflux, treated with 1.0M lithium bistrimethylsilylamide (1 mL) and heated at reflux for 1.5 hours. After cooling the reaction, it was partitioned between saturated NaHCO$_3$ solution and methylene chloride. The organic layer was then dried with sodium sulfate, filtered, concentrated in vacuo and flash chromatographed eluting with 4:1 hexane-ethyl acetate to give 343 mg (17% yield) of the title compound.

EXAMPLE 41B

3-[2-(cis-6-Methoxy-2,3,3a,4,5,9b-hexahydro-[1H]-benz[e]isoindol-1-yl)ethyl]-6-methoxy-thieno[2,3-d]pyrimidine-2,4(1H,3H)-dione hydrochloride The compound resulting from Example 41A (303 mg) was reacted according to the standard procedure for in situ isocyanate formation with the compound resulting from Example 13J (0.375 g, 1.52 mmol) to give 240 mg (38%) of product as the free base which was converted to the fumarate salt giving 149 mg (18%). m.p. 217° C. $^1$H NMR (300 MHz, DMSO-d$_6$) δ 1.45 (1H, m), 1.65 (1H, m), 2.23 (1H, m), 2.32 (1H, m), 2.44 (2H, m), 2.58 (1H, m), 2.66 (2H, m), 3.30 (3H, m), 3.75 (3H, s), 3.95 (2H, t), 3.99 (3H, s), 6.10 (1H, s), 6.59 (2H, s), 6.72 (1H, d), 6.75 (1H, d), 7.09 (1H, t), 11.76 (1H, br s). Anal calcd for C$_{26}$H$_{29}$N$_3$O$_8$S: C, 57.45; H, 5.38; N, 7.73. Found: C, 57.17; H, 5.23; N, 7.63.

EXAMPLE 42

3-[2-((3aR,9bR)-cis-6-Methoxy-2,3,3a,4,5,9b-hexahydro-[1H]-benz[e]isoindol-1-yl)ethyl]-6,7-dimethoxy-quinazoline-4(3H)-one dihydrochloride Ethyl 2-(N,N-dimethyl-N'-formamidinyl)-3,4dimethoxybenzoate (5.67 g, 20.3 mmol), prepared according to the method described by Gupton J. T., Miller J. F., Bryant R. D. Maloney P. R., Foster B. S. in Tetrahedron 43(8) 1747–1752 (1987) from ethyl 6-amino-3,4-dimethoxybenzoate, and The compound resulting from Example 13J (2.0 g, 8.1 mmol) refluxing in a solution of 1,4-dioxane (30 mL) and p-toluenesulfonic acid monohydrate (0.15 g, 0.8 mmol) for 4 hours. The reaction mixture was concentrated to a crude oil which was recrystallized from MeOH to give the product as the free base. The free base was dissolved in methylene chloride and treated with HCl in Et$_2$O to yield the title compound (3.59 g, 87%) as a white solid. m.p. 180°–185° C. (on a sample recrystallized from EtOH-Et$_2$O). $^1$H NMR (300 MHz, D$_2$O) δ 8.31 (s, 1H), 7.42 (br s, 1H), 7.24 (t, J=7.9 Hz, 1H), 7.08 (s, 1H), 6.94–6.89 (d, 1H), 6.91–6.87 (d, 1H), 4.72 (s, 3H), 4.45 (t, J=6.5 Hz, 2H), 3.98 (s, 3H), 3.93 (s, 3H), 3.83 (s, 3H), 3.70 (br s, 3H), 3.22–3.10 (br s, 1H), 2.85–2.74 (m, 2H), 2.62–2.51 (m, 1H), 1.97–1.90 (m, 1H), 1.66–1.62 (m, 1H). MS (DCI/NH$_3$) m/e 436 (M+H)$^+$. [α]$_D$=+27.40° (c=0.53, CH$_3$OH). Anal. calcd for C$_{25}$C$_{29}$N$_3$O$_4$·0.1 HCl·0.8 H$_2$O: C, 57.03; H, 6.26; N, 7.98. Found: C, 57.10; H, 6.25; N, 7.93.

EXAMPLE 43

3-[2-((3aR,9bR)-cis-6-Methoxy-2,3,3a,4,5,9b-hexahydro-[1H]-benz[e]isoindol-1-yl)ethyl]-thieno[2,3-d]pyrimidine-4(3H)-one dihydrochloride 3-[(N,N-Dimethyl-N'-formamidinyl)]carboxyethylthiophene was prepared from 3-(2-amino)-carboxyethylthiophene by the method described in Gupton J. T., Miller J. F., Bryant R. D. Maloney P. R., Foster B. S., Tetrahedron 43(8) 1747–1752 (1987).

3-[(N,N-Dimethyl-N'-formamidinyl)]-carboxyethylthiophene (0.92 g, 4.1 mmol) and the compound resulting from Example 13J (0.40 g, 1.6 mmol) were heated under reflux in a solution of 1,4-dioxane (6.0 mL) and p-toluenesulfonic acid monohydrate (0.03 g, 0.2 mmol) for 3 hours. The reaction mixture was concentrated and then purified by flash column chromatography on silica gel eluting with EtOAc to give free base as an oil. The free base was dissolved in methylene chloride and treated with HCl(g) in Et$_2$O to yield the title compound (0.16 g, 22%) as a solid. m.p. 171°–175° C. (on a sample recrystallized from MeOH-Et$_2$O). $^1$H NMR (300 MHz, DMSO-d$_6$) δ 8.50 (br s, 1H), 7.64–7.62 (d, 1H), 7.44–7.42 (d, 1H), 7.16 (t, J=9.5 Hz), 6.84–6.81 (d, 1H), 6.78–6.76 (d, 1H), 4.45–4.30 (br s, 2H), 4.13 (br s, 1H), 4.00 (br s, 1H), 3.77 (s, 3H), 3.70–3.45 (m, 3H), 3.01 (br s, 1H), 2.72–2.67 (m, 2H), 2.50–2.38 (m, 2H), 1.76 (br s, 1H), 1.60 (br s, 1H), MS (DCI/NH$_3$) m/e 882 (M+H)$^+$, $|\alpha|_D$=+19.1° (c=0.35, CH$_3$OH). Anal. calcd for C$_{21}$H$_{23}$N$_3$O$_2$S·0.1 H$_2$O: C, 55.28; H, 6.56; N, 9.21. Found: C, 55.33; H, 5.72; N, 9.02.

EXAMPLE 44

3-[2-((3aR,9bR)-cis-6-Methoxy-2,3,3a,4,5,9b-hexahydro-[1H]-benz[e]isoindol-1-yl)ethyl]-quinazoline-2(1H)-one hydrochloride 2-[2-((3aR,9bR)-cis-6-Methoxy-2,3,3a,4,5,9b-hexahydro-[1H]-benz[e]isoindol-1-yl)ethyl]aminomethyl aniline was prepared from 2-nitrobenzyl bromide and the compound resulting from Example 13J using stannous chloride dihydrate in methanol by the procedure of Langley D. R. and Thurston. D. E, *J. Org. Chem.* 52 (1), 91–97 (1987).

The above prepared compound (136 mg, 0.387 mmol) in 4 mL of dry tetrahydrofuran was cooled in an ice bath, and a solution of 75.3 mg (0.464 mmol) of N,N'-carbonyldiimidazole in 2 mL of dry tetrahydrofuran was added rapidly with stirring. The cooling bath was removed and stirring was continued for 3 hours. The solvent was evaporated to give the crude product Chromatography on silca gel eluting with 3% MeOH in CHCl$_3$ afforded the product as a free base. The free base was dissolved in methylene chloride and treated with a solution of HCl(g) dissolved in Et$_2$O to give the title compound (45 mg) as a white solid. m.p. 145°–147° C. (on a sample recrystallized from EtOH-Et$_2$O). $^1$H NMR (300 MHz, CD$_3$OD) δ 1.30 (m,1H), 1.55–1.70 (m, 3H), 2.20(m, 2H), 2.52–2.65 (m, 4H), 2.72 (m, 2H), 3.25 (m, 1H), 3.35 (s, 2H), 3.42 (m, 1H), 3.82 (s, 3H), 6.70 (m, 4H), 7.20 (m, 3H) MS (DCI/NH$_3$) m/e 378 (M+H)$^+$. Anal. calcd for C$_{23}$H$_{27}$N$_3$O$_2$·0.90 HCl: C, 61.83; H, 6.52; N, 9.41. Found: C, 61.91; H, 6.46; N, 9.29.

EXAMPLE 45

3-[2-(cis-6-Methoxy-2,3,3a,4,5,9b-hexahydro-[1H]-benz[e]isoindol-1-yl)ethyl]-12-dihydroquinazoline4(3H)-one dihydrochloride The compound resulting from Example 34 (0.15 g, 0.3 mmol) in methanol (25 mL) was hydrogenated at 4 atmosphere of H$_2$ at room temperature using a 10% Pd/C catalyst (dry, 0.02 g) for 17 hours. The catalyst was removed by filtrated and the filtrate concentrated. The residue obtained was dissolved in water, basified to pH 13 with potassium carbonate and extracted with Et$_2$O and EtOAc. The combined organic extracts were dried over anhydrous Na$_2$SO$_4$ and concentrated to give, after flash column chromatography eluting with 10:90 EtOH-EtOAc, the free base as a white solid. The free base was dissolved in methylene chloride treated with a solution of HCl(g) dissolved in Et$_2$O to give the title compound (0.05 g, 37%) as a white solid. m.p. 130° C. (dec). $^1$H NMR (300 MHz, CD$_3$OD) δ 7.81 (dd, J=1.5 Hz, 1H), 7.79–7.78 (dd, J=1.3 Hz, 1H), 7.3–7.31 (m, 1H), 7.16 (t, J=8.1 Hz, 1H), 6.86–6.77 (m, 4H), 4.69 (s, 2H), 4.29–4.13 (m, 2H), 3.88–3.72 (m, 2H), 3.81 (s, 3H), 3.64–3.45 (m, 4H), 3.143.03 (m, 2H), 2.87–2.78 (m, 2H), 2.58–2.56 (m, 1H), 1.94–1.89 (m, 1H), 1.69–1.65 (m, 1H). MS (DCI/NH$_3$) m/e378 (M+H)$^+$. Anal. calcd for C$_{23}$H$_{27}$N$_3$O$_2$·0.1 HCl·0.8 H$_2$O: C, 58.97; H, 6.60; N, 8.97. Found: C, 59.06; H, 6.65; N, 8.59.

EXAMPLE 46

3-[2-((3aR,9bR)-cis-6-Methoxy-2,3,3a,4,5,9b-hexahydro-[1H]-benz[e]isoindol-1-yl)ethyl]-7-carbamylquinazoline-2,4(1H,3H)-dione hydrochloride

EXAMPLE 46A

2-Amino-4-carbamylbenzoic acid 2-amino-4Cyanobenzoic acid (3.01 g, 18.3 mmol), prepared by the method of Chan and Bruice, *J. Am. Chem. Soc.*, 99: 6721 (1977), was dissolved in 60 mL of 97% H$_2$SO$_4$ and heated to 45° C. for 12 h. The mixture was added to ice, and saturated Na$_2$CO$_3$ solution was added to adjust the pH=3. The mixture was then filtered, and the yellow solid lyophilized to yield the title compound (2.94 g, 89%): mp 276°–278° C. $^1$H NMR (300 MHz, DMSO-d$_6$) δ 8.72 (br s, 3H), 7.90 (br s, 1H), 7.71 (d, 1H), 7.37 (br s, 1H), 7.21 (d, 1H), 6.92 (dd, 1H), 6.75 (br s, 2H); MS (DCI/NH$_3$) m/z 181 (M+H)$^+$.

EXAMPLE 46B

Methyl 2-amino-4-carbamylbenzoate

The product from Example 46A (1.44 g, 8 mmol) was dissolved in 25 mL DMF and Me$_2$SO$_4$ (0.757 mL, 8 mmol) and Et$_3$N (1.23 mL, 8.8 mmol) were added. The reaction was stirred at room temperature for 24 hours, poured into brine, and extracted with 5x EtOAc. The extracts were washed with NaHCO$_3$ solution and brine, dried over MgSO$_4$, and the solvent evaporated. The residue was chromatographed on SiO$_2$ with EtOAc to yield the title compound (0.48 g, 31%): $^1$H NMR (300 MHz, DMSO-d$_6$) δ 7.91 (br s, 1H), 7.72 (d, 1H), 7.39 (br s, 1H), 7.24 (d, 1H), 6.93 (dd, 1H), 6.75 (br s, 2H), 3.80 (s, 3H); MS (DCI/NH$_3$) m/z 195 (M+H)$^+$.

EXAMPLE 46C

3-[2-((3aR,9bR)-cis-6-Methoxy-2,3,3a,4,5,9b-hexahydro-[1H]-benz[e]isoindol-1-yl)ethyl]-7-carbamylquinazoline-2,4(1H,3H)-dione hydrochloride The product from Example 46B was treated with 0.33 equivalent triphosgene by the procedure described in Example 1C. The resulting isocyanate (0.40 g, 1.83 mmol) and the compound resulting from Example 13J (0.43 g, 1.74 mmol) were treated by the procedure described in Example 1C to yield the free base of the title compound which was chromatographed on SiO$_2$ using 18:1:1 EtOAc/HCOOH/water as eluent. The formic acid salt thus obtained was converted to the HCl salt, yielding the title compound (0.12 g, 15%): mp >300° C.; $^1$H NMR (300 MHz, DMSO-d$_6$) δ 11.75 (d, 1H), 10.51 (s, 1H), 8.22 (s, 1H), 8.00 (t, 1H), 7.67 (m, 3H), 7.18 (t, 1H), 6.71–6.86 (m, 2H), 4.26 (m, 2H), 4.12 (m, 1H), 4.01 (m, 1H), 3.79 (s, 3H), 3.50 (m, 2H), 3.02 (m, 1H), 2.55–2.82 (m, 3H), 1.79 (m, 2H), 1.60 (m, 2H); MS (DCI/NH$_3$) m/z 435 (M+H)$^+$. Anal. calcd for C$_{24}$H$_{27}$ClN$_4$O$_4$·HCl: C, 56.81; H, 5.56; N, 11.04. Found: C, 56.42; H, 5.32; N, 10.79.

EXAMPLE 47

3-[2-((3aR,9bR)-cis-6-Methoxy-2,3,3a,4,5,9b-hexahydro-[1H]-benz[e]isoindol-1-yl)ethyl]-7-(N,N'-dimethyl)carbamylguinazoline-2,4(1H,3H)-dione hydrochloride

EXAMPLE 47A

Methyl 2-amino-4-(N,N'-dimethyl)carbamylbenzoate

Methyl 2-amino-4carbamylbenzoate (0.94 g, 4.84 mmol) was added to a suspension of KOH (2.17 g, 38.7 mmol) in DMSO (15 mL). Iodomethane (1.05 mL, 16.9 mmol) was then added, and the reaction was stirred for 5 min, and poured into water (150 mL). The solution was extracted with 3x CH$_2$Cl$_2$, and the extracts were washed with 2xwater, dried over MgSO$_4$, and evaporated. The residue was chromatographed on SiO$_2$ using 4% MeOH/CH$_2$Cl$_2$ as eluent, to yield the title compound (0.66 g, 67%): $^1$H NMR (300 MHz, DMSO-d6) δ 7.72 (d, 1H), 6.78 (br s, 2H), 6.74 (d, 1H), 6.48

(dd, 1H), 3.80 (s, 3H), 2.96 (br s, 3H), 2.87 (br s, 3H); MS (DCI/NH₃) m/z 223 (M+H)⁺.

EXAMPLE 47B
3-|2-((3aR ,9bR)-cis-6-Methoxy-2,3,3a,4,5,9b-hexahydro-|1H|-benz[e]isoindol-1-yl)ethyl|-7-(N,N'-dimethyl) carbamylguinazoline-2,4(1H,3H)-dione hydrochloride Methyl 2-amino4(N,N'-dimethyl)carbamylbenzoate was treated with 0.33 equivalent triphosgene by the procedures described in Example 1C. The resulting isocyanate (0.49 g, 1.95 mmol) and the compound resulting from Example 13J (0.44 g, 1.8 mmol) were treated by the procedures described in Example 1C to yield the free base of the tide compound which was chromatographed on SiO₂ using 18:1:1 EtOAc/HCOOH/water as eluent. The formic acid salt thus obtained was converted to the HCl salt, yielding the title compound (0.13 g, 14%): mp >300° C. ¹H NMR (300 MHz, DMSO-d6) δ 11.81 (d, 1H), 11.25 (s, 1H), 7.96 (dd, 1H), 7.12–7.25 (m, 3H), 6.72–6.86 (m, 2H), 4.26 (m, 2H), 4.12 (m, 1H), 4.00 (m, 1H), 3.78 (s, 3H), 3.48 (m, 2H), 3.01 (s, 3H), 2.96 (m, 1H), 2.87 (s, 3H), 2.50–2.80 (m, 3H), 1.79 (m, 2H), 1.62 (m, 2H). MS (DCI/NH₃) m/z 463 (M+H)⁺. Anal. calcd for C₂₆H₃₁ClN₄O₄·0.9HCl: C, 58.73; H, 6.10; N, 10.28. Found: C, 58.82; H, 6.17; N, 10.33.

EXAMPLE 48
3-[2-((3aR ,9bR)-cis-6-Methoxy-2,3,3a,4,5,9b-hexahydro-[1H]-benz[e]isoindol-1-yl)ethyl]-6,8-dichloro-7-methoxyquinazoline-2,4(1H,3H)-dione hydrochloride

EXAMPLE 48A
Methyl 2-Amino-3,5Dichloro-4-methoxybenzoate

Chlorination of methyl 2-amino-4-methoxybenzoate according to the procedure of Hess, et al (U.S. Pat. No. 4,287,341) gave the title compound: mp 72°–73° C.; ¹H NMR (300 MHz, CDCl₃) δ 3.86 (s, 3H), 3.92 (s, 3H), 6.33 (bs, 2H), 7.86 (s, 1H); MS (DCI/NH₃) m/z 250 (M+H)⁺.

EXAMPLE 48B
3-[2-((3aR ,9bR)-cis-6-Methoxy-2,3,3a,4,5,9b-hexahydro-[1H]-benz[e]isoindol-1-yl)ethyl]-6,8-dichloro-7-methoxyquinazoline-2,4(1H,3H)-dione hydrochloride The product from Example 48A (498 mg, 2.0 mmol) was converted to the corresponding isocyanate by treatment with triphosgene as described in Example 1C. The resulting isocyanate (2.0 mmol) and the product from Example 13J (492 mg, 2.0 mmol) were refluxed in 30 mL of toluene for 16 h and concentrated. The residue was triturated with EtOAc and filtered to give the free base which upon treatment with methanolic HCl gave the title compound as a tan solid (41%): mp 229°–233° C.; ¹H NMR (300 MHz, DMSO-d6) δ 1.54–1.68 (m, 1H), 1.70–1.85 (m, 1H), 2.43–2.53 (m, 1H), 2.55–2.82 (m, 3H), 2.93–3.10 (m, 1H), 3.40–3.55 (m, 3H), 3.77 (s, 3H), 3.91 (s, 3H), 3.97–4.15 (m, 2H), 4.19–4.28 (m, 2H), 6.73 (d, 1H), 6.83 (d, 1H), 7.17 (t, 1H), 7.98 (s, 1H), 10.86 (s, 1H), 11.32 (s, 1H). MS (DCI/NH₃) m/z 490 (M+H)⁺. Anal. calcd for C₂₄H₂₆Cl₃N₃O₄·H₂O: C, 52.91; H, 5.18; N, 7.71. Found: C, 52.82; H, 4.81; N, 7.59.

EXAMPLE 49
3-[2-((3aR ,9bR)-cis-6-Methoxy-2,3,3a,4,5,9b-hexahydro-[1H]-benz[e]isoindol-1-yl)ethyl]-7-chloro-6-methoxyquinazoline-2,4(1H,3H)-dione hydrochloride

EXAMPLE 49A
Methyl 2-Amino-4-chloro-5-methoxybenzoate

A solution of 2-amino-4chloro-5-methoxybenzoic acid (3.0 g, 15.0 mmol; prepared according to the procedure of Denny, et al., *J. Med. Chem.* 34:217–222 (1991)) in 70 ml MeOH was treated with excess trimethylsilyl diazomethane. The solution was concentrated and the residue flash chromatographed on silica (9:1 hexane/EtOAc to give the title compound (46%): mp 63°–64° C.; ¹H NMR (300 MHz, CDCl₃) δ 6 3.83 (s, 3H), 3.90 (s, 3H), 5.48 (bs, 2H), 6.75 (s, 1H), 7.39 (s, 1H); MS (DCI/NH₃) m/z 216 (M+H)⁺.

EXAMPLE 49B
3-|2-((3aR ,9bR)-cis-6-Methoxy-2,3,3a,4,5,9b-hexahydro-|1H|-benz[e]isoindol-1-yl)ethyl|-7-chloro-6-methoxyquinazoline-2,4(1H,3H)-dione hydrochloride The product from Example 49A (387 mg, 1.8 mmol) was converted to the corresponding isocyanate by treatment with 0.33 eq of triphosgene as described in Example 1C. The resulting isocyanate (2.0 mmol) and the product from Example 13J (440 mg, 1.8 mmol) were refluxed in 30 mL of toluene for 16h and concentrated. The residue was triturated with EtOAc and filtered to give the free base which upon treatment with methanolic HCl gave the title compound (550 mg, 62%): mp 252°–256° C.; ¹H NMR (300 MHz, DMSO-d6) d 1.52–1.68 (m, 1H), 1.70–1.85 (m, 1H), 2.43–2.53 (m, 1H), 2.55–2.82 (m, 3H), 2.95–3.08 (m, 1H), 3.40–3.55 (m, 3H), 3.77 (s, 3H), 3.91 (s, 3H), 3.94–4.15 (m, 2H), 4.19–4.32 (m, 2H), 6.73–6.88 (m, 2H), 7.17 (t, 1H), 7.33 (s, 1H), 7.50 (s, 1H), 10.48 (s, 1H), 11.60 (s, 1H); MS (DCI/NH₃) m/z 456 (M+H)⁺. Anal. calcd for C₂₄H₂₇Cl₂N₃O₄·0.3 H₂O: C, 57.91; H, 5.59; N, 8.44. Found: C, 57.89; H, 5.58; N, 8.31.

EXAMPLE 50
3-[2-((3aR ,9bR)-cis-6-Methoxy-2,3,3a,4,5,9b-hexahydro-|1H|-benz[e]isoindol-1-yl)ethyl]-1-methyl -7-methoxyquinazoline-2,4(1H,3H)-dione hydrochloride

EXAMPLE 50A
Methyl 2-formamido-4-methoxy benzoate

A mixture of acetic anhydride (7.15 g, 70 mmol) and formic acid was heated at 65° C. for 2 h, cooled and added to a solution of methyl 2-amino-4-methoxybenzoate (2.5 g, 13.8 mmol) (U.S. Pat. No. 4,287,341) in 10 mL THF. The solution was stirred for 4h and concentrated to give the title compound in quantitative yield. ¹H NMR (300 MHz, CDCl₃) δ 3.88 (s, 3H), 3.91 (s, 3H), 6.64 (dd, J=9.3Hz, 1H), 7.97 (d, J=9 Hz, 1H), 8.36 (d, J=3 Hz, 1H), 8.52 (d, J=2 Hz, 1H), 11.18 (bs, 1H); MS (DCI/NH₃) m/z 227 (M+NH₄)⁺.

EXAMPLE 50B
Methyl 2-aminomethyltmethoxy benzoate

The product from Example 50A (2.85 g, 13.6 mmol) in 25 mL THF at 0° C. was treated with BH₃·SMe₂ (32 mmol). The solution was stirred for 2 h at 25° C. and carefully treated with methanol. The resulting solution was concentrated and the residue treated with TMEDA in THF. This solution was partitioned between EtOAc and 10% aq sodium bicarbonate. The organic layer was washed with brine, dried MgSO₄, and concentrated. Flash chromatography on silica gel (9:1 hexane/EtOAc) gave the title compound in 55% yield. ¹H NMR (300 MHz, CDCl₃) δ 2.89 (d, J=5 Hz, 3H), 3.82 (s, 3H), 3.85 (s, 3H), 6.09 (d, J=3 Hz, 1H), 6.17 (dd, J=9,3 Hz, 1H), 7.73 (bs, 1H), 7.83 (d, J=9 Hz, 1H); MS (DCI/NH₃) m/z 196 (M+H)⁺.

EXAMPLE 50C
1-Methyl-7-methoxy benzoxazine-2,4(1)H-dione

To the product from Example 50B (390 mg, 2.0 mmol) and Et3N (400 mg, 4.5 mmol) in 40 mL dichloromethane at −78° C. under nitrogen was added dropwise 1.93M phosgene (4.0 mmol). The soln was stirred at 25° C. for 16 h and partitioned with brine. The methylene chloride layer was dried (MgSO₄) and concentrated to give the title compound as a white solid, quantitative yield: $^1$H NMR (300 MHz, DMSO-d6) δ 3.48 (s, 3H), 3.93 (s, 3H), 6.85 (d, J=3 Hz, 1H), 6.92 (dd, J=9.3 Hz, 1H), 7.93 (d, J=9 Hz, 1H); MS (DCI/NH₃) m/z 225 (M+NH4)⁺.

EXAMPLE 50D
3-[2-((3aR .9bR)-cis-6-Methoxy-2,3,3a,4,5,9b-hexahydro-[1H]-benz[e]isoindol-1-yl)ethyl]-1-methyl-7-methoxyquinazoline-2,4(1H,3H)-dione hydrochloride The product from Example 50C (410 mg, 1.98 mmol) and the product from Example 13J were refluxed in 30 mL of toluene for 16 h, cooled and concentrated to give the intermediate benzamide. To the crude benzamide (547 mg, 1.34 mmol) and triethylamine (400 mg, 4.5 mmol) in 20 mL toluene at −78° C. under nitrogen was added dropwise 1.93M phosgene (1.5 mmol). The solution was warmed to 25° C. and then heated to reflux for 16 h. The reaction mixture was concentrated and the residue was flash chromatographed on silica gel (18:1:1 EtOAc/water/formic acid). Treatment with methanolic HCl gave the desired product in 15% yield: mp 248°–249° C.; $^1$H NMR (300 MHz, DMSO-d6) δ 1.52–1.68 (m, 1H), 1.70–1.85 (m, 1H), 2.33–2.53 (m, 1H), 2.55–2.85 (m, 2H), 2.95–3.08 (m, 1H), 3.40–3.60 (m, 4H), 3.52 (s, 3H), 3.77 (s, 3H), 3.91 (s, 3H), 3.94–4.15 (m, 2H), 4.19–4.3 (m, 2H), 6.71–6.93 (m, 4H), 7.17 (t, 1H), 7.98 (d, 1H), 10.74 (s, 1H); MS (DCI/NH₃) m/z 436 (M+H)⁺. Anal. calcd for $C_{25}H_{30}ClN_3O_4 \cdot H_2O$: C, 61.38; H, 6.58; N, 8.58. Found: C, 61.77; H, 6.41; N, 8.53.

EXAMPLE 51
3-[2-((3aR .9bR)-cis-6-Methoxy-2,3,3a,4,5,9b-hexahydro-[1H]-benz[e]isoindol-1-yl)ethyl]-1-methyl-6-chloro-7-methoxyquinazoline-2,4(1H,3H)-dione hydrochloride

EXAMPLE 51A
Methyl 2-chloro-5-formamido-3-methoxybenzoate

The formamide was prepared in quantitative yield from methyl 2-amino-methoxy-5-chlorobenzoate (U.S. Pat. No. 4,287,341) as described in Example 50C. $^1$H NMR (300 MHz, CDCl₃) δ 3.92 (s, 3H), 4.00 (s, 3H), 8.05 (s, 1H), 8.51 (s, 1H), 8.53 (d, J=2 Hz, 1H), 11.17 (bs, 1H); MS (DCI/NH₃) m/z 261 (M+NH₄)⁺.

EXAMPLE 51B
Methyl 2-aminomethyl-5-chloro-4-methoxy-benzoate

Borane reduction of the product from Example 51A as described previously in Example 50B followed by flash chromatography (9:1 hexane/EtOAc) gave 700 mg (52%) of the title compound: $^1$H NMR (300 MHz, CDCl₃) δ 2.92 (d, J=6 Hz, 3H), 3.82 (s, 3H), 3.94 (s, 3H), 6.09 (s, 1H), 7.81 (bs, 1H), 7.88 (s, 1H MS (DCI/NH₃) m/z 230 (M+H)⁺.

EXAMPLE 51C
1-Methyl-6-chloro-7-methoxy Benzoxazine-2,4(1H)-dione

The product from Example 51B was treated as described in Example 50C to give 500 mg (quantataive yield) of the title compound: $^1$H NMR (300 MHz, DMSO-d6) δ 3.51 (s, 3H), 4.08 (s, 3H), 6.97 (s, 1H), 7.95 (s, 1H); MS (DCI/NH₃) m/z 259 (M+NH₄)⁺.

EXAMPLE 51D
N-[2-((3aR,9bR)-cis-6-Methoxy-2,3,3a,4,5,9b-hexahydro-[1H]-benz[e]isoindol-1-yl)ethyl]-2-aminomethyl-5-chloro-4-methoxy benzamide The product from Example 51C (410 mg, 1.98 mmol) and the product from Example 13J were refluxed in 30 mL of toluene for 16 h, cooled and concentrated to give the intermediate benzamide which was flash chromatographed on silica gel (18:1:1 EtOAc/water/formic acid) to yield the title compound (760 mg, 86%): $^1$H NMR (300 MHz, DMSO-d6) δ 1.40–1.50 (m, 1H), 1.60–1.72 (m, 1H), 2.12–2.29 (m, 2H), 2.40–2.52 (m, 1H), 2.52–2.66 (m, 3H), 2.81 (d, J=6 Hz, 3H) 3.20 (m, 1H), 3.30 (m, 5H), 3.73 (s, 3H), 3.89 (s, 3H), 6.22 (s, 1H), 6.72 (d, J=9 Hz, 1H), 6.73 (d, J=9 Hz, 1H), 7.08 (dd, J=9.9 Hz, 1H), 7.63 (s, 1H), 8.10–8.26 (m, 2H); MS (DCI/NH₃) m/z 444 (M+H)⁺.

EXAMPLE 51E
3-[2-((3aR .9bR)-cis-6-Methoxy-2,3,3a,4,5,9b-hexahydro-[1H]-benz[e]isoindol-1-yl)ethyl]-1-methyl-6-chloro-7-methoxyquinazoline-2,4(1H,3H)-dione hydrochloride To the product from Example 51D (760 mg, 1.7 mmol) and triethylamine (500 mg, 5.0 mmol) in 20 mL toluene at −78° C. under nitrogen was added dropwise 1.93M phosgene (2.0 mmol). The soln was warmed to 25° C. and stirred for 16 h. The reaction mixture was concentrated and the residue was flash chromatographed on silica gel (18:1:1 EtOAc/water/formic acid). Treatment with methanolic HCl gave the title compound (480 mg,53%): mp 181°–186° C.; $^1$H NMR (300 MHz, DMSO-d₆) δ 1.52–1.68 (m, 1H), 1.70–1.85 (m, 1H), 2.33–2.53 (m, 1H), 2.55–285 (m, 3H), 2.95–3.08 (m, 1H), 3.40–3.55 (m, 3H), 3.58 (s, 3H), 3.77 (s, 3H), 3.94–4.15 (m, 2H), 4.07 (s, 3H), 4.19–4.35 (m, 2H), 6.73 (d, 1H), 6.84 (d, 1H), 7.02 (s, 1H), 7.17 (t, 1H), 7.98 (s, 1H), 10.74 (s, 1H); MS (DCI/NH₃) m/z 470 (M+H)⁺. Anal. calcd for $C_{25}H_{29}Cl_2N_3O_4 \cdot 1.25\ H_2O$: C, 56.77; H, 6.00; N, 7.94. Found: C, 56.74; H, 5.78; N, 7.67.

EXAMPLE 52
3-[2-((3aR .9bR)-cis-6-Methoxy-2,3,3a,4,5,9b-hexahydro-[1H]-benz[e]isoindol-1-yl)ethyl]-1-(2-methoxyethyl)-6,7-dimethox quinazoline-2,4(1H,3H)-dione hydrochloride

EXAMPLE 52A
Methyl-2-[(2-methoxyethyl)amino]-4,5-dimethoxy benzoate

Methy-2-amino-4,5-dimethoxybenzoate (2.1 g, 10 mmol), methoxyacetaldehyde (11 mmol), NaCNBH₃ (15 mmol) and acetic acid (10 mmol) were combined in 20 mL MeOH and stirred for 72 h. The reaction mixture was filtered through Celite, concentrated and the residue partitioned between water and EtOAc. The EtOAc layer was dried (MgSO₄) and concentrated to give the title compound (46%): $^1$H NMR (300 MHz, CDCl₃) δ 3.40 (dt, J=6,1 Hz, 2H), 3.43 (s, 3H), 3.65 (t, J=6 Hz, 2H), 3.82 (s, 3H), 3.83 (s, 3H), 3.91 (s, 3H), 6.21 (s, 1H), 7.38 (s, 1H), 7.80 (t, J=1 Hz, 1H); MS (DCI/NH₃) m/z 270 (M+H)⁺.

EXAMPLE 52B
1-(2-methoxyethyl)-6,7-dimethoxy Benzoxazine-2,4(1H)-dione

The product from Example 52A was treated as described in Example 50C to yield the title compound (96%): $^1$H NMR (300 MHz, CDCl₃) δ 3.35 (s, 3H), 3.76 (t, J=6 Hz, 2H), 3.93 (s, 3H), 4.00 (s, 3H), 4.23 (t, J=6 Hz, 2H), 6.93 (s, 1H), 7.45 (s, 1H); MS (DCI/NH₃) m/z 299 (M+NH₄)⁺.

EXAMPLE 52C
3-[2-((3aR .9bR)-cis-6-Methoxy-2,3,3a,4,5,9b-hexahydro-[1H]-benz[e]isoindol-1-yl)ethyl]-1-(2-methoxyethyl)-6,7-dimethoxyquinazoline-2,4(1H,3H)-dione hydrochloride The product from Example 52B (520 mg, 1.85 mmol) and the product from Example 13J were refluxed in 30 mL of toluene for 16 h, cooled and concentrated to give the intermediate benzamide. To the crude benzamide (560mg, 1.16 mmol) and triethylamine (300 mg, 3.0 mmol) in 20 mL toluene at −78° C. under nitrogen was added dropwise 1.93M phosgene (1.4 mmol). The solution was warmed to 25° C. and then heated to reflux for 16 h. The reaction mixture was concentrated and the residue was flash chromatographed on silica gel (8:1:1 EtOAc/water/formic acid). Treatment with methanolic HCl gave the title compound (200 mg, 29%): mp 150°–155° C.; $^1$H NMR (300 MHz, DMSO-$d_6$) δ 1.52–1.68 (m, 1H), 1.70–1.85 (m, 1H), 2.33–2.58 (m, 1H), 2.62–2.86 (m, 3H), 2.95–3.08 (m, 1H), 3.26 (s, 3H), 3.42–3.55 (m, 3H), 3.57–3.70 (m, 2H), 3.77 (s, 3H), 3.81 (s, 3H), 3.93 (s, 3H), 3.94–4.20 (m, 2H), 4.20–4.40 (m, 4H), 6.73 (d, 1H), 6.84 (d, 1H), 7.04 (s, 1H), 7.17 (t, 1H), 7.42 (s, 1H), 10.52 (s, 1H); MS (DCI/NH$_3$) m/z 510 (M+H)$^+$. Anal. calcd for $C_{28}H_{36}ClN_3O_6 \cdot 1.0$ HCl·1.0 H$_2$O: C, 56.00; H, 6.55; N, 7.00. Found: C, 56.02; H, 6.20; N, 6.94.

EXAMPLE 53
3-[2-((3aR ,9bR)-cis-6-Methoxy-2,3,3a,4,5,9b-hexahydro-[1H]-benz[e]isoindol-1-yl)ethyl]-5,6-methylenedioxyquinazoline-2,4(1H,3H)-dione hydrochloride

EXAMPLE 53A
Methyl 2-Amino-5,6-methylenedioxy benzoate (Trimethylsilyl)diazomethane (6 mL of a 2M solution in hexane) was added to a solution of 5-N-(tert-butoxycarbonyl)amino-1,3-benzodioxole4-carboxilic acid (1.56 g, 9.1 mmol), prepared as described (*J. Org. Chem.*, 4549 (1989)). After stirring for 1 h, the reaction was concentrated and chromatographed (10:1 hexane:EtOAc). The resulting methyl ester was dissolved in CH$_2$Cl$_2$ and treated with TFA and stirred for 30 min. The reaction was concentrated and partitioned between CH$_2$Cl$_2$ and NaHCO$_3$ solution. The organic layer was dried (MgSO$_4$), filtered, concentrated, and chromatographed on SiO$_2$ (5:1 hex: EtOAc) to yield the title compound (700 mg,55%): $^1$H NMR (300 MHz, CDCl$_3$) δ 3.91 (s, 3H), 5.37 (bs, 2H), 5.97 (s, 2H), 6.12 (d, 1H), 6.80 (d, 1H); MS (DCI/NH$_3$) m/z 196 (M+H)$^+$.

EXAMPLE 53B
3-[2-((3aR ,9bR)-cis-6-Methoxy-2,3,3a,4,5,9b-hexahydro-[1H]-benz[e]isoindol-1-yl)ethyl]-5,6-methylenedioxyquinazoline-2,4(1H,3H)-dione hydrochloride Methyl 2-Amino-5,6-methylenedioxy benzoate (375 mg, 1.92 mmol) and triethylamine (0.70 mL, 5.0 mmol) were taken up in anhydrous CH$_2$Cl$_2$ under N$_2$ and cooled to −78° C. Phosgene (1.2 mL of 1.93M sin in toluene) was added and the reaction was stirred at −78° C. for 30 min and at 25° C. for 1.5 h. The product from Example 13J (in 10 mL CH$_2$Cl$_2$) was added and the reaction was stirred 18 h at 25° C. The reaction was partitioned between CH$_2$Cl$_2$ and saturated aqueous NaHCO$_3$. The organic layer was dried (MgSO$_4$), filtered, and concentrated. The residue was dissolved THF (100 mL) and KOt-Bu (5 mL of 1M sin in THF) was added. After stirring for 1 h at 25° C. the reaction was concentrated and partitioned between CH$_2$Cl$_2$ and saturated aqueous NaHCO$_3$. The organic layer was dried (MgSO$_4$), filtered, concentrated and chromatographed on SiO$_2$ (1% EtOH in CH$_2$Cl$_2$ saturated with NH$_3$) to provide the free base of the title compound (900 mg,85%) which was converted to the HCl salt: mp 204°–208° C.; $^1$H NMR (300 MHz, CDCl$_3$ (free base)) δ 1.48–1.62 (m, 1H), 1.73–1.86 (m, 1H), 2.23–2.36 (m, 2H), 2.51–2.71 (m, 3H), 2.87–2.98 (m, 1H), 3.10–3.22 (m, 1H), 3.51 (q, 1H), 3.74–3.85 (m, 2H), 3.81 (s, 3H), 4.11–4.36 (m, 2H), 6.10 (s, 2H), 6.19 (d, 1H 6.68 (d, 1H), 6.79 (d, 1H), 6.93 (d, 1H), 7.10 (t, 1H), 11.34 (bs, 1H); MS (DCI/NH$_3$) m/z 436 (M+H)$^+$. Anal. calcd for $C_{24}H_{26}ClN_3O_5$: C, 61.08; H, 5.55; N, 8.90. Found: C, 60.33; H, 5.73; N, 8.61.

EXAMPLE 54
3-[2-((3aR ,9bR)-cis-6-Methoxy-2,3,3a,4,5,9b-hexahydro-[1H]-benz[e]isoindol-1-yl)ethyl]-7,8-methylenedioxyquinazoline-2,4(1H,3H)-dione hydrochloride

EXAMPLE 54A
Methyl 2-Amino-3,4-methylenedioxy benzoate

To a stirred mixture of 4ramino-1,3-benzodioxole (1.3 lg, 9.6 mnmol), prepared as described in *J. Chem. Soc., Perkin Trans. 1*, 259 (1991), hydroxylamine sulfate (8.2 g, 50 mmol), conc HCl (I mL), and H$_2$O (10 mL) was added a slurry of chloral hydrate (1.8 g, 10.9 mmol), sodium sulfate (9.1 g, 64 mmol), in H$_2$O (30 mL). After stirring at 60° C. for 1.5 h the reaction was kept at 25° C. over night. The brown solid was collected by filtration and washed with water. After drying under vacuum, the solid taken up in methanesulfonic acid (30 mL) and the solution was heated at 45° C. for 30 min. The reaction was cooled to 0° C. and was poured onto 250 g of ice. A dark red solid was collected by filtration. The solid was taken up in a solution of NaOH (2 g solid) in water (14 mL). Hydrogen peroxide solution (30%, 8 mL) was added over 30 min. The reaction was neutralized to pH 7 by the addition 1M HCl. The 4-amino-1,3-benzodioxole-5-carboxylic acid was collected by filtration. (Trimethylsilyl)diazomethane (20 mL of a 2M solution in hexane) was added to a solution of the acid in CH$_2$Cl$_2$ (25 mL) and methanol (2 mL). After stirring for 1 h, the reaction was concentrated and chromatographed on SiO$_2$ (hexane:EtOAc) to provide the title compound (475 mg,25%): $^1$H NMR (300 MHz, CDCl$_3$) δ 3.85 (s, 3H), 5.51 (bs, 2H), 6.01 (s, 2H), 6.28 (d, 1H), 7.53 (d, 1H); MS (DCI/NH$_3$) m/z 196 (M+H)$^+$.

EXAMPLE 54B
3-[2-((3aR ,9bR)-cis-6-Methoxy-2,3,3a,4,5,9b-hexahydro-[1H]-benz[e]isoindol-1-yl)ethyl]-7,8-methylenedioxyquinazoline-2,4(1H,3H]-dione hydrochloride Following the procedure described in Example 53B, the product from Example 54A (475 mg, 2.44 mmol), Et$_3$N (0.74 mL, 5.3 mmol), phosgene (1.3 mL of 1.93M solution in toluene), and the product from Example 13J (.50 g, 2.0 mmol) provided the free base of the title compound (0.77 g, 87%) which was converted to the HCl salt: mp 248°–251° C.; $^1$H NMR (300 MHz, CDCl$_3$(free base)) δ 1.45–1.58 (m, 1H), 1.72–1.83 (m, 1H), 2.17–2.27 (m, 2H), 2.47–2.76 (m, 1H), 2.80–2.90 (m, 1H), 3.03–3.14 (m, 1H), 3.42–3.54 (m, 1H), 3.68–3.82 (m, 2H), 3.80 (s, 3H), 4.15–4.35 (m, 2H), 6.08 (dd, 2H), 6.48 (d, 1H), 6.66 (d, 1H), 6.75 (d, 1H), 7.08 (t, 1H), 7.52 (d, 1H); MS (DCI/NH$_3$) m/z 436 (M+H)$^+$; Anal. calcd for $C_{24}H_{26}ClN_3O_5$: C, 61.08; H, 5.55; N, 8.90. Found: C, 60.80; H, 5.70; N, 8.68.

EXAMPLE 55
3-[2-((3aR ,9bR)-cis-6-Methoxy-2,3,3a,4,5,9b-hexahydro-[1H]-benz[e]isoindol-1-yl)ethyl]-6,7-methylenedioxyquinazoline-2,4(1H,3H)-dione hydrochloride 2-Hydroxy-4,5-methylenedioxy benzoic acid (0.67 g, 3.6 mmol), prepared as described in Synthesis 763 (1988), was stirred at 70° C. with 2 mL of thionyl chloride in 25 mL toluene for 30 min. After evaporation of the solvent, the residue was azeotroped with toluene. The resulting acid chloride was taken up in $CH_2Cl_2$ (20 mL) and added slowly to a solution of the product from Example 13J (.75 g, 3.1 mmol) and $Et_3N$ (0.64 mL, 4.6 mmol) in $CH_2Cl_2$. After stirring for 3 h at 25° C. the reaction was partitioned between $CH_2Cl_2$ and saturated aqueous $NaHCO_3$. The layers are seperated and aqueous. layer was extracted with $CH_2Cl_2$. The combined organics were dried ($MgSO_4$), filtered, concentrated, and chromatographed on $SiO_2$ (38:1:1 EtOAc:HCOOH:$H_2O$). 1.0 g (66%) of the intermediate amide as a free base was obtained after a $NaHCO_3$/$CH_2Cl_2$ workup. The amide (850 mg, 2.1 mmol) was taken up in $CH_2Cl_2$ (20 mL) and 1, 1-carbonyldiimidazole (0.36 g, 2.2 mmol) was added. After stirring for 2 h, the reaction was concentrated and chromatographed (18:1:1 EtOAc:HCOOH:$H_2O$). After a $NaHCO_3$/$CH_2Cl_2$ workup, the free base of the title compound (650 mg,72%) was obtained and converted to the HCl salt: mp 253°–255° C.; $^1$H NMR (300 MHz, $CDCl_3$(free base)) δ 1.45–1.58 (m, 1H), 1.68–1.79 (m, 1H), 2.20–2.31 (m, 2H), 2.46–2.59 (m, 2H), 2.63–2.86 (m, 3H), 3.29–3.44 (m, 3H), 3.81 (s, 3H), 4.15 (t, 2H), 6.11 (s, 2H), 6.67 (d, 1H), 6.69 (s, 1H), 6.75 (d, 1H), 7.10 (t, 1H), 7.36 (s, 1H); MS (DCI/$NH_3$) m/z 437 $(M+H)^+$; Anal. calcd for $C_{24}H_{25}ClN_2O_6$: C, 60.95; H, 5.33; N, 5.92. Found: C, 60.79; H, 5.14; N, 5.80.

EXAMPLE 56

3-[2-((3aR ,9bR)-cis-6-Methoxy-2,3,3a,4,5,9b-hexahydro-|1H|-benz[e]isoindol-1-yl)ethyl]-6,7-dimethoxyquinazoline-4(3H)-one dihydrochloride Ethyl 2-(N,N'-dimethyl-N'-formamidinyl)4,5-dimethoxy benzoate was prepared from the known ethyl 2-amino-4,5-dimethoxy benzoate by the method of Gupton, J. T., Miller, J. F., Bryant, R. D., Maloney, P. R., Foster, B. S. Tetrahedron, 1987, 43(8), 1747. Ethyl 2-(N,N'-dimethyl-N'-formamidinyl)-4,5-dimethoxy benzoate (2.5 g, 8.9 mmol) and the compound resulting from Example 13J (0.57 g, 2.3 mmol) were combined as in Example 43 to yield the title compound (0.67 g, 57%o) as a solid: mp 181°–185° C. (EtOH/$CH_2Cl_2$,$Et_2O$); $[\alpha]_D$ –22.3° (c 0.55 in MeOH); $^1$H NMR (300 MHz, $D_2$) δ 8.26 (s, 1H), 7.50 (s, 1H), 7.25 (t, J=7.9 Hz, 1H), 7.14 (s, 1H), 6.95–6.93 (d, 1H), 6.90–6.87 (d, 1H), 4.81–4.70 (m, 3H), 4.45 (t, J=9 OHz, 2H), 3.99 (s, 3H), 3.96 (s, 3H), 3.84 (s, 3H), 3.72–3.68 (m, 3H), 2.90–2.75 (m, 3H), 2.63–2.54 (m, 1H), 1.97–1.85 (m, 1H), 1.67–1.60 (m, 1H); MS (DCI/$NH_3$) m/z 436 $(M+H)^+$. Anal. calcd for $C_{25}H_{31}Cl_2N_3O_4$·0.6 $H_2O$: C, 57.83; H, 6.25; N, 8.09. Found: C, 57.85; H, 6.25; N, 7.93.

EXAMPLE 57

3-[2-((3aR ,9bR)-cis-6-Methoxy-2,3,3a,4,5,9b-hexahydro-|1H|-benz[e]isoindol-1-yl)ethyl]-7,8-dimeth lguinazoline-4(3H)-one dihydrochloride Methyl 2-(N, N'-dimethyl-N'-fonnamidinyl)-3,4dimethyl benzoate was prepared from the known 2-amino-3,4-dimethyl benzoic acid (Rewcastle, G. W.; Atwell, G. J.; Zhuang, L.; Baguley, B. C.; Denny, W. A. *J. Med. Chem.* 1991,34(1), 217) by the method of Gupton, J. T., Miller, J. F., Bryant, R. D., Maloney, P. R., Foster, B. S. Tetrahedron 1987, 43(8), 1747. Methyl 2-(N,N'-dimethyl-N'-formamidinyl)-3,4-dimethyl benzoate (0.5 g, 2.4 mmol) and the compound resulting from Example 13J (0.4 g, 2.0 mmol) were combined as in Example 43 to yield the title compound (0.53 g, 56%) as a solid: mp 195°–200° C. (EtOH/$Et_2O$); $[\alpha]_D$+22.6° (c 0.46 in MeOH); $^1$H NMR (300 MHz, MeOD) δ 8.89 (s, 1H), 8.11–8.08 (d, 1H), 7.54–7.51 (d, 1H), 7.17 (t, J=6.0 Hz, 1H), 6.84–6.79 (m, 2H), 4.53 (t, J=6.0 Hz, 2H), 4.31–4.17 (m, 1H), 3.81 (s, 3H), 3.89–3.59 (m, 6H), 3.19–3.08 (m, 1H), 2.89–2.78 (m, 2H), 2.56 (s, 3H), 2.51 (s, 3H), 1.98–1.90 (m, 1H), 1.72–1.66 (m, 1H); MS (DCI/$NH_3$) m/z 404 $(M+H)^+$. Anal. calcd for $C_{25}H_{31}Cl_2N_3O_2$·0.3 $H_2O$·0.4 HCl: C, 60.48; H, 6.49; N, 8.46. Found: C, 60.54; H, 6.52; N, 8.32.

EXAMPLE 58

3-[2-((3aR ,9bR)-cis-6-Methoxy-2,3,3a,4,5,9b-hexahydro-|1H|-benz[e]isoindol-1-yl)ethyl]-7,8-dimethoxyquinazoline-4(3H)-one dihydrochloride Ethyl 2-(N,N'-dimethyl-N'-formamidinyl)-3,4-dimethoxy benzoate was prepared from the known ethyl 2-amino-3, 4dimethoxy benzoate (Hey, D. H.; Lobo, L. C. *J. Chem. Soc.* 1954, 2246) by the method of Gupton, J. T., Miller, J. F., Bryant, R. D., Maloney, P. R., Foster, B. S. Tetrahedron, 1987, 43(8), 1747. Ethyl 2-(N,N'-dimethyl-N'-formamidinyl)-3,4dimethoxy benzoate (0.76 g, 2.7 mmol) and the compound resulting from Example 13J (0.56 g, 2.3 mmol) were combined as in Example 43 to yield the title compound (0.13 g, 11%) as a solid: mp 196°–199° C.; $[\alpha]_D$+27.2° (c 0.37 in MeOH); $^1$H NMR (300 MHz, $D_{2O}$) δ 8.30 (s, 1H), 8.01–7.97 (d, 1H), 7.43–7.40 (d, 1H), 7.25 (t, J=6.0 Hz, 1H), 6.94–6.92 (d, 1H), 6.89–6.87 (d, 1H), 4.44 (t, J=6.0 Hz, 2H), 4.27–4.15 (m, 2H), 4.03 (s, 3H), 3.91 (s, 3H), 3.84 (s, 3H), 3.78–3.59, (m, 4H), 3.10–3.20 (m, 1H), 2.90–2.70 (m, 2H), 2.61–2.57 (m, 1H), 1.96–1.90 (m, 1H), 1.65–1.60 (m, 1H); MS (DCI/$NH_3$) m/z 436 $(M+H)^+$. Anal. calcd for $C_{25}H_{31}Cl_2N_3O_4$·0.6 $H_2O$: C, 57.83; H, 6.25; N, 8.09. Found: C, 57.85; H, 6.33; N, 8.05.

EXAMPLE 59

3-[2-((3aR ,9bR)-cis-6-Methoxy-2,3,3a,4,5,9b-hexahydro-|1H|-benz[e]isoindol-1-yl)ethyl]-6-carbomethoxythieno[2,3-d]pyrimidine-2,4(1H,3H)-dione hydrochloride The free base of the compound resulting from Example 13H (240mg, 0.605 mmol) in THF (5mL) under $N_2$ at –78° C. was treated with LDA (2.1 equiv). The reaction was warmed to –5° C. for 45 min, then treated with methyl chloroformate (50 μL, 1.05 equiv.) followed by stirring for 1 h. The reaction was evaporated to dryness and flash chromatographed to give the free base of the title compound (120 mg, 44%) which was converted to the HCl salt and recrystallized from EtOH/$Et_2O$ to give the title compound (65 mg, 22%) as a light yellow solid: $^1$H NMR (300 MHz, $CD_3OD$) δ 1.65 (m, 1H), 1.92 (m, 1H), 2.60 (m, 1H), 2.83 (m, 2H), 3.3–3.4 (m, 3H), 3.55 (t, 2H), 3.66 (m, 1H), 3.81 (s, 3H), 3.90 (s, 3H), 4.10 (br m, 1H), 4.37 (t, 2H), 6.79 (d, 1H), 6.82 (d, 1H), 7.18 (t, 1H), 7.92 (s, 1H); MS (DCI/$NH_3$) m/z456; Anal. calcd for $C_{23}H_{26}ClN_3O_5S$: C, 56.15; H, 5.33; N, 8.54. Found: C, 55.99; H, 5.12; N, 8.33.

EXAMPLE 60

3-[2-((3aR,9bR)-cis-6-Methoxy-2,3,3a, 4,5,9b-hexahydro-[1H]-benz[e]isoindol-1-yl)ethyl]-6-carbomethoxythieno[3,2-d]pyrimidine-2,4(1H,3H)-dione hydrochloride The R,R enantiomer of the compound described in Example 5 (397 mg, 1.00 mmol), prepared from the product from Example 13J as described in Example 5, in THF (5 mL) at –5° C. under $N_2$ was treated slowly with LDA (2.1 equiv). After 60 min methyl chloroformate (80 μL, 1 equiv.) was added and the reaction was stirred for an additional 1 h at 0° C. The reaction was then quenched in saturated sodium bicarbonate and extracted with methylene chloride (3x). The organics were dried with sodium sulfate, filtered, solvent evaporated and flash chromatographed to give the free base of the title compound (110 mg, 24%) which was converted to the HCl salt.: $^1$H NMR (300 MHz, CD$_3$OD) δ 1.65 (m, 1H), 1.94 (m, 1H), 2.60 (ddd, 1H), 2.82 (m, 2H), 3.3–3.4 (m, 3H), 3.58 (t, 2H), 3.67 (m, 1H), 3.81 (s, 3H), 3.95 (s, 3H), 4.10 (br m, 1H), 4.38 (t, 2H), 6.79 (d, 1H), 6.82 (d, 1H), 7.18 (t, 1H), 7.55 (s, 1H); MS (DCI/NH$_3$) m/z 456; Anal. calcd for C$_{23}$H$_{26}$ClN$_3$O$_5$S: C, 56.15; H, 5.33; N, 8.54. Found: C, 55.98; H, 5.16; N, 8.29.

EXAMPLE 61

3-[2-((3aR,9bR)-cis-6-Methoxy-2,3,3a,4,5,9b-hexahydro-|1H|-benz|e|isoindol-1-yl)ethyl|-5-carboethoxy-1H-pyrrolo |2,3-d|pyrimidine-2,4(1H,3H)-dione hydrochloride The urea ester intermediate from Example 30 was dissolved in ethanol (10 mL), treated with a 1.0M solution of potassium tert-butoxide in THF (1.26 mL) and heated to 60° C. for 4 h then stirred overnight at room temperature. The reaction was concentrated, poured into saturated sodium bicarbonate and extracted with methylene chloride. The organic phases were combined, washed with water, then solvent evaporated to provide the free base of the title compound (220 mg, 81%) as a white solid which was converted to HCl salt with 1.0M HCl in Et$_2$O and crystallized from ethyl acetate/ethanol: $^1$H NMR (300 MHz, CD$_3$OD) δ 1.35 (t, 3H), 1.68 (m, 1H), 1.95 (m, 1H), 2.60 (ddd, 1H), 2.85 (m, 2H), 3.3–3.4 (m, 3H), 3.62 (t, 2H), 3.72 (m, 1H), 3.82 (s, 3H), 4.20 (br m, 1H), 4.27 (q, 2H), 4.34 (t, 2H), 6.79 (d, 1H), 6.81 (d, 1H), 7.18 (t, 1H), 7.32 (s, 1H); MS (DCI/NH$_3$) m/e 453. Anal. calcd for C$_{24}$H$_{29}$ClN$_4$O$_5$·0.5NaCl: C, 55.63; H, 5.64; N, 10.52. Found: C, 55.36; H, 5.68; N, 10.68.

EXAMPLE 62

3-[2-((3aR,9bR)-cis-6-Methoxy-2,3,3a,4,5,9b-hexahydro-[1H]-benz[e]isoindol-1-yl)ethyl]-6-methoxy-7-phenylthieno [3,2-d]pyrimidine-2,4(1H,3H)-dione hydrochloride 4-Amino-5-carboethoxy-2-methoxy-3-phenylthiophene (554 mg, 2.0 mmol), prepared as described for 4-amino-5-carboethoxy-2-methoxythiophene in Example 41A, was converted in-situ to the corresponding isocyanate, reacted with the product from Example 13J and cyclized to provide the free base of the title compound (460 mg, 46%) which was converted to the HCl salt and crystallized to give the title compound (220 mg, 20%): $^1$H NMR (300 MHz, DMSO-d$_6$) δ 1.45 (m, 1H), 1.63 (m, 1H), 2.08–2.24 (m, 2H), 2.44 (m, 1H), 2.55 (m, 3H), 3.15–3.30 (m, 4H), 3.75 (s, 3H), 3.96 (t, 2H), 3.99 (s, 3H), 6.72 (d, 1H), 6.73 (d, 1H), 7.08 (t, 2H), 7.3–7.5 (m, 5H), 11.22 (br s, 1H); MS (DCI/NH$_3$) m/z 504. Anal. calcd for C$_{28}$H$_{30}$ClN$_3$O$_4$S: C, 62.27; H, 5.60; N, 7.78. Found: C, 62.01; H, 5.48; N, 7.61.

EXAMPLE 63

3-[2-((3aR,9bR)-cis-6-Methoxy-2,3,3a,4,5,9b-hexahydro-[1H]-benz[e]isoindol-1-yl)ethyl]6-methoxy-7-ethylthieno [3,2-d]pyrimidine-2,4(1H,3H)-dione hydrochloride 4-Amino-5-carboethoxy-3-ethyl-2-methoxythiophene (472 mg, 2.06 mmol), prepared as described for 4amino-5-carboethoxy-2-methoxythiophene in Example 41A, was converted in-situ to the isocyanate, reacted with the product from Example 13J and cyclized to provide the free base of the title compound (240 mg, 26%) which was converted to the HCl salt and crystallized to give the title compound (195 mg, 19%): m.p. 208°; $^1$H NMR (300 MHz, DMSO-d$_6$) δ 1.00 (t, 3H), 1.42 (m, 1H), 1.62 (m, 1H), 2.09–2.25 (m, 2H), 2.42 (m, 1H), 2.55 (m, 5H), 3.18 (t, 1H), 3.25 (m, 3H), 3.75 (s, 3H), 3.95 (t, 2H), 3.99 (s, 3H), 6.72 (d, 1H), 6.74 (d, 1H), 7.07 (t, 1H), 11.59 (br s, 1H); MS (DCI/NH$_3$) m/z 456. Anal. calcd for C$_{24}$H$_{30}$ClN$_3$O$_4$S: C, 58.59; H, 6.15; N, 8.54. Found: C, 58.40; H, 6.03; N, 8.41.

EXAMPLE 64

3-|2-((3aR,9bR)-cis-6-Methoxy-2,3,3a,4,5,9b-hexahydro-|1H|-benz|e|isoindol-1-yl)ethyl|-6-methoxy-7-methylthieno |3,2-d|primidine-2,4(1H,3H)-dione hydrochloride 4Amino-5-arboethoxy-2-methoxy-3-methylthiophene (415 mg, 1.93 mmol), prepared as described for 4amino-5-carboethoxy-2-methoxythiophene in Example 41A, was converted in situ to the isocyanate, reacted with the product from Example 13J and cyclized to give the free base of the title compound (420 mg, 49%) which was treated with 1.0M HCl/Et$_2$O (1.5 mL) and crystallized to give the title compound (365 mg, 40%) as the HCl salt.: mp 205° C.; $^1$H NMR (300 MHz, DMSO-d$_6$) δ 1.45 (m, 1H), 1.63 (m, 1H), 1.99 (s, 3H), 2.20 (m, 2H), 2.45 (m, 1H), 2.55–2.65 (m, 3H), 3.20 (m, 1H), 3.27 (m, 3H), 3.75 (s, 3H), 3.96 (t, 2H), 3.99 (s, 3.0H), 6.72 (d, 1H), 6.74 (d, 1H), 7.08 (t, 1H), 11.60 (br s, 1H); MS (DCI/NH$_3$) m/z 442. Anal. calcd for C$_{23}$H$_{28}$ClN$_3$O$_4$S·0.25 H$_2$O: C, 57.25; H, 5.95; N, 8.71. Found: C, 57.23; H, 5.98; N, 8.59.

EXAMPLE 65

3 -[2-((3aR,9bR)-cis-6-Methoxy-2,3,3a,4,5,9b-hexahydro-|1H]-benz[e]isoindol-1-yl)ethyl|-6-methoxy-7-isopropylthieno [3,2-d]pyrimidine-2,4(1H,3H)-dione hydrochloride 4-Amino-5-carboethoxy-3-isopropyl-2-methoxythiophene (330 mg, 1.36 mmol), prepared in the same fashion as 4-amino-5-carboethoxy-2-methoxythiophene in Example 41A, was converted in-situ to the isocyanate, reacted with the product from Example 13J and cyclized to give 220 mg (34%) of the free base. This was treated with 1.0M HCl/Et$_2$O (1 mL) and crystallized to give the title compound (100 mg, 15%): $^1$H NMR (300 MHz, CDCl$_3$) δ 1.30 (d, 6H), 1.52 (m, 1H), 1.72 (m, 1H), 2.25 (m, 2H), 2.55 (m, 2H), 2.70 (m, 2H), 2.80 (m, 1H), 3.02 (sept, 1H), 3.40 (m, 3H), 3.80 (s, 3H), 4.00 (s, 3H), 4.06 (t, 2H), 6.67 (d, 1H), 6.75 (d, 1H), 7.09 (t, 1H), 9.32 (br s, 1H); MS (DCI/NH$_3$) m/z470. Anal. calcd for C$_{25}$H$_{32}$ClN$_3$O$_4$S: C, 59.34; H, 6.37; N, 8.30. Found: C, 59.06; H, 6.39; N, 8.15.

EXAMPLE 66

3-[2-((3aR,9bR)-cis-6-Methoxy-2,3,3a,4,5,9b-hexahydro-[1H]-benz[e]isoindol-1-yl)ethyl]-7,8-dimethylpyrido |3,2-d]pyrimidine-2,4(1H,3H)-dione dihydrochloride

EXAMPLE 66A 5,6-dicarboximido-3,4dimethyl-1-dimethylamino-1,4,5,6-tetrahydropyridine.

2-Methylbut-2-enal-dimethylhydrazone (1.67 g, 13.3 mmol) (A. Waldner *Helv Chim Acta* 1989, 72, 1435) was reacted with maleimide (860 mg, 87 mmol) in acetonitrile (10 mL) at 60° C. for 4 h, cooled , the precipitate collected, washed with diethyl ether and dried to provide the title compound (1.67 g, 85%).

EXAMPLE 66B 2,3-Dicarboximido-4,5-dimethylpyridine

The product from Example 66A (11.5 g, 51.8 mmol) was dissolved in toluene (200 mL), treated with 70–230 mesh silica gel (23 g) and heated to 100° C. for 20 min. The reaction was cooled, filtered, washed with ethanol (250 mL) and solvents evaporated to give 8.34 g of a red solid. This material was heated to 50° C. in acetic acid (80 mL) while air was bubbled through the solution for 6 h. The reaction was then cooled, the excess acetic acid evaporated, the residue treated with aqueous sodium bicarbonate and extracted with methylene chloride (4×) and ethyl acetate (2×). The organics were dried with sodium sulfate, filtered, and solvent evaporated to give 6.45 g of crude product. This was dissolved in hot ethyl acetate and the title compound that separated upon cooling (1.5 g) was collected. The mother liquor was flash chromatographed to yield another 2.69 g of title compound for a total of 4.19 g (51%).

EXAMPLE 66C

Methyl 4,5dimethyl-3-aminopyridine-2- carboxylate

To the product from Example 66B (2.00 g, 11.4 mmol) in 10% NaOH (34 mL) was added slowly a solution of NaOBr prepared from bromine (650 µL, 1.1 equiv.) and ice cold 15% NaOH. The reaction was stirred 1 h at room temperature then 1 h at 85° C., cooled to 0° C. and carefully neutralized with concentrated HCl. At pH 7 the carboxylic adid of the title compound precipitated, was collected, washed with water and dried to give 490 mg (26%). The acid was heated in methanol (5 mL) with sulfuric acid (2.3 mL) at 70° C. for 3 h, cooled, poured over ice, neutralized with sodium bicarbonate and extracted with methylene chloride (4×). The organics were dried with sodium sulfate, filtered, solvent evaporated and flash chromatographed to give the title compound (320 mg, 60%).

EXAMPLE 66D

3-|2-((3aR,9bR)-cis-6-Methoxy-2,3,3a,4,5,9b-hexahydro-|1H|-benz[e]isoindol-1-yl)ethyl]-7,8-dimethlypyrido [3,2-d|primidine-2,4(1H,3H)-dione dihydrochloride The product from Example 66C (380 mg, 2.11 mmol) was converted in-situ to the isocyanate as in Example 1C, reacted with the product from Example 13J and cyclized to give 675 mg (76%) of the free base of the title compound. This was slurried in methanol, treated with 1.0M HCl/Et$_2$O (6 mL) and crystallized to give the title compound (520 mg, 49%): mp 223°–226° C.; $^1$H NMR (300 MHz, CDCl$_3$) δ 1.52 (m, 1H), 1.73 (m, 1H), 2.27 (m, 2H), 2.35 (s, 3H), 2.40 (s, 3H), 2.55 (m, 2H), 2.68 (m, 1H), 2.81 (m, 2H), 3.40 (m, 3H), 3.80 (s, 3H), 4.28 (t, 2H), 6.65 (d, 1H), 6.74 (d, 1H), 7.09 (t, 1H), 8.40 (s, 1H); MS (DCI/NH$_3$) m/z 421. Anal. calcd for C$_{24}$H$_{30}$Cl$_2$N$_4$O$_3$·0.75H$_2$O: C, 56.86; H, 6.26; N, 11.05. Found: C, 56.85; H, 6.45; N, 11.08.

EXAMPLE 67

3-|2-((3aR,9bR)-cis-9-Methoxy-2,3,3a,4,5,9b-hexahydro-] 1H]-benz[e]isoindol-1-yl) butyl]-6,7-dimethoxyquinazoline-2,4(1H,3H)-dione hydrochloride

EXAMPLE 67A (3aR,9bR)-9-Methoxy-((S)-α-methylbenzyl)-2,3,3a,4,5,9b-|1H|-hexahydrobenz[e]isoindole cis-8-Methoxy-bis-(1,2-hydroxymethyl)-1,2,3,4-tetrahydronaphthalene-1,2-bis mesylate (12.08 g, 31.9 mmol), prepared using the procedures described in U.S. Pat. No. 5,049,564, which is incorporated herein by reference, was dissolved in (S)-(-)-α-methylbenzylamine (60 mL), and the reaction was heated at 70° C. for 20 hours. Excess amine was removed in vacuo, and the product was partitioned between diethyl ether and 5% aqueous NaOH solution. The organic phase was concentrated and purified by chromatography on silica gel eluting with 20% diethyl ether in hexanes to yield the title compound (3.4 g, 69%) as the first eluting product. $^1$H NMR (300 MHz, CDCl$_3$) δ 1.37 (d, 3H), 1.61 (m, 2H), 1.93 (m, 1H), 2.12 (dd, 1H), 2.48 (m, 1H), 2.61 (m, 2H), 2.87 (dd, 1H), 3.18 (dd, 1H), 3.66 (m, 2H), 3.80 (s, 3H), 6.69 (d, 1H), 6.73 (d, 1H), 7.08 (t, 1H), 7.30 (m, 5H).

EXAMPLE 67B (3aR,9bR)-9-Methoxy-2,3,3a,4,5,9b-[1H]-hexahydrobenz[e]isoindole hydrochloride.

The compound resulting from Example 67A as its HCl salt (2.2 g, 6.4 mmol) was dissolved in methanol (150 mL) and 10% Pd/C (0.44 g) was added. The reaction mixture was hydrogenated at 4 atmospheres of hydrogen for 24 hours, filtered, and the solvent evaporated. The product was recrystallized from ethanol:diethyl ether to yield the title compound (1.4 g, 91%) as a white solid. $^1$H NMR (300 MHz, CD$_3$OD) δ 6 1.60 (m, 1H), 1.88 (m, 1H), 2.53 (m, 1H), 2.80 (m, 2H), 2.88 (dd, 1H), 3.60 (m, 2H), 3.82 (s, 1H), 3.93 (dd, 1H), 6.67 (d, 1 H), 6.80 (d, 1H), 7.15 (t, 1H).

EXAMPLE 67C (3aR,9bR)-9-Methoxy-(2-(4aminobutyl))-2,3,3a,4,5,9b-|1H|-hexahydrobenz[e]isoindole A suspensioin of the free base of the product from Example 67B (1.95 g, 8.1 mmol), 4bromobutyronitrile (0.81 mL, 8.1 mmol), and potassium carbonate (1.66 g, 12.2 mmol) in acetonitrile was stirred for 18 h at 25° C. The reaction was partitioned between cold water and EtOAc. The layers are seperated and the aqueous layer is extracted with EtOAc (2×). The combined EtOAc layers are washed with brine, dried (MgSO4), filtered, concentrated, and chromatographed (2% EtOH in EtOAc) to provide 1.87 g (85%) of the nitrile intermediate. A solution of the nitrile (1.8 g, 6.7 mmol) in THF was added dropwise to a stirred suspension of lithium aluminum hydride (1.52 g, 40 mmol) in THF (40 mL). After 4 h at 25° C., a Fieser workup provided 1.8 g of the title compound: $^1$H NMR (300 MHz, CDCl3) δ 1.40 –1.60 (m, 4H), 1.68 (q, 2H), 1.93 (t, 1H), 2.19 (dd, 1H), 2.40 (t, 2H), 2.50–2.67 (m, 3H), 2.70 (t, 2H), 3.11 (dd, 1H), 3.43 (t, 1H), 3.60 (q, 1H), 3.78 (s, 3H), 6.68 (d, 1H), 6.72 (d, 1H), 7.08 (t, 1H).: MS (DCI/NH$_3$).

EXAMPLE 67D

3-|2-((3aR,9bR)-cis-9-Methoxy-2,3,3a,4,5,9b-hexahydro-[1H]-benz[e]isoindol-1-yl) butyl]-6,7-dimethoxyquinazoline-2,4(1H,3H)-dione hydrochloride 2-Carboethoxy-4,5-dimethoxyphenylisocyanate (0.41 g, 1.92 mmol), prepared by the reacton of 2-carboethoxy4,5-dimethoxyaniline and triphosgene, the product from Example 67° C. (0.44 g, 1.6 mmol), and toluene (10 mL) were refluxed for 18 h. The reaction was concentrated and redissolved in THF and potassium t-butoxide (4 mL of 1M solution in THF) was added. After stirring 18 h at 25° C., the reaction is concentrated and partitioned between NaHCO$_3$ solution and CH$_2$Cl$_2$. The organic layer is dried (MgSO4), filtered, concentrated, and chromatographed on SiO$_2$ (10% EtOH in CH$_2$Cl2) and the free base (0.1 g) was converted to the HCl salt: mp 155°–160° C.; $^1$H NMR (300 MHz, CD$_3$OD) δ 1.64–1.85 (m, 5H), 1.85–1.95 (m, 1H), 2.68–2.83 (m, 3H), 3.21–3.43 (m, 3H), 3.66–3.78 (m, 3H), 3.83 (s, 3H), 3.86 (s, 3H), 3.93 (s, 3H), 4.00–4.13 (m, 3H), 6.68 (s, 1H), 6.77 (d, 1H), 6.82 (d, 1H), 7.17 (t, 1H), 7.23 (s, 1H); MS (DCI/NH$_3$) m/z 480 (M+H)$^+$. Anal. calcd for C$_{27}$H$_{34}$ClN$_3$O$_5$·H$_2$O: C, 60.72; H, 6.79; N, 7.86. Found: C, 60.46; H, 6.67; N, 7.64.

EXAMPLE 68

3-|2-((3aR 9bR)-cis-6-Methoxy-2,3,3a,4,5,9b-hexahydro-[1H]-benz[e]isoindol-1-yl)ethyl]-6,7-dimethylquinazoline-2,4(1H,3H)-dione hydrochloride 3,4-Dimethyl-6-carbethoxyaniline, prepared by the method of G. W. Rewcastle et al., *J. Med. Chem.* 34:217 (1991), was treated with 0.33 equivalent of triphosgene. The resulting isocyanate (0.48 g,2.2mmol) and the compound resulting from the example 13J (0.5 g,2mmol) were treated by the procedure described in Example 1C to yield the title compound (0.22 g, 24%) as a white solid: mp 185°–188° C.;

¹H NMR (300 MHz, CDCl₃) δ 7.6 (s, 1H), 7.1 (t, 1H), 6.76 (d, 1H), 6.68 (s, 1H), 6.65 (d, 2H), 4.25 (t, 2H), 3.81 (s, 3H), 3.62 (m, 2H), 3.48 (m, 1H), 2.7–3.06 (m, 2H), 2.5–2.66 (m, 3H), 2.3 (m, 2H), 2.28 (s, 3H), 2.21 (s, 3H), 1.75 (m, 1H), 1.55 (m, 1H); MS (DCI/NH₃) m/z 420(M+H)⁺. Anal. calcd for C₂₅H₃₀ClN₃O₃·0.75H₂O: C, 63.96; H, 6.76; N, 8.95. Found: C, 64.03; H, 6.56; N, 8.93.

EXAMPLE 69

3-[2-((3aR,9bR)cis-6-Methoxy-2,3,3a,4,5,9b-hexahydro-[1H]-benz[e]isoindol-1-yl)ethyl]-7-carbomethoxyquinazoline-2,4(1H,3H)-dione hydrochloride Dimethyl 2-aminoterephtalate was treated with 0.33 equivalent triphosgene by the procedure described in the Example 1C. The resulting isocyanate(1.41 g,6mmol) and the compound resulting from Example 13J (1.35 g, 5.5mmol) were treated by the procedure described in Example 1C to yield the title compound (1.4 g,57%) as a white solid: mp 228°–230° C.; ¹H NMR (300 MHz, CDCl₃) δ 7.82 (d, 1H), 7.6 (d, 1H), 7.51 (s, 1H), 7.1 (t, 1H), 6.79 (d, 1H), 6.66 (d, 1H), 4.27 (t, 2H), 3.98 (s, 3H), 3.8 (s, 3H), 3.67 (m, 2H), 3.5 (m, 1H), 3.0 (m, J=12.5–2.76, m Hz, 3H), 2.33 (m, 2H), 1.8 (m, 1H), 1.6 (m, 1H); MS (DCI/NH₃) m/z 450(M+H)⁺. Anal. calcd for C₂₅H₂₈ClN₃O₅·0.25H₂O: C, 61.22; H, 5.86; N, 8.57. Found: C, 61.23; H, 5.79; N, 8.52.

EXAMPLE 70

3-[2-((3aR,9bR)cis-6-Methoxy-2,3,3a,4,5,9b-hexahydro-[1H]-benz[e]isoindol-1-yl)ethyl]-7-carboxyquinazoline-2,4(1H,3H)-dione hydrochloride The product from Example 69 (0.5 g,1.1 mmol) was refluxed for 1 hour with 10 mL of 1N LiOH in 10 ml of THF. After acidifying the cooled solution obtain the free base of the title compound which was converted to HCl salt and crystalized from ethanol to yield a white solid ( 0.4 g, 83%): mp >250° C.; ¹H NMR (300 MHz, DMSO-d₆)δ 11.78 (s, 1H), 8.04 (d, 1H), 7.8 (s, 1H), 7.72 (d, 1H), 7.19 (t, 1H), 6.84 (d, 1H), 6.76 (d, 1H), 4.28 (m, 2H), 3.78 (s, 3H), 3.5 (m, 2H), 3.35 (m, 1H), 3.02 (m, 2H), 2.6–2.82 (m, 3H), 2.45 (m, 2H), 1.78 (m, 1H), 1.61 (m, 1H); MS (DCI/NH₃) m/z 436(M+H)⁺. Anal. calcd for C₂₄H₂₆ClN₃O₅·1.5H2O: C, 57.77; H, 5.86; N, 8.42. Found: C, 57.77; H, 5.88; N, 8.33.

EXAMPLE 71

3-[2-((3aR,9bR)cis-6-Methoxy-2,3,3a,4,5,9b-hexahydro-[1H]-benz[e]isoindol-1-yl)ethyyl]-7-carboisopropoxyquinazoline-2,4(1H,3H)-dione hydrochloride The product from Example 70 (0.28 g, 0.64mmol) was refluxed overnight with 30 ml of ethanol and 1ml of H₂SO₄.Solution was evaporated and residue was partitioned in dilute base/CH₂Cl₂. The combined organic extracts were dried over anhydrous MgSO₄ and concentrated to give the free base of the title compound (0.12 g,40%) which was converted to HCl salt and crystallized from ethanol /ether to yield 0.19 g of the title compound as white solid: mp 162°–165° C.; ¹H NMR (300 MHz, CDCl₃) δ 8.2 (d, 1H), 8.13 (d, 1H), 7.72 (d, 1H), 7.67 (s, 1H), 7.11 (t, 1H), 7.78 (d, 1H), 6.69 (d, 1H), 4.4 (q, 2H), 4.31 (m, 2H), 3.9 (m, 2H), 3.82 (s,3H), 3.6–3.8 (m, 1H), 3.0–3.28 (m, 2H), 2.5–2.8 (m, 5H), 1.82 (m, 1H), 1.62 (m, 1H), 1.42 (t, 3H); MS (DCI/NH₃) m/z 464(M+H)⁺. Anal. calcd for C₂₆H₃₀ClN₃O₅·H₂O: C, 60.29; H, 6.23; N, 8.11. Found: C, 59.80; H, 6.11; N, 7.81.

EXAMPLE 72

3-[2-((3aR,9bR)cis-6-Methoxy-2,3,3a,4,5,9b-hexahydro-[1H]-benz[e]isoindol-1-yl)ethyl]-7-carbopropoxyquinazoline-2,4(1H,3H)-dione hydrochloride The compound from Example 70 (0.35 g,8 mmol) was treated with n-propanol and 1 ml of H₂SO₄ as described in Example 71 to yield after chromatography 0. 13 g (33%)of title compound as white solid mp 152°–155° C.; ¹H NMR (300 MHz, CDCl₃)(free base) δ8.08 (d, 1H), 7.72 (d, 2H), 7.62 (s, 1H), 7.12 (t, 1H), 6.79 (d, 1H), 6.7 (d, 1H), 4.3 (m, 4H), 3.9 (m, 2H), 3.81 (s, 3H), 3.6 (m, 1H), 3.18 (m, 3H), 2.5–2.8 (m, 5H), 1.82 (m, 3H), 1.6 (m, 1H), 1.08 (t, 2H); MS (DCI(NH₃)) m/z 478 (M+H)⁺. Anal. calcd for C₂₇H₃₃ClN₃O₅·H₂O: C, 60.95; H, 6.44; N, 7.90. Found: C, 61.08; H, 6.21; N, 7.79.

EXAMPLE 73

3-[2-((3aR,9bR)cis-6-Methoxy-2,3,3a,4,5,9b-hexahydro-[1H]-benz[e]isoindol-1-yl)ethyl]-7-carboisopropoxyquinazoline-2,4(1H,3H)-dione hydrochloride The compound resulting from Example 70 (0.3 g,6.9 mmol) was treated with iso-propanol,saturated with HCl as described in Example 71 to yield after chromatography the title compound (0.11 g,33%) as white solid: mp >250° C.; ¹H NMR (300 MHz, CDCl₃) δ8.16 (d, 1H), 8.13 (s, 1H), 7.79 (d, 1H), 7.53 (s, 1H), 7.12 (t, 1H), 6.76 (d, 1H), 6.71 (d, 1H), 5.23 (m, 1H), 4.38 (m, 2H), 3.9–4.18 (m, 3H), 3.82 (s, 3H), 3.28–3.72 (m, 4H), 2.76 (m, 4H), 2.5–2.66 (m, 1H), 1.88 (m, 1H), 1.62 (m, 1H), 1.4 (s, 3H), 1.38 (s, 3H); MS (DCI/NH₃) m/z 478(M+H)⁺. Analysis calcd for C₂₇H₃₂ClN₃O₅: C, 63.09; H, 6.27; N, 8.17. Found: C, 62.70; H, 6.17; N, 8.03.

EXAMPLE 74

3-[2-((3aR,9bR)cis-6-Methoxy-2,3,3a,4,5,9b-hexahydro-[1H]-benz[e]isoindol-1-yl)ethyl]-7-nitroquinazoline-2,4(1H,3H)-dione hydrochloride 4.74 g (22.57 mmol) of ethyl 6-amino-4-nitro benzoate, prepared from 2-amino-4-nitrobenzoic acid, was treated with 1.3 equivalent of 2-chloroethylisocyanate by the procedures described in Eur. J. Med. Chem., 28: 499 (1993). The resulting urea (1.23 g,3.9 mmol) and the compound from Example 13G (0.66 g,3.25 mmol) were refluxed in 20 mL of acetonitrile in the presence of 0.83 mL of diisopropylethylamine for 48 h. The reaction mixture was evaporated and residue was chromatographed, eluting with ethylacetate:formic acid:water(18: 1: 1) to afford the free base of the title compound (0.4 g, 29%) which was converted to HCl salt and crystallized from ethanol/ether.: mp >250° C.; ¹H NMR (300 MHz, CDCl₃) δ7.95 (d, 1H), 7.72 (m, 2H), 7.09 (t, 1H), 6.68 (d, 1H), 6.65 (d, 1H), 4.3 (m, 2H), 3.8 (s, 3H,), 3.42–3.75 (m, 3H), 3.05 (m, 2H), 2.4–2.8 (m, 5H), 1.82 1H), 1.61 (m, 1H); MS (DCI/NH₃) m/z 437(M+H)⁺. Anal. calcd for C₂₃H₂₅ClN₄O₅·0.5H₂O: C, 57.33; H, 5.44; N, 11.63. Found: C, 57.09; H, 5.11; N, 11.33.

EXAMPLE 75

3-[2-((3aR,9bR)cis-6-Methoxy-2,3,3a,4,5,9b-hexahydro-[1H]-benz[e]isoindolyl-1-yl)ethyl]-7-acetamidoquinazoline-2,4(1H,3H)-dione hydrochloride The compound resulting from Example 74 (0.3 g, 0.68 mmol) was dissolved in methanol (30 mL) and 10% Pd/C (0.3 g) was added. The reaction was hydrogenated at atmospheric pressure at room temperature for 24 h. The catalyst was removed by filtration and the solvent was evaporated to yield 0.18 g of amino compound. The amino compound (0. 15 g, 0.37 mmol) was dissolved in 25 mL of CH₂Cl₂ and 0.045 mL of pyridine, followed by 0.049 mL (0.44 mmol) of acetic anhydride were added to the reaction mixture followed by a catalytic amount of DMAP. The reaction mixture was stirred at room temperature for 24 h, the solvents were evaporated and residue chromatographed on SiO$_2$ to yield the free base of the title compound (0.11 g, 66%) which was converted to HCl salt and crystalized from ethanol: mp 255°–257° C.; $^1$H NMR (300 MHz, CDCl$_3$) δ6 7.88 (d, 2H), 7.08 (t, 1H), 6.85 (d, 1H), 6.75 (d, 1H), 6.69 (d, 1H), 4.25 (m, 2H), 3.8 (s, 3H), 2H), 3.48 (m, 1H), 3.0 (m, 2H), 2.5–2.87 (m, 5H), 2.45 (s, 3H), 1.9 (m, 1.55 (m, 1H); MS (DCI/NH$_3$) m/z 449(M+H)$^+$. Anal. calcd for C$_{25}$H$_{29}$ClN$_4$O$_4$H$_2$O: C, 59.70; H, 6.21; N, 11.14. Found: C, 59.14; H, 5.95; N, 10.97.

EXAMPLE 76

3-[2-((3aR,9bR)cis-6-Methoxy-2,3,3a,4,5,9b-hexahydro-1WH-benz[e]isoindol-1-yl)lethyl]-7-methanesulfamlquinazoline-2,4(1H,3H)-dione hydrochloride 1.16 g (037mmol) of the intermediate urea product obtained by the procedure described for Example 74 was dissolved in 100mL of methanol and hydrogenated for 18 h under 4 atmospheres of pressure in the presence of 0.12 g of Pd/C. Catalyst was removed by filtration and evaporation of solvent yielded the desired amino urea. This compound (1 g, 3.5mmol) was dissolved in 20 mL of CH$_2$C$_{12}$, cooled to 0° C. and 0.5 mL of pyridine, followed by 0.3mL (3.87mmol) of methanesulfonyl chloride was added to the reaction mixture. Reaction mixture was stirred at room temperature overnight, then quenched into water and extracted with CH$_2$Cl$_2$. Combined organic extracts were evaporated and residue was chromatographed using 30% ethyl acetate: hexane as an eluant. This afforded 0.74 g (60%) of desired product. The sulfonamideurea (0.74 g ,2 mmol), obtained as described above and 0.47 g (2 mmol) of the product from Example 13G were treated as described in Example 74 to yield the title compound (0.3 ig, 32%) of as a white solid: mp>250° C.; $^1$H NMR (300 MHz, DMSO-d$_6$)δ6 8.22 (s, 1H), 7.82 (d, 1H), 7.08 (t, 1H), 7.02 (d, 1H), 6.92 (dd, 1H), 6.73 (dd, 2H), 3.98 (t, 2H), 3.75 3H), 3.28 (m, 2H), 3.2 (t, 1H), 3.08 (s, 3H), 2.58 (m, 3H), 2.45 (m, 2H), .2.22(m, 2H), 1.65 (m, 1H), 1.45 (m, 1H); MS (DCI/NH$_3$) m/z485(M+H)$^+$. Anal. calcd for C$_{24}$H$_{29}$ClN$_4$SO$_5$: C, 54.39; H, 5.70; N, 10.57. Found: C, 54.46; H, 5.42; N, 10.64.

EXAMPLE 77

3-[2-((3aR,9bR)cis-6-Methoxy-2,3,3a,4,59b-hexahydro-[1H]-benz[e]isoindol-1-yl)ethyl]-7-methoxy-8-methyl-quinazoline-2(1H,3H)-dione hydrochloride 2-Methyl-3-nitrophenol (10 g,65.3 mmol) was refluxed for 4 h in 300 mL of acetone with 2 equivalents of K$_2$CO$_3$ (18 g) and iodomethane (5mL, 80.31 mmol). The resulting 2-methyl-3-methoxynitrobenzene (9 g, 53.83 mmol) was reduced by hydrogen in the presence of Pd/C (0.9 g) in 250mL of methanol. The resulting 2-methyl-3-methoxyaniline was converted to 2-methyl-3-methoxy-6-carbethoxyaniline as described in *J. Med. Chem.* 34:217 (1991). This was reacted with 0.33 equivalents of triphosgene by the procedure described in Example 1C. The resulting isocyanate (0.43 g,2.2 mmol) and the compound resulting from the Example 13J (0.5 g,2 mmol) were treated by the procedures described in Example IC to yield the title compound (0.5 g,62%) as a white solid: mp 239°–240° C.; $^1$H NMR (300 MHz, CDCl$_3$) δ6 8.34 (s, 1H), 8.01 (d, 1H), 7.1 (t, 1H), 6.78 (t, 1H), 6.68 (d, 1H), 4.21 (t, 2H), 3.93 (s, 3H), 3.81 (s, 3H), 3.43 (m, 3H), 2.61-3H), 2.59 (m, 2H), 2.3 (m, 2H), 1.75 (m, 1H), 1.55 (m, 1H); MS (DCI/NH$_3$) m/z 436(M+H)$^+$. Anal. calcd for C$_{25}$H$_{30}$ClN$_3$O$_4$·0.5H$_2$O: C, 62.43; H, 6.50; N, 8.74. Found: C, 62.11; H, 6.34; N, 8.59.

EXAMPLE 78

3-[2-((3aR,9bR)cis-6-Methoxy-2,3,3a,4,5,9b-hexahydro-[1H]-benz[e]isoindol-1I-yl)ethyl]-7-ethox -8-methyl-quinazoline-2,4(1H,3H!-dione hydrochloride 2-Methyl-3-ethoxy-6-carbomethoxyaniline was prepared following the procedure described for Example 77 by substituting iodomethane for iodoethane. The product was converted to the corresponding isocyanate by treatment with 0.33 equivalents of triphosgene. The resulting isocyanate (0.517 g,2.2 mmol) and the compound resulting from the Example 13J (0.5g,2mmol) were treated by the procedures described in Example 1C to yield the title compound (0.45g,50%) as a white solid: mp 173–175° C.; $^1$H NMR (300 MHz, CDCl$_3$) δ 8.28 (s, 1H), 7.98 (d, 1H), 7.1 (t, 1H), 6.78 (d, 1H), 6.68 (d, 1H), 4.21 (m, 2H), 4.18 (m, 2H), 3.81 (s, 3H), 3.45 (m, 3H), 2.62-2.88 (m, 3H), 2.58 (m, 2H), 2.29 (m, 2H), 2.2 (s, 3H), 1.75 (m, 1H), 1.55 (m, 1H), 1.49 (t, 3H); MS (DCI/NH$_3$) m/z 450(M+H)$^+$. Anal. calcd for C$_{26}$H$_{32}$ClN$_3$O$_4$·0.5H$_2$O: C, 63.09; N, 6.72; N, 8.49. Found: C, 62.93; N, 6.68; N, 8.41.

EXAMPLE 79

3-[2((3aR,9bR)cis-6-Methoxy-2,3, 3a,4,5,9b-hexahydro-[1H]-benz[e]isoindol-1-yl) ethyl]-quinazoline-2,4(1H,3H)-dione hydrochloride 2-Carbethoxy-phenylisocynate, prepared from 2-carbethoxyaniline (0.33 g, 2.0 mmol) and triphosgene (0.21g,0.66 mmol) as in Example 1C and the compound resulting from Example 13J were treated by the procedures described in example 1C to yield 0.28 g of title compound as a white solid: mp 170–172° C.; $^1$H NMR (300 MHz, CDCl$_3$) δ 7.96 (d, 1H), 7.5 (t, 1H), 7.1 (m, 2H), 6.9 (d, 1H), 6.88 (d, 1h), 6.68 (d, 1H), 4.26 (t, 2H), 3.81 (s, 3H), 3.4–3.62 (m, 3H), 2.78–3.0 (m, 2H), 2.49–2.77 (m, 3H), 2.3 (m, 2H), 1.77, 1.55 (m, 1H); MS (DCI(NH3)) m/e 392(M+H)+; Analysis calc'd for C23H25N3O3.HCl.0.25H2O: C, 63.88; H, 6.18; N, 9.72; found: C, 63.61; H, 6.09; N, 9.52.

EXAMPLE 80

3-[2-((3aR,9bR)cis-6-Methoxy-2,3,3a,4,5,9b-hexahydro-[1H-benz[e]isoindol-1- yl)ethyl]-7,8-dimethylquinazoline-2,4(1H,3H)-dione hydrochloride 2,3-Dimethyl-6-carbethoxyaniline, prepared by the method of G. W. Rewcastle et al., *J. Med. Chem.*34:217(1991), was treated with 0.33 equivalent of triphosgene. The resulting isocyanate (0.53g,2.42mmol) and the compound resulting from the example 13J (0.5g,2mmol) were treated by the procedure described in the example 1C to yield the title compound (0.6g, 70%) as a white solid: m.p. 210°–212°; 1H NMR (300 MHz, CDCl3(free base)) d 8.62 (s, 1H), 7.9 (d, 1H), 7.09 (t, 1H), 7.05 (d, 1H), 6.75 (d, 1H), 6.68 (d, 1H), 4.22 (t, 2H), 3.8 (s, 3H), 3.43 (m, 3H), 2.63–2.88 (m, 3H), 2.48–2.6 (m, 2H), 2.39 (s, 3H), 2.28 (m, 2H), 2.26 (s, 3H), 1.73 (m, 1H), 1.52 (m, 1H); MS (DCI(NH3)) m/e 420(M+H)+; Analysis calc'd for C25H29N3O3.HCl.H2O: C, 63.35; H, 6.80; N, 8.86; found: C, 63.18; H, 6.68; N, 8.68.

EXAMPLE 81

3-[2-((3aR,9bR)cis-6-Methoxy-2,3,3a,4, 5,9b-hexahydro-[1H]-benz[e]isoindol-1-yl) ethyl]-7,8-dimethoxyquinazoline-2,4(1H,3H)-dione hydrochloride 2,3-Dimethoxy-6-carbmethoxyaniline, prepared by the method of G. W. Rewcastle et al., *J. Med. Chem.*34:217 (1991), was treated with 0.33 equivalent of triphosgene. The resulting isocyanate (0.56g,2.4mmol) and the compound resulting from Example 13J (0.48g,1.95 mmol) were treated by the procedure described in Example 1C to yield the title compound (0.5g, 55%) as a white solid: m.p. 174°–176°; 1H NMR (300 MHz, CDCl3(free base)) d 8.21 (s, 1H), 7.83 (d, 1H), 7.1 (t, 1H), 6.81 (d, 1H), 6.78 (d, 1H), 6.68 (d, 1H), 4.2 (t, 2H), 3.98 (s, 3H), 3.92 (s, 3H), 3.81 (s, 3H), 3.42 (m, 3H), 2.62–2.88 (m, 3H), 2.55 (m, 2H), 2.28 (m, 2H), 1.78 (m, 1H), 1.52 (m, 1H); MS (DCI(NH3)) m/e 452(M+H)+; Analysis calc'd for C25H29N3O5.HCl.H20: C, 60.42; H, 6.29; N, 8.45; found: C, 60.87; H, 6.22; N, 8.35.

EXAMPLE 82
3-[2-((3aR,9bR)cis-6-Ethoxy-2,3,3a,4,5, 9b-hexahydro-|1H|-benz|e|isoindol-1-yl) ethyl|-6,7-dimethoxyquinazoline-2,4(1H,3H)-dione hydrochloride

EXAMPLE 82A
(3aR,9bR)-6-Hydroxy-2,3,3a,4,5,9b-|1H|-hexahydrobenz|e|isoindole hydrobromide The product resulting from Example 13G (5g,20.9mmol) was dissolved in 150ml of $CH_2Cl_2$ and the resulting solution was cooled to −78° C.21 ml of 1M solution of boron tribromide in methylene chloride was added to the solution and the reaction was warmed to room temperature and stirred for 4 hours. It was cooled again to −78C and treated with methanol. Evaporation and trituration with ethyl acetatate afforded 4.9g (87%) of the title compound as white crystals.

EXAMPLE 82B
(3aR,9bR)-6-Hydroxy-2-carbobenzyloxy-2,3,3a,4,5,9b-[1]-hexahydrobenz|e|isoindole hydrobromide The product obtained from Example 82A (4.9g, 18.21 mmol) was dissolved in 100ml of trifluoroacetic acid. The resulting solution was cooled to 0° C. and acetyl chloride (2.58ml,36.42mmol) was added to the reaction mixture. It was stirred at room temperature for 2.5 hours. The reaction mixture was evaporated and partitioned between $NaHCO_3$ solution and $CH_2Cl_2$. CBZ chloride (3.8 ml, 1.5 equiv.) was added to this biphasic solution and it was vigorously stirred for 2 hours. Then the layers were separated, and the combined organic layers were dried with $MgSO_4$ and evaporated. The residue was dissolved in ethanol and $NH_4OH$ solution was added to it. The reaction was stirred overnight, then solvents were evaporated and the residue obtained was dissolved in ethyl acetate, washed with water, dil. HCl, and brine. Combined organic layers were dried with $MgSO_4$ and evaporated to yield 6.9 g of the title compound as an oil.

EXAMPLE 82C
(3aR,9bR)-6-Ethoxy-2-carbobenzyloxy-2,3,3a,4,5,9b-[[1H]-hexahydrobenz[e]isoindole hydrobromide The product from Example 82B (3.5 g, 10.83 mmol) was dissolved in 300 ml of acetone; 3.0 g of $K_2CO_3$ (2 equiv.) and 1.03 ml (12.87 mmol) iodoethane were added to the solution and it was stirred at reflux for 48 hours. The reaction mixture was evaporated and the residue was partitioned between water and ethylacetate. The organic layer was separated, dried with $MgSO_4$ and evaporated. The residue obtained was chromatographed, eluting with 20% ethyl acetate/hexane to afford 23 g of the title compound.

EXAMPLE 82D
(3aR,9bR)-6-Ethoxy-2,3,3a,4,5,9b-[1H]-hexahydrobenz[e]isoindole hydrochloride The product from Example 82C (2.3 g) was dissolved in 100 ml of methanol, 0.23 g of Pd/C was added to the solution and it was hydrogenated under 4 atm pressure for 18 hours. The catalyst was removed by filtration and the solvent was evaporated to yield the title compound. $^1H$ NMR (300 MHz, $CDCl_3$) δ7.1 (t, 1H), 6.78 (d, 1H), 6.68 (d, 1H), 4.03 (m, 2H), 3.45 (m, 1H), 3.35 (m, 1H), 3.25 (m,1H), 2.82 (m, 3H), 2.5 (m, 2H), 1.8 (m, 1H), 1.55 (m, 1H), 1.42 (t, 3H).

EXAMPLE 82E
3aR,9bR)-2-Aminoethyl-6-ethoxy-2,3,3a,4,5,9b-[1H]-hexahydrobenz|e|isoindole The product from Example 82D (1.4 g, 6.45 mmol) was treated with 0.45 ml (1.1 equiv.) of chloroacetonitrile as outlined in Example 131 to yield 1.3 g of the intermediate nitrile. Reduction with 1.3 g of $LiAlH_4$ as described in Example 13J yielded 1.1 g of title compound.: $^1H$ NMR (300 MHz, $CDCl_3$) δ7.09 (t, 1H), 6.73 (d, 1H), 6.68 (d, 1H), 4.02 (q, 2H), 3.42 (m, 1H), 3.28 (m, 2H), 2.8 (t, 2H), 2.48–2.78 (m, 5H), 2.18 (t, 2H), 1.71 (m, 1H), 1.55 (m, 1H).

EXAMPLE 82F
3-[2-((3aR,9bR)cis-6-Ethoxy-2,3,3a,4,5,9b-hexahydro-|1H|-benz|e|isoindole-1-yl)ethyl|-6,7-dimethoxyquinazoline-2,4(1H,3H)-dione hydrochloride 2-Carbomethoxy-4,5,-dimethoxylaniline was treated with 0.33 equivalent of triphosgene. The resulting isocynate (0.33 g,1.39 mmol) and the compound resulting from Example 82E (0.3 g, 1.15 mmol) were treated by the procedures described in Example 1C to yield 0.28 g(52%) of title compound as a white solid.: m.p. 220°–222°; 1H NMR (300 MHz, CDCl3) d 7.09 (d, 1H), 7.05 (s, 1H), 6.75 (d, 1H), 6.68 (d, 1H), 6.15 (s, 1H), 4.29 (m, 2H), 4.02 (q, 2H), 3.97 (s, 3H), 3.85 (s, 3H), 3.78 (m, 2H), 3.52 (q, 2H), 3.15 (m, 1H), 3 (0m, 1H), 2.55–2.8 (m, 3H), 2.35 (q, 2H), 1.81 (m, 1H), 1.58 (m, 1H), 1.42 (t, 3H); MS (DCI(NH3)) m/e 466 (M+H)+; Analysis calc'd for C26H31N3O5.HCl.H2O: C, 60.05; H, 6.59; N, 8.08; found: C, 59.74; H, 6.4.0; N, 7.93.

EXAMPLE 83
3-[2-((3aR,9bR)cis-6-Ethyl-2,3,3a,4,5,9b-hexahydro-[1H]-benz[e]isoindole-1-yl)ethyl]-6,7-dimethoxyquinazoline-2,4(1H,3H)-dione hydrochloride

EXAMPLE 83A
(3aR,9bR)-6-Hydroxy-2-carbobenzyloxy-2,3,3a,4,5,9b-|1H|-hexahydrobenz[e]isoindole trifluoromethanesulfonate ester To a stirred solution of the product from Example 82B, (0.385 g., 1.2 mMol., 1.0 equiv.) in 12 mL $CH_2Cl_2$ cooled to −78° was added triethylamine, (0.17 mL, 1.2 mMol., 1.0 equiv.) followed by trifluoromethansulfonic anhydride, (0.17 mL, 1.2 mMol., 1.0 equiv.). The reaction solution was left stirring at −78° for 1h when it was warmed to room temperature, diluted with 50 mL $CH_2Cl_2$ and washed with $H_2O$, (15 mL), followed by sat. $NaHCO_3$. The resulting solution was then dried over $MgSO_4$, filtered, and solvents evaporated to furnish the crude product as an oil. Purification of the crude product on silica gel furnished the title compound as a colorless oil, (0.39 g, 70%) $^1H$ NMR (300 MHz, CDCl3), δ(TMS): 1.60, (1H, m); 1.92, (1H, m); 2.50, (1H, m), 2.67, (1H, m); 3.00, (½H, t, J=3.0Hz); 3.05, (½H, t, J=3.0Hz); 3.23, (1H, q, J=9.0Hz); 3.45, (2H, m); 3.73, (1H,dd, J=6.0Hz); 3.98, (1H, m); 5.13, (2H, m); 7.15, 3H, m); 7.34, (5H, m).

EXAMPLE 83B
(3aR,9bR)-6-Acet 1-2-carbobenzyloxy-2,3,3a,4,5,9b-[1H]-hexahydrobenz|e|isoindole To a stirred solution of the product from Example 83A (0.385 g, 0.85 mMol., 1.0 equiv.), in 3 mL of DMF was added triethylamine, (0.355 mL, 0.255 mMol., 3.0 equiv.), butylvinyl ether, (0.821 mL, 5.9 mMol., 7.0 equiv.), 1, 3-bis(diphenylphosphino)propane, (0.05 g, 0.12 mMol., 0.15 equiv.) and palladium(II)acetate, (0.02 g, 0.12 mMol., 0.15 equiv.). The resulting dark reaction solution was heated to 80° C. for 2h when it was cooled to room temperature and quenched with 5% (v/v) HCl, (2mL), and let stir at room temperature for 2h. The reaction was then extracted with $CH_2Cl_2$ (3×30mL), and the rtesulting combined organics washed with H₂O, and brine, dried over MgSO₄, filtered and evaporated and separated (silica gel, 5:1 hexanes/ ethyl acetate), to furnish the title compound as a colorless oil, (0.18 g, 61%). ¹H NMR (300 MHz, CDCl3), δ(TMS): 1.54, (1H, m); 1.86, (1H, m); 2.45, (1H, m), 2.55, (3H, s); 2.90, (1H, m); 3.07, (1H, m); 3.25, (1H, q, J=9.0 Hz); 3.45, (2H, m); 3.73, (1H, dd, J=6.0 Hz); 4.00, (1H, m); 5.13, (2H, m); 7.22, (2H, m); 7.34, (5H, m); 7.52, (1H,m).

EXAMPLE 83C
(3aR,9bR)-6-Ethyl-2,3,3a,4,5,9b-|1H|-hexahydrobenz[e]isoindole hydrochloride The product from Example 83B (0.30 g, .085 mMol., 1.0 equiv.) was dissolved in 25 mL of dry methanol to which was added 1 mL of conc. HCl. To this solution was added dry 10% Pd/C, (0.045 g), the resulting suspension was then put under a hydrogen atmosphere at 4 atmospheres pressure for 17 h at room temperature. The reaction suspension was then filtered and evaporated to give a crude solid which was triturated with methanol / diethyl ether to furnish the title compound, (0.172 g, 78%). ¹H NMR (300 MHz, CDCl3), b(TMS): 1.17, (3H, t, J =7.5 Hz); 1.63, (1H, m); 1.95, (1H, m), 2.63, (4H, m); 2.90, (1H, m); 3.07, (1H, t, J=12 Hz); 3.22, (1H, dd, J=9.0 Hz, J=3 Hz); 3.77, (1H, dd, J=12.0 Hz, J=3.0 Hz); 7.07, (3H, m).

EXAMPLE 83D
(3aR,9bR)-2-Cyanomethyl-6-ethyl-2,3,3a,4,5,9b-|1H|-hexahydrobenz[e]isoindole The product from Example 83C (1.23 g, 5.2 mmol), chloroacetonitrile (0.22 mL, 5.7 mmol), potassium carbonate (2.4 g, 11.4 mmol), acetone (30 mL), and water (10 mL) were stirred at reflux for 6 h. The reaction was partitioned between ethyl acetate and brine. The ethyl acetate layer was dried (MgSO₄), filtered, concentrated and chromatographed (2:1 hex: ethyl acetate) to yield 1.0 g (80%) of the title compound ¹H NMR (300 MHz, CDCl₃) δ 1.20 (t, 3H), 1.61–1.71 (m, 1H), 1.76–1.87 (m, 1H), 2.50–2.79 (m, 7H), 3.20–3.28 (m, 2H), 3.50 (q, 1H), 3.65 (s, 2H), 6.97 (d, 1H), 7.03 (d, 1H), 7.11 (t, 1H); MS (DCI/NH₃) m/e 241 (M+H)⁺.

EXAMPLE 83E
(3aR,9bR)-2-Aminoith 1-6-ethyl-2,3,3a4,5,9b-|1H|-hexahdrobenz[e]isoindole The product from Example 83 D (1.0 g, 4.2 mmol) in 20 mL THF was added dropwise to a suspension of LiAlH₄ (0.93 g, 25 mmol) in THF (80 mL). After stirring for 1 h, the reaction was quenched by the portionwise addition of sodium sulfate decahydrate. After stirring for 30 min, the reaction was diluted with ethyl acetate (100 mL) and the solid was removed by filtration. Concentration of the filtrate yielded 0.97 g (95%) of the title compound: ¹H NMR (300 MHz, CDCl₃) δ 1.19 (t, 3H), 1.47–1.84 (m, 4H), 2.142.22 (m, 2H), 2.45–2.74 (m, 6H), 2.81 (t, 2H), 3.22–3.33 (m, 2H), 3.45 (q, 1H), 4.15–4.27 (m, 1H), 6.95–7.13 (m, 3MS (DCI/NH₃) m/e 245 (M+H)⁺.

EXAMPLE 83F
3-|2-((3aR,9bR)cis-6-Ethyl-2,3,3a4,5,9b-hexahydro-|1H|-benz[e]isoindol-1-yl) ethyl|-6,7-dimethoxyquinazoline-2,4 (1H,3H)-dione hydrochloride Following the procedure described in Example 1C, methyl 2-amino-4,5-dimethoxybenzoate (0.24 g, 1.1 mmol), Et₃N (0.36 mL, 2.6 mmol), phosgene (0.59 mL of 1.93M solution in toluene), and the product from Example 83E (.25 g, 1.0 mmol) provided 0.20 g (44%) of the free base of the title compound which was converted to the HCl salt: mp 200–202° C.; 1H NMR (300 MHz, CDCl₃(free base)) δ 6 1.19 (t, 3H), 1.53–1.69 (m, 1H), 1.78–1.89 (m, 1H), 2.34 (q, 2H), 2.542.80 (m, 5H), 2.95–3.06 (m, 1H), 3.143.26 (m, 1H), 3.57 (m, 1H), 3.78–3.91 (m, 2H), 3.84 (s, 3H), 3.97 (s, 3H), 4.19–4.39 (m, 2H), 6.14 (s, 1H), 6.96–7.13 (m, 3H), 7.00 (s, 1H), 11.30 (bs, 1H); MS (DCI/NH₃) m/z 450 (M+H)⁺. Anal. calcd for C₂₆H₃₂ClN₃O₄·0.25 H₂O: C, 63.67; H, 6.68; N, 8.57. Found: C, 64.26; H, 6.64; N, 8.65.

EXAMPLE 84
3-|2-((3aR,9bR)cis-6-Methoxy-2,3,3a,4,5,9b-hexahydro-|1H|-benz[e]isoindol-1-yl) ethyl|7-(2-methylphenyl)thieno|3,2-d|pyrimidine-2,4(1H,3H)-dione hydrochloride Ethyl 3-amino-4-(2-methylyphenyl)thiophene-2-carboxylate (0.81 g, 3.10 mmol) was dissolved in 30 mL dichlormethane and cooled to −78° C. Triethylamine (0.69 mL, 4.95 mmol) was then added, followed by the dropwise addition of 1.27 mL (2.45 mmol) 1.93M phosgene in toluene solution. The reaction was stirred at −78° C. for 1 h and then allowed to warm to rt, at which time a solution of the product from Example 13J (0.61 g, 2.45 mmol) in 15 mL dichloromethane was added. The reaction was stirred at room temperature for 2 h., quenched in 5% NaHCO₃, extracted with dichloromethane (3x), and the combined extracts washed with brine, dried (Na₂SO₄), filtered, and evaporated. The resulting oil (1.18 g) was taken up in 50 mL of anhydrous tetrahydrofuran and 0.30 g (2.36 mmol) anhydrous potassium t-butoxide added. The reaction was stirred 2 h at room temperature, then quenched in 100 mL of pH 7 buffer solution, extracted with ethyl acetate, dried (Na₂SO₄), and evaporated. The resulting product was treated with ethereal HCl to yield 0.44 g of the title compound as a white solid.: mp 197–200° C.; ¹H NMR (300 MHz, DMSO-d₆) δ 1.6 (m, 2H), 1.8 (m, 2H), 2.65 (m, 3H), 3.0 (m, 2H), 3.35 (s, 3H), 3.45–3.55 (m, 3H), 3.78 (s, 3H), 4.0–4.25 (m, 2H), 6.7–6.87 (m, 2H), 7.1–7.4 (m, 6H), 7.78 (d, 1H), 11.65 (d, 1H); MS (DCI/NH₃) m/e 488 (M+H)t. Anal. calcd for C₂₈H₃₀ClN₃O₃S·0.25H₂O: C, 63.62; H, 5.82; N, 7.95. Found: C, 63.49; H, 5.58; N, 7.59.

EXAMPLE 85
3-[2-((3aR,9bR)cis-6-Methoxy-2,3,3a,4,5,9b-hexahydro-|1H|-benz[e]isoindol-1-yl) ethyl]-7-(2-methoxyphenyl)thieno[3,2-d]pyrimidine-2,4(1H,3H)-dione hydrochloride Ethyl 3-amino-2-4-(2-methxoyphenyl)thiophene-2-carboxylate (0.86 g, 3.10 mmol) was dissolved in 30 mL dichlormethane and cooled to −78° C. 0.69 ml (4.95 mmol) of triethylamine was then added, followed by the dropwise addition of 1.27 mL (2.45 mmol) 1.93M phosgene in toluene solution. The reaction was stirred at −78° C. for 1h and then allowed to warm to room temperature, at which time a solution of the the product from Example 13J (0.61 g, 2.45 mmol) in 15 mL dichloromethane was added. The reaction was stirred at rt for 2 h and then quenched in 5% NaHCO₃, extracted with CH₂Cl₂, dried (Na₂SO₄), filtered, and evaporated. The resulting solid (1.08 g) was taken up in 50 mL of anhydrous tetrahydrofuran and 0.26 g (2.36 mmol) anhydrous potassium t-butoxide added. The reaction was stirred 2 h at room temperature, then quenched in 100 mL of pH 7 buffer solution. The reaction was extracted with ethyl acetate, dried (Na₂SO₄), and evaporated. The resulting product was treated with ethereal HCl to yield 0.64 g of the title compound as a white solid: mp 228–230° C.; ¹H NMR (300 MHz, DMSO-d₆) δ 1.6 (m, 1H), 1.8 (m, 1H), 2.4–3.05 (m, 4H), 3.4–3.9 (m, 4H), 3.8 (s, 6H), 4.0–4.3 (m 6.7–6.87 (m, 2H), 7.0–7.25 (m, 4H), 7.42 (t, 1H), 7.78 (s, 1H), 10.5 (d, 1H), 11.4 (d, 1H); MS (DCI/NH₃) m/z 504 (M+H)⁺. Anal. calcd for C₂₈H₃₀ClN₃O₄S·0.25H₂O: C, 61.76; H, 5.65; N, 7.72. Found: C, 61.81; H, 5.58; N, 7.59.

EXAMPLE 86

3-|2-((3aR,9bR)cis-6-Methoxy-2,3,3a,4,5,9b-hexahydro-|1H|-benz|e|isoindol-1-yl) ethyl|-7,8-dimethyl-pyrido|43-d|primidine-2,4(1H,3H)-dione hydrochloride Methyl 2,3-dimethyl-4-amino-pyridine-5-carboxylate (0.27 g, 1.50 mmol) was dissolved in 10 mL dichlormethane and cooled to −78° C. Triethylamine (0.42 mL, 3.00 mmol) was then added, followed by the dropwise addition of 0.78 mL (1.50 mmol) 1.93M phosgene in toluene solution. The reaction was stirred at −78° C. for 1h and then allowed to warm to room temperature, at which time a solution of the the product from Example 13J (0.50 g, 1.8 mmol) in 5 mL dichloromethane was added. The reaction was stirred at rt for 2 h and then quencched in 5% $NaHCO_3$, extracted with $CH_2Cl_2$, dried ($Na_2SO_4$), filtered, and evaporated. The resulting solid (0.42 g) was taken up in 30 mL of anhydrous tetrahydrofuran and 0.16 g (1.50 mmol) anhydrous potassium t-butoxide added. The reaction was stirred 2 h at room temperature, then quenched in 100 mL of pH 7 buffer solution. The reaction was extracted with ethyl acetate, dried ($Na_2SO_4$), and evaporated. The resulting product was treated with methanolic HCl to yield 0.23 g of the title compound as a white solid: mp 219°–225° C.; $^1$H NMR (300 MHz, DMSO-$d_6$) δ 1.6 (m, 1H), 1.8 (m, 1H), 2.4–3.1 (m, 2H), 2.5 (d, 6H), 3.3–3.7 (m, 4H), 3.8 (s, 6H), 3.9–4.3 (m 4H), 6.7–6.87 (m, 2H), 7.15 (t, 1H), 8.95 (s, 1H), 11.25 (d, 1H), 11.8 (s, 1H); MS (DCI/$NH_3$) m/z 421. Anal. calcd for $C_{24}H_{30}Cl_2N_4O_3 \cdot H_2O$: C, 56.36; H, 6.31; N, 10.95. Found: C, 56.19; H, 6.40; N, 10.83.

EXAMPLE 87

3-[2-((3aR,9bR)cis-6-Methoxy-2,3,3a, 4,5,9b-hexah dro-[1H]-benz[e]isoindol-1-yl) ethyl]1-2,4pteridinedione hydrochloride

EXAMPLE 87A

Methyl 3-(N-(2-chloroethyl)carbamido-2-pyrazinecarboxylate

Methyl 3-amino-2-pyrazinecarboxylate (10 g, 65.2 mmol) was dissolved in 200 mL anhydrous toluene, 2-chloroethyl isocyanate (5.6mL, 65.2 mmol) was added and the mixture was heated to gentle reflux. After 1.25 h, more 2-chioroethyl isocyanate (2.78 mL, 32.6 mmol) was added and the mixture was heated to 60° C. overnight. The mixture was evaporated to a brown solid, then purified by columnchromatography on silica gel eluting with a gradient of diethyl ether, 30:70 ethyl acetate:hexane, and ethyl acetate to give 1.1g (6%) of the title compound as a white solid mp 122–124° C. $^1$H NMR (300 MHz, DMSO-$d_6$) δ 3.52 (dd, 2H), 3.72 (t, 2H), 3.89 (s, 3H), 8.36 (d, 1H), 8.53 (d, 1H), 9.81 (s, 1H); MS (DCI/$NH_3$) 259 (M+H)$^+$.

EXAMPLE 87B

3-[2-((3aR,9bR)cis-6-Methoxy-2,3 3a,4,5,9b-hexahydro-|1H|-benz|e|isoindol-1-yl) ethyl|-2,4pteridinedione hydrochloride The product from Example 87A (0.264 g, 1.02 mmol) was combined with N, N'-diisopropylethylamine (0.533 mL, 3.06 mmol) and 0.245 g (1.02 mmol) of the compound resulting from Example 13J in 15 mL anhydrous toluene, then heated to 70° C. overnight. The mixture was evaporated to a brown solid, then purified by column chromatography on silica gel eluting with a gradient of 5:5:90 water formic acid:ethyl acetate, then 10:10:80 water:formic acid:ethyl acetate, evaporated with an excess of HCl/methanol , then heated to reflux in ethanol and filtered to give 0.041 g (10%) of the title compound as a white solid: mp 310°–312° C.; $^1$H NMR (300 MHz DMSOd6) δ 6 1.47 (m, 1H), 1.62 (m, 1H), 2.11–2.28 (m, 2H), 2.4–2.68 (m, 6H), 3.18–3.31 (m, 3H), 3.76 (s, 3H), 4.0 (t, 2H), 6.72 (d, 2H), 7.09 (t, 1H), 8.36 (d, 1H), 8.65 (d, 1H); HRMS calcd for $C_{21}H_{24}ClN_5O_3$: 394.1893; found: 394.1879. Anal. calcd for $C_{21}H_{24}ClN_5O_3 \cdot 1.5$ $H_2O$: C, 55.20; H, 5.96; N, 15.33. Found: C, 55.23; H, 5.32; N, 14.98.

EXAMPLE 88

3-|2-((3aR,9bR)cis-6-Methoxy-2,3,3a,4,5,9b-hexahydro-|1H|-benz|e|isoindol-1-yl) ethyl|-p-rimidino|4,5-d| pyrimidine-2,4(1H,3H)-dione hydrochloride

EXAMPLE 88A

Ethyl 4(N-(2-chloroethyl)carbamido)-5-pyrimidinecarboxylate

Ethyl 5-amino-6-pyrimidinecarboxylate (1.0g, 6.54 mmol) was combined with 2-chloroethyl isocyanate (0.834 ml, 9.81 mmol) in 65 mL anhydrous toluene and heated to reflux overnight. The mixture was evaporated to a white solid, then purified by column chromatography on silica gel eluting with 1: 1 hexanes:ethyl actetate to give 0.69 g (41%) of the title compound as a white solid: mp 115°–118° C.; $^1$H NMR (300 MHz DMSO-$d_6$) δ 3.61 (dd 2H), 3.76 (t, 2H), 3.91 (s, 3H), 8.96 (s, 1H), 9.05 (s, 1H), 9.28 (br t, 1H), 9.91 (s, 1H); MS (DCI/$NH_3$) m/z 258 (M+H)$^+$.

EXAMPLE 88B

3-[2-((3aR,9bR)cis-6-Methoxy-2,3,3a,4,5,9b-Hah dro-[1H]-benz[e]isoindol-1-yl)ethyl]-pyrimidino[4,5-d] pyrimidine-2,4(1H,3H)-dione hydrochloride The product from Example 88A (0.232 g, 0.897 mmol) was combined with N,N'-diisopropylethylamine (0.312 mL, 1.79 mmol), and 0.215 g (0.897 mmol) of the compound resulting from Example 13J in 10 ml $CH_3CN$; then heated to 70° C. overnight. The mixture was evaporated, then purified by column chromatography on silica gel eluting with a gradient of 1:1:30 water formic acid:ethyl acetate, then 5:5:90, then 10:10:90 in a sequential manner. The resulting homogeneous product was evaporated with an excess of HCl-methanol to produce 0.085 g of the title compound as a white solid: mp 277°–279° C.; $^1$H NMR (300 MHz DMSO-$d_6$) δ 1.6 (m, 1H), 1.78 (m, 1H), 2.6–2.76 (m, 2H), 2.98–3.06 (m, 1H), 3.44–3.52 (m, 3.78 (s, 1H), 3.90–4.26 (m, 5H), 6.71–6.86 (m, 2H), 7.18 (t, 1H), 9.11 (m, 12.58 (br s, 1H); MS (DCI/$NH_3$) 394 (M+H)$^+$. Anal. calcd for $C_{21}H_{28}C_1N_5O_3 \cdot 1.5H_2O$: C, 55.20; H, 5.96; N, 15.33. Found C, 54.85; H, 5.56; N ,15.15.

EXAMPLE 89–118

The following compounds can be prepared by the procedures described in the preceding examples and schemes.

| Example | Name |
| --- | --- |
| 89 | 2-[2-(cis-6-Methoxy-2,3,3a,4,5,9b-hexahydro-[1H]-benz[e]isoindol-1-yl)ethyl]-1,2,3,4-tetrahydroisoquinolin-1,3-dione |

-continued

| Example | Name |
| --- | --- |
| 90 | 2-[2-(cis-6-Methoxy-2,3,3a,4,5,9b-hexahydro-[1H]-benz[e]isoindol-1-yl)ethyl]-6,7-dimethoxy-1,2,3,4-tetrahydroisoquinoline |
| 91 | 3-[2-(cis-6-Methoxy-2,3,3a,4,5,9b-hexahydro-[1H]-benz[e]isoindol-1-yl)ethyl]-2,4-pteridineidone |
| 92 | 3-[2-(cis-6-Methoxy-2,3,3a,4,5,9b-hexahydro-[1H]-benz[e]isoindol-1-yl)ethyl]-7-(3,4-dimethoxyphenyl)-thieno[3,2-d]pyrimidine-2,4-(1H,3H)-dione |
| 93 | 3-[2-(cis-6-Methoxy-2,3,3a,4,5,9b-hexahydro-[1H]-benz[e]isoindol-1-yl)ethyl]-1-methyl-thieno[2,3-d]pyrimidine-2,4-(1H,3H)-dione |
| 94 | 3-[2-(cis-6-Methoxy-2,3,3a,4,5,9b-hexahydro-[1H]-benz[e]isoindol-1-yl)ethyl]-6-chloro-thieno[2,3-d]pyrimidine-2,4(1H,3H)-dione |
| 95 | 3-[2-(cis-6-Methoxy-2,3,3a,4,5,9b-hexahydro-[1H]-benz[e]isoindol-1-yl)ethyl]-1-methyl-6-dimethylaminocarbonyl-thieno[2,3-d]pyrimidine-2,4(1H,3H)-dione |
| 96 | 3-[2-(cis-6-Methoxy-2,3,3a,4,5,9b-hexahydro-[1H]-benz[e]isoindol-1-yl)ethyl]-oxazolo[5,4-d]pyrimidine-5,7(4H,6H)-dione |
| 97 | 3-[2-(cis-6-Methoxy-2,3,3a,4,5,9b-hexahydro-[1H]-benz[e]isoindol-1-yl)ethyl]-7-amino-oxazolo[5,4-d]pyrimidin-5(6H)-one |
| 98 | 1-[2-(cis-6-Methoxy-2,3,3a,4,5,9b-hexahydro-[1H]-benz[e]isoindol-1-yl)ethyl]-3,9-dimethyl-[1H]-purine-2,6-dione |
| 99 | 1-[2-(cis-6-Methoxy-2,3,3a,4,5,9b-hexahydro-[1H]-benz[e]isoindol-1-yl)ethyl]-3,7-dimethyl-[7H]-imidazo[4,5-d]pyrimidin-2,6-dione |
| 100 | 3-[2-(cis-6-Methoxy-2,3,3a,4,5,9b-hexahydro-[1H]-benz[e]isoindol-1-yl)ethyl]-7-methoxy-quinazoline-2,4(1H,3H)-dione |
| 101 | 3-[2-(cis-6-Methoxy-2,3,3a,4,5,9b-hexahydro-[1H]-benz[e]isoindol-1-yl)ethyl]-7,8-ethylenedioxy-quinazoline-2,4(1H,3H)-dione |
| 102 | 3-[2-(cis-6-Hydroxy-2,3,3a,4,5,9b-hexahydro-[1H]-benz[e]isoindol-1-yl)ethyl]-6,7-dimethoxy-quinazoline-2,4(1H,3H)-dione |
| 103 | 2-[2-(cis-6-Methoxy-2,3,3a,4,5,9b-hexahydro-[1H]-benz[e]isoindol-1-yl)ethyl]-4-amino-6,7-dimethoxy-quinazoline |
| 104 | 3-[2-(cis-6-Methoxy-2,3,3a,4,5,9b-hexahydro-[1H]-benz[e]isoindol-1-yl)ethyl]-6-chloro-7-methoxy-quinazoline-2,4-(1H,3H)-dione |
| 105 | 3-[2-(cis-6-Methoxy-2,3,3a,4,5,9b-hexahydro-[1H]-benz[e]isoindol-1-yl)ethyl]-7-cyano-quinazoline-2,4(1H,3H)-dione |
| 106 | 3-[2-(trans-6-Methoxy-2,3,3a,4,5,9b-hexahydro-[1H]-benz[e]isoindol-1-yl)ethyl]-[1H,3H]-quinazoline-2,4(1H,3H)-dione |
| 107 | 3-[2-(trans-6-Methoxy-2,3,3a,4,5,9b-hexahydro-[1H]-benz[e]isoindol-1-yl)ethyl]-thieno[3,2-d]pyrimidine-2,4(1H,3H)-dione |
| 108 | 3-[2-(trans-6-Methoxy-2,3,3a,4,5,9b-hexahydro-[1H]-benz[e]isoindol-1-yl)ethyl]-8-methoxy-quinazoline-2,4(1H,3H)-dione |
| 109 | 3-[2-(trans-6-Methoxy-2,3,3a,4,5,9b-hexahydro-[1H]-benz[e]isoindol-1-yl)ethyl]-6,7-dimethoxy-quinazoline-2,4(1H,3H)-dione |
| 110 | 3-[2-(trans-6-Methoxy-2,3,3a,4,5,9b-hexahydro-[1H]-benz[e]isoindol-1-yl)ethyl]-7-chloro-quinazoline-2,4(1H,3H)-dione |
| 111 | 3-[2-(trans-6-Methoxy-2,3,3a,4,5,9b-hexahydro-[1H]-benz[e]isoindol-1-yl)ethyl]-7-carbomethoxy-1uinazoline-2,4(1H,3H)-dione |
| 112 | 3-[2-(trans-6-Methoxy-2,3,3a,4,5,9b-hexahydro-[1H]-benz[e]isoindol-1-yl)ethyl]-6,7,8-trimethoxy-quinazoline-2,4(1H,3H)-dione |
| 113 | 3-[2-(trans-6-Methoxy-2,3,3a,4,5,9b-hexahydro-[1H]-benz[e]isoindol-1-yl)ethyl]-1-methyl-quinazoline-2,4(1H,3H)-dione |
| 114 | 3-[2-(trans-6-Methoxy-2,3,3a,4,5,9b-hexahydro-[1H]-benz[e]isoindol-1-yl)ethyl]-6,7-dimethoxy-quinazoline-4(3H)-one |
| 115 | 3-[2-(trans-6-Methoxy-2,3,3a,4,5,9b-hexahydro-[1H]-benz[e]isoindol-1-yl)ethyl]-6,7-methylenedioxyquinazoline-2,4(1H,3H)-dione |
| 116 | 3-[2-(trans-6-Methoxy-2,3,3a,4,5,9b-hexahydro-[1H]-benz[e]isoindol-1-yl)ethyl]-6,7-ethylenedioxyquinazoline-2,4(1H,3H)-dione |
| 117 | 3-[2-(trans-6-Methoxy-2,3,3a,4,5,9b-hexahydro-[1H]-benz[e]isoindol-1-yl)ethyl]-1-methyl-6,7-dimethoxyquinazoline-2,4(1H,3H)-dione |
| 118 | 3-[2-(trans-6-Methoxy-2,3,3a,4,5,9b-hexahydro-[1H]-benz[e]isoindol-1-yl)ethyl]-6-methoxy-thieno[3,2-d]pyrimidine-2,4(1H,3H)-dione |

The foregoing is merely illustrative of the invention and is not intended to limit the invention to the disclosed compounds. Variations and changes which are obvious to one skilled in the art are intended to be within the scope and nature of the invention which are defined in the appended claims.

We claim:

1. A compound selected from the group consisting of:

3-[2-((3aR,9bR)-cis-6-methoxy-2,3,3a,4,5,9b-hexahydro-[1H]-benz [e]isoindol-1-yl)ethyl]-1-methyl-7-methoxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-1-(2-methoxyethyl)-6,7-dimethoxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-7,8-methylenedioxyquinazoline-2,4(1H,3H)-dione;

3-[2-((3aR,9bR)-cis-6-methoxy-2,3,3a,4,5,9b-hexahydro-[1H]-benz[e]isoindol-1-yl)ethyl]-6,7-methylenedioxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-6,7-dimethoxyquinazoline-4(3H)-one;

3-[2-((3aR,9bR)cis-6-methoxy-2,3,3a,4,5,9b-hexahydro-[1H]-benz[e]isoindol-1-yl)ethyl]-7,8-dimethoxyquinazoline-4(3H)-one;

3-[2-((3aR,9bR)-cis-6-methoxy-2,3,3a,4,5,9b-hexahydro-[1H]-benz[e]isoindol-1-yl)ethyl]-7,8-dimethylpyrido[3,2-d]pyrimidine-2,4(1H,3H)-dione;

3-[2-((3aR,9bR)-cis-9-methoxy-2,3,3a,4,5,9b-hexahydro-[1H]-benz[e]isoindol-1-yl)butyl]-6,7-dimethoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carbomethoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carboisopropoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-carbopropoxyquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-nitroquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-methoxy-8-methyl-quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7-ethoxy-8-methyl-quinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7,8-dimethylquinazoline-2,4(1H,3H)-dione;

3-[2-((3aR,9bR)cis-6-methoxy-2,3,3a,4,5,9b-hexahydro-[1H]-benz[e]isoindol-1-yl)ethyl]-7,8-dimethoxyquinazoline-2,4(1H,3H)-dione;

3-[2-((3aR,9bR)cis-6-ethoxy-2,3,3a,4,5,9b-hexahydro-[1H]-benz[e]isoindol-1-yl)ethyl]-6,7-dimethoxyquinazoline-2,4(1H,3H)-dione; and 3-[2-((3aR,9bR)cis-6-Ethyl-2,3,3a,4,5,9b-hexahydro-[1H]-benz[e]isoindol-1-yl)ethyl]-6,7-dimethoxyquinazoline-2,4(1H,3H)-dione;

or a pharmaceutically acceptable salt thereof.

2. A pharmaceutical composition comprising a therapeutically effective amount of a compound of claim 1 in combination with a pharmaceutically acceptable carrier.

3. A method of antagonizing α-1 receptors in a host mammal in need of such treatment comprising administering a therapeutically effective amount of a compound of claim 1.

4. A method of treating benign prostatic hyperplasia (BPH) in a host mammal in need of such treatment comprising administering a therapeutically effective amount of a compound of claim 1.

5. A method of treating benign prostatic hyperplasia (BPH) in a host mammal in need of such treatment comprising administering a therapeutically effective amount of a compound of claim 1 in combination with a 5-α reductase inhibitor.

6. The method of claim 5 wherein said 5-α reductase inhibitor is finasteride.

* * * * *